(12) United States Patent
Creelman et al.

(10) Patent No.: US 8,071,846 B2
(45) Date of Patent: Dec. 6, 2011

(54) YIELD AND STRESS TOLERANCE IN TRANSGENIC PLANTS II

(75) Inventors: Robert A. Creelman, Castro Valley, CA (US); Neal I. Gutterson, Oakland, CA (US); Oliver J. Ratcliffe, Oakland, CA (US); T. Lynne Reuber, San Mateo, CA (US); R. Eric Cerny, Chesterfield, MO (US); Kimberly Faye Zobrist Duff, St. Louis, MO (US); Susanne Kjemtrup-Lovelace, Chapel Hill, NC (US); Robert J. Meister, St. Peters, MO (US); Marie E. Petracek, Glendale, MO (US); Thomas Ruff, Wildwood, MO (US); Qingzhang Xu, O'Fallon, MO (US)

(73) Assignees: Monsanto Company, St. Louis, MO (US); Mendel Biotechnology, Inc., Hayward, CA (US)

( * ) Notice: Subject to any disclaimer, the term of this patent is extended or adjusted under 35 U.S.C. 154(b) by 0 days.

(21) Appl. No.: 12/750,949

(22) Filed: Mar. 31, 2010

(65) Prior Publication Data

US 2010/0192249 A1 Jul. 29, 2010

Related U.S. Application Data

(60) Division of application No. 11/821,448, filed on Jun. 22, 2007, now Pat. No. 7,692,067, and a continuation-in-part of application No. 11/642,814, filed on Dec. 20, 2006, which is a division of application No. 10/666,642, filed on Sep. 18, 2003, now Pat. No. 7,196,245.

(60) Provisional application No. 60/411,837, filed on Sep. 18, 2002, provisional application No. 60/434,166, filed on Dec. 17, 2002, provisional application No. 60/465,809, filed on Apr. 24, 2003, provisional application No. 60/817,886, filed on Jun. 29, 2006.

(51) Int. Cl.
*C12N 15/82* (2006.01)
*A01H 5/00* (2006.01)
*A01H 5/10* (2006.01)

(52) U.S. Cl. ........ 800/298; 800/278; 800/290; 800/287; 800/260

(58) Field of Classification Search .................. None
See application file for complete search history.

(56) References Cited

U.S. PATENT DOCUMENTS

| | | | |
|---|---|---|---|
| 5,994,622 | A | 11/1999 | Jofuku et al. |
| 6,121,513 | A | 9/2000 | Zhang et al. |
| 6,664,446 | B2 | 12/2003 | Heard et al. |
| 6,706,866 | B1 | 3/2004 | Thomashow et al. |
| 6,717,034 | B2 | 4/2004 | Jiang |
| 6,835,540 | B2 | 12/2004 | Broun et al. |
| 6,946,586 | B1 | 9/2005 | Fromm et al. |
| 7,109,393 | B2 | 9/2006 | Gutterson et al. |
| 7,135,616 | B2 | 11/2006 | Heard et al. |
| 7,193,129 | B2 | 3/2007 | Reuber et al. |
| 7,196,245 | B2 | 3/2007 | Jiang et al. |
| 7,223,904 | B2 | 5/2007 | Heard et al. |
| 7,238,860 | B2 | 7/2007 | Ratcliffe et al. |
| 7,345,217 | B2 | 3/2008 | Zhang et al. |
| 7,511,190 | B2 | 3/2009 | Creelman et al. |
| 7,598,429 | B2 | 10/2009 | Heard et al. |
| 7,601,893 | B2 | 10/2009 | Reuber et al. |
| 7,635,800 | B2 | 12/2009 | Ratcliffe et al. |
| 7,659,446 | B2 | 2/2010 | Sherman et al. |
| 7,663,025 | B2 | 2/2010 | Heard et al. |
| 2002/0076775 | A1 | 6/2002 | Crane et al. |
| 2003/0041356 | A1 | 2/2003 | Reuber et al. |
| 2003/0061637 | A1 | 3/2003 | Jiang et al. |
| 2003/0093837 | A1 | 5/2003 | Keddie et al. |
| 2003/0101481 | A1 | 5/2003 | Zhang et al. |
| 2003/0121070 | A1 | 6/2003 | Adam et al. |
| 2003/0131386 | A1 | 7/2003 | Samaha et al. |
| 2003/0188330 | A1 | 10/2003 | Heard et al. |
| 2003/0226173 | A1* | 12/2003 | Ratcliffe et al. ............. 800/281 |
| 2004/0019927 | A1* | 1/2004 | Sherman et al. ............. 800/278 |
| 2004/0098764 | A1 | 5/2004 | Heard et al. |
| 2004/0128712 | A1 | 7/2004 | Jiang et al. |
| 2005/0086718 | A1 | 4/2005 | Heard et al. |
| 2005/0097638 | A1 | 5/2005 | Jiang et al. |
| 2005/0155117 | A1 | 7/2005 | Century et al. |
| 2005/0172364 | A1 | 8/2005 | Heard et al. |
| 2006/0008874 | A1 | 1/2006 | Creelman et al. |

(Continued)

FOREIGN PATENT DOCUMENTS

EP 1033405 9/2000

(Continued)

OTHER PUBLICATIONS

Dinkins et al (2002, Plant Cell Physiol. 43(7):743-750).*
Bowie et al, Science 247:1306-1310, 1990.*
McConnell et al, Nature 411 (6838):709-713, 2001.*
WO08/005210, Jan. 10, 2008, Mendel Biotech, Inc., ISR.
EP03779082.1, Sep. 20, 2007, Mendel Biotech, Inc., Suppl Search.
EP03779082.1, Jul. 13, 2007, Mendel Biotech, Inc., Partial Search.
EP03779082.1, Jan. 30, 2008, Mendel Biotech, Inc., Office action.
EP1546336, Apr. 15, 2004, Mendel Biotech, Inc., Exam reports Sep. 21, 2009.
U.S. Appl. No. 09/394,519, filed Sep. 13, 1999, Zhang, J. et al.
U.S. Appl. No. 12/573,311, filed Oct. 5, 2009, Heard, J. et al.

(Continued)

*Primary Examiner* — Stuart F. Baum
(74) *Attorney, Agent, or Firm* — Cooley LLP

(57) ABSTRACT

Polynucleotides and polypeptides incorporated into expression vectors have been introduced into plants and were ectopically expressed. The polypeptides of the invention have been shown to confer at least one regulatory activity and confer increased yield, greater height, greater early season growth, greater canopy coverage, greater stem diameter, greater late season vigor, increased secondary rooting, more rapid germination, greater cold tolerance, greater tolerance to water deprivation, reduced stomatal conductance, altered C/N sensing, increased low nitrogen tolerance, increased low phosphorus tolerance, or increased tolerance to hyperosmotic stress as compared to the control plant as compared to a control plant.

26 Claims, 17 Drawing Sheets

U.S. PATENT DOCUMENTS

Figure 1:
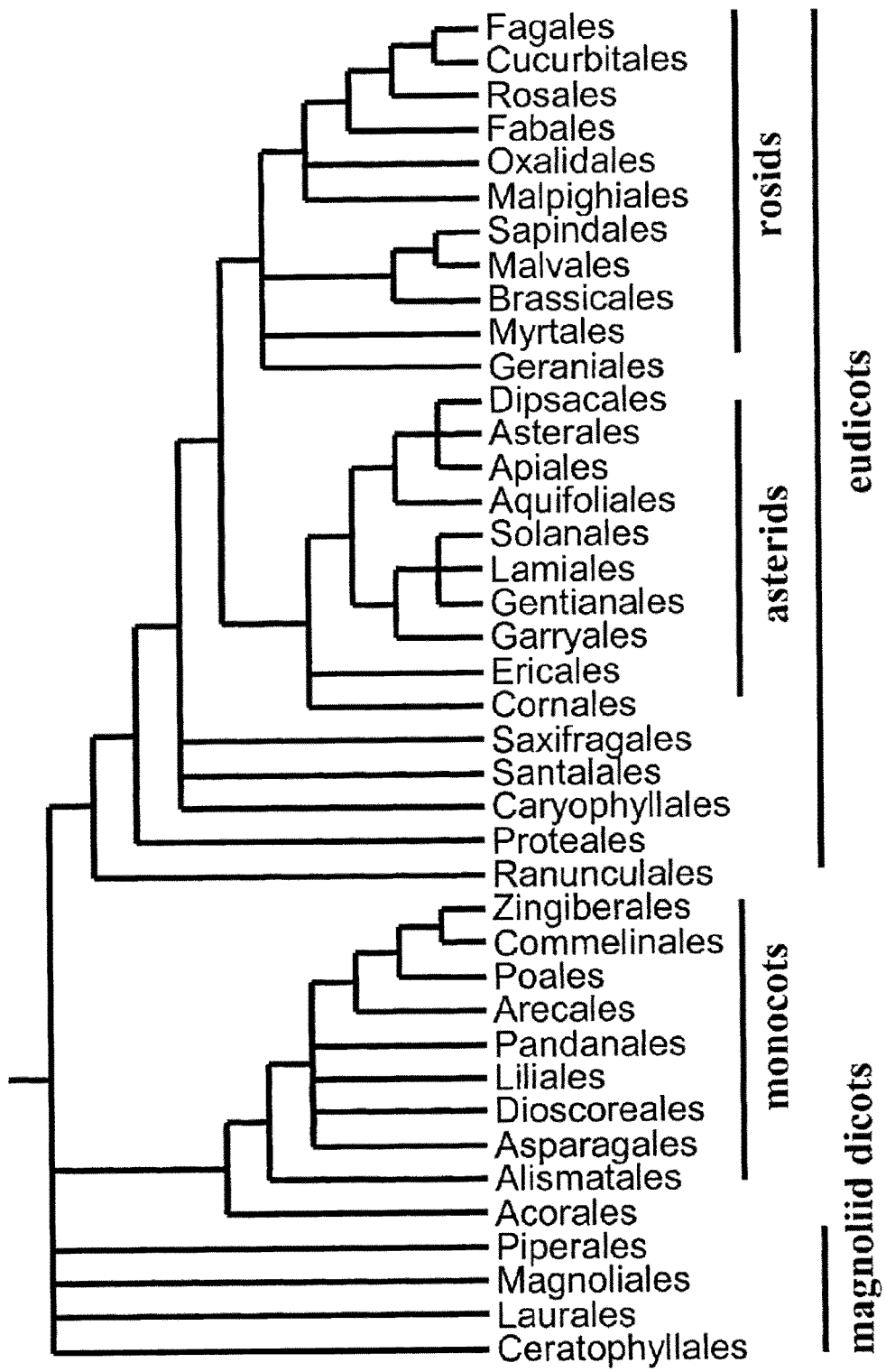

| | | | |
|---|---|---|---|
| 2006/0015972 | A1 | 1/2006 | Heard et al. |
| 2006/0162018 | A1 | 7/2006 | Gutterson et al. |
| 2007/0022495 | A1 | 1/2007 | Reuber et al. |
| 2007/0101454 | A1 | 5/2007 | Jiang et al. |
| 2007/0199107 | A1 | 8/2007 | Ratcliffe et al. |
| 2007/0226839 | A1 | 9/2007 | Gutterson et al. |
| 2008/0010703 | A1 | 1/2008 | Creelman et al. |
| 2008/0155706 | A1 | 6/2008 | Riechmann et al. |
| 2008/0163397 | A1 | 7/2008 | Ratcliffe et al. |
| 2008/0229448 | A1 | 9/2008 | Libby et al. |
| 2008/0301836 | A1 | 12/2008 | Century et al. |
| 2008/0301840 | A1 | 12/2008 | Gutterson et al. |
| 2008/0301841 | A1 | 12/2008 | Ratcliffe et al. |
| 2008/0313756 | A1 | 12/2008 | Zhang et al. |
| 2009/0049566 | A1 | 2/2009 | Zhang et al. |
| 2009/0138981 | A1 | 5/2009 | Repetti et al. |
| 2009/0151015 | A1 | 6/2009 | Adam et al. |
| 2009/0192305 | A1 | 7/2009 | Riechmann et al. |
| 2009/0205063 | A1 | 8/2009 | Zhang et al. |
| 2009/0265807 | A1 | 10/2009 | Kumimoto et al. |
| 2009/0265813 | A1 | 10/2009 | Gutterson et al. |
| 2009/0276912 | A1 | 11/2009 | Sherman et al. |

FOREIGN PATENT DOCUMENTS

| | | |
|---|---|---|
| EP | 1406483 | 2/2002 |
| EP | 1485490 | 2/2003 |
| WO | WO03/013227 | 2/2003 |
| WO | PCT/US2004/031349 | 8/2004 |
| WO | WO2004/076638 | 9/2004 |
| WO | WO2005/001050 | 1/2005 |
| WO | WO2006/076099 | 7/2006 |

OTHER PUBLICATIONS

U.S. Appl. No. 12/577,662, filed Oct. 12, 2009, Reuber, T. et al.
U.S. Appl. No. 12/557,449, filed Sep. 10, 2009, Repetti, P. et al.
U.S. Appl. No. 09/627,348, filed Jul. 28, 2000, Thomashow, Michael et al.
U.S. Appl. No. 09/489,376, filed Jan. 21, 2000, Heard, J. et al.
U.S. Appl. No. 09/489,230, filed Jan. 21, 2000, Broun P. et al.
U.S. Appl. No. 09/506,720, filed Feb. 17, 2000, Keddie, James et al.
U.S. Appl. No. 09/533,030, filed Mar. 22, 2000, Keddie, James et al.
U.S. Appl. No. 09/533,392, filed Mar. 22, 2000, Jiang, C-Z. et al.
U.S. Appl. No. 09/532,591, filed Mar. 22, 2000, Samaha, R. et al.
U.S. Appl. No. 09/533,648, filed Mar. 22, 2000, Riechmann, Jose Luis et al.
U.S. Appl. No. 10/290,627, filed Nov. 7, 2002, Riechmann, Jose Luis et al.
U.S. Appl. No. 09/713,994, filed Nov. 16, 2000, Keddie, James et al.
U.S. Appl. No. 09/837,944, filed Apr. 18, 2001, Creelman, Robert et al.
U.S. Appl. No. 09/594,214, filed Jun. 14, 2000, Jones, J. et al.
U.S. Appl. No. 10/456,882, filed Jun. 6, 2003, Riechman, Jose Luis et al.
U.S. Appl. No. 10/171,468, filed Jun. 14, 2002, Creelman, Robert et al.
U.S. Appl. No. 12/376,569, filed Aug. 3, 2007, Creelman, Robert et al.
U.S. Appl. No. 12/526,042, filed Feb. 7, 2008, Repetti, Peter P. et al.
U.S. Appl. No. 12/638,750, filed Dec. 15, 2009, Ratcliffe. O. et al.
U.S. Appl. No. 12/702,109, filed Feb. 8, 2010, Reichmann, et al.
U.S. Appl. No. 12/705,845, filed Feb. 15, 2010, Heard, J. et al.
U.S. Appl. No. 12/721,304, filed Mar. 10, 2010, Creelman, Robert et al.
U.S. Appl. No. 09/474,435, filed Dec. 28, 1999, Cao, Y. et al., entire doc.
Bowie et al., "Deciphering the message in protein sequences: tolerance to amino acid substitutions." Science, 1990, vol. 247: 1306-1310.
Chen et al., "Expression Profile Matrix of *Arabidopsis* Transcription Factor Genes Suggests Their Putative Functions in Response to Environmental Stresses." Plant Cell, 2002,14: 559-574.
Chen and Chen, "Potentiation of Developmentally Regulated Plant Defense Response by AtWRYKY18, a Pathogen-Induced *Arabidopsis* Transcription Factor." Plant Physiology,2002, 129: 706-716.
de Pater et al., "Characterization of a Zinc-Dependent Transcriptional Activator from *Arabidopsis*." Nucleic Acids Res., 1996, 24: 4624-4631.
Dellagi et al., "A Potato Gene Encoding a WRKY-like Transcription Factor is Induced in Interactions with *Erwinia caratovora* Subsp. *Atroseptica* . . . " Mol. Plant Microbe Interact, 2000, 13: 1092-1101.
Du and Chen, "Identification of Genes Encoding Receptor-like Protein Kinases as Possible Targets of Pathogen- and Salicylic Acid-Induced WRKY DNA-binding proteins in *Arabidopsis*." Plant Journal, 2000, 24: 837-847.
Eulgem et al., "Early Nuclear Events in Plant Defense Signaling: Rapid Gene Activation by WRKY Transcription Factors." EMBO Journal, 1999, 18: 4689-4699.
Eulgem et al., "The WRKY Superfamily of Plant Transcription Factors." Trends Plant Science, 2000,5: 199-206.
Ishiguro and Nakamura, "The Defective in Anther Dehiscience Gene Encodes a Novel Phospholipase A1 Catalyzing the Initial Step of Jasmonic Acid Biosynthesis " Mol. Gen. Genet., 1994 244: 563-571.
Johnson et al., "Transparent Testa Glabra2, a Trichome and Seed Coat Development Gene of *Arabidopsis*, Encodes a WRKY Transcription Factor." Plant Cell, 2002, 14: 1359-1375.
Kalde et al., "Members of the *Arabidopsis* WRKY Group III Transcription Factors Are Part of Different Plant Defense Signaling Pathways." Molecular Plant-Microbe Interactions, 2003,16: 295-305.
Kushnir et al., NCBI Accession No. AF426252; *Arabidopsis thaliana* WRKY Transcription Factor 51 (WRKY51) mRNA. Complete CDs, Nov. 8, 2001.
Kushnir et al., NCBI Accession No. AF452174; *Arabidopsis thaliana* WRKY Family Transcription Factor 75 (WRKY75) mRNA. Complete CDs, Dec. 27, 2001.
Lebel et al., "Functional Analysis of Regulatory Sequences Controlling PR-1 Gene Expression in *Arabidopsis*." Plant Journal, 1998, 16: 223-233.
Li et al., "The WRKY70 Transcription Factor: A Node of Convergence for JasmonateMediated and Salicylate-Mediated Signals in Plant Defense." Plant Cell, 2004,16: 319-331.
Mare et al., "HV-WRKY38: A New Transcription Factor Involved in Cold-and DroughtResponse in Barley." Plant Mol. Biology, 2004, 55: 399-416.
Mcconnell et al., "Role of *Phabulosa* and *phavoluta* in determining radial patterning in shoots." Nature, 2001, 411 (6838): 709-713.
Miao et al., "Targets of the WRKY53 transcription factor and its role during leaf senescence in *Arabidopsis*." Plant Molecular Biology, 2004, vol. 55, No. 6, pp. 853-867.
Pnueli et al., "Molecular and Biochemical Mechanisms Associated With Dormancy and 34 Drought Tolerance in the Desert Legume *Retama raetam*." Plant Journal, 2002, 31: 319-330 .
Robatzek and Somssich, "A New Member of the *Arabidopsis* WRKY Transcription Factor Family, AtWRKY, is Associated with Both Senescence-and Defense-related Processes." Plant Journal, 2001, 28: 123-133.
Robatzek and Somssich, "Targets of ArWRKY6 Regulation During Plant Senescence andPathogen Defense." Genes Dev., 2002, 16: 1139-1149.
Rushton et al., "Interaction of Elicitor-Induced DNA-binding Proteins with Elicitor Response Elements in the Promoters of Parsley PR1 Genes." EMBO Journal, 1996, 15: 5690-5700.
Rushton et al., "Synthetic Plant Promoters Containing Defined Regulatory Elements Provide Novel Insights into Pathogen-and Wound-Induced Signaling." Plant Cell, 2002,14: 749-762.
Sun et al., "A Novel WRKY Transcription Factor, SUSIBA2, Participates in Sugar Signaling in Barley by Binding to the Sugar-Responsive Elements of the Isol Promoter." Plant Cell, 2003, 15: 2076-2092.
Tepperman et al., "Multiple Transcription-Factor Genes are Early Targets of Phytochrome A Signaling." Proc. National Acad. of Science USA, 2001, 98: 9437-9444.
Town et al., NCBI Accession No. NM_125877; *Arabidopsis thaliana* WRKY Transcription Factor (At5g64810) mRNA. Complete CDs, Jan. 10, 2002.
Ulker et al., NCBI Accession No. AY071847; *Arabidopsis thaliana* WRKY Transcription Factor 50 (WRKY50) mRNA. Complete CDs, Jan. 20, 2002.

Wang et al., "An Oligo Selection Procedure for Identification of Sequence-Specific DNA Binding Activities Associated with the Plant Defense Response." Plant Journal, 1998, 16: 515-522.

Yamasaki et al., "Solution Structure of an *Arabidopsis* WRKY DNA Binding Domain." Plant Cell, 2005,17: 944-956.

Yang et al., "Expression of the REB transcriptional activator in rice grains improves the yield of recombinant proteins whose genes are controlled by a Reb-responsive promoter." PNAS 98(20): 11438-11443, 2001.

Yang et al., "A Pathogen-and Salicylic Acid-induced WRKY DNA-binding Activity Recognizes the Elicitor Response Element of Tobacco Class I Chitinase Gene Promoter." Plant Journal, 1999, 18: 141-149.

Yu et al., "Evidence for an Important Role of WRKY DNA Binding Proteins in the Regulation of NPR1 Gene Expression." Plant Cell, 2001,13: 1527-1540.

Zhang and Wang, "The WRKY Transcription Factor Superfamily: Its Origin in Eukaryotes and Expansion in Plants." BMC Evol. Biology, 2005,5:1.

Zou et al., "The WRKY Gene from Creosote Bush Encodes an Activator of the Abscisic Acid Signaling Pathway." Journal of Biol. Chem., 2004, 279: 55770-55779.

Ben-Naim et al., (2006). "The CCAAT binding factor can mediate interactions between CONSTANS-like proteins and DNA." Plant J 46, 462-476 Plant J 46, 462-476.

Borden (1998). "RING fingers and B-boxes: zinc-binding protein-protein interaction domains." Biochem Cell Biol 76, 351-358.

Khanna et al., (2006). "Functional profiling reveals that only a small number of phytochrome-regulated early-response genes in *Arabidopsis* . . ." Plant Cell 18, 2157-2171.

Lippuner et al., (1996). "Two classes of plant cDNA clones differentially complement yeast calcineurin mutants and increase salt tolerance of wild-type yeast." J Biol Chem 271, 12859-12866.

Robson et al., (2001). "Functional importance of conserved domains in the flowering-time gene CONSTANS demonstrated by analysis of mutant alleles and transgenic plants." Plant J 28, 619-631.

Torok et al., (2001). "Two B or not two B? Overview of the rapidly expanding B-box family of proteins." Differentiation 67,63-71.

Putterill,J. CONSTANS protein. Jan. 18, 1996. NCBI accession No. CAA64407. USA.

Putterill,J. *A.thaliana* mRNA for CONSTANS protein. Dec. 15, 1997. NCBI accession No. Y10555. USA.

Putterill,J. *A.thaliana* constans gene. Dec. 15, 1997. NCBI accession no. Y10556. USA.

Co Co Constans; Transcription factor/zinc binding [*Arabidopsis thaliana*]. Nov. 7, 2008. ENTREZ Gene ID: 831441. USA.

Wenkel, S. et al. Nov. 2006. CONSTANS and the CCAAT Box Binding Complex Share a Functionally Important Domain and Interact to Regulate Flowering of *Arabidopsis*. Plant Cell 18: 2971-2984. USA.

Imaizumi, T. et al. Jul. 2005. FKF1 F-Box Protein Mediates Cyclic Degradation of a Repressor of CONSTANS in *Arabidopsis*. Science 309: 293-297. USA.

Sjödin, P. et al. Mar. 2007. Recent degeneration of an old duplicated flowering time gene in *Brassica nigra*. Heredity 98: 375-384. United Kingdom.

Ayre, B.G. and Turgeon, R. Aug. 2004. Graft Transmission of a Floral Stimulant Derived from CONSTANS. Plant Physiol. 135: 2271-2278. USA.

Yoo, S.K. et al. Oct. 2005. CONSTANS Activates Suppressor of Overexpression of CONSTANS 1 through Flowering Locus T to Promote Flowering in *Arabidopsis*. Plant Physiol. 139: 770-778. USA.

Mizoguchi T. et al. Aug. 2005. Distinct Roles of GIGANTEA in Promoting Flowering and Regulating Circadian Rhythms in *Arabidopsis*. Plant Cell 17: 22552270. USA.

Chen, M., and Ni, M. Jun. 2006. RFI2, a RING-domain zinc finger protein, negatively regulates CONSTANS expression and photoperiodic flowering. Plant J. 46: 823-833. USA.

Nakamichi, N. et al. Jun. 2007. *Arabidopsis* Clock-Associated Pseudo-Response Regulators PRR9, PRR7 and PRR5 Coordinately and Positively Regulate Flowering Time Through the Canonical CONSTANS-Dependent . . . Plant Cell. Physiol. 48:822-832. United Kingdom.

Kushnir et al. Nov. 2001. *Arabidopsis thaliana* transcription factor WRKY51 (WRKY51) mRNA, complete cds. Ncbi acc. No. AF426252.

Seki e tal. Dec. 2002. *Arabidopsis thaliana* At3g21150 mRNA for unknown protein, complete cds, clone: RAFL18-04-G04. NCBI acc. No. AK117844.

Tair Gene Model: AT5G15840.1 Sep. 18, 2008. TAIR accession: gene 2143205.

NCBI acc.No. NM_101262; *Arabidopsis thaliana* WRKY Family Transcription Factor (AtIg13960) mRNA. Complete CDs, Feb. 23, 2005.

BH478747 Ayele et al., "BOGXY23TF BOGX *Brassica oleracea* genomic clone BOGXY23, genomic survey sequence." Dec. 13, 2001.

BU873581 Unneberg, et al., "Q057B04 *Populus* flower cDNA library *Populus trichocarpa* cDNA 5 prime, mRNA sequence." Oct. 16, 2002.

AW034552 Alcala, et al., "EST278168 tomato callus, TAMU *Solanum lycopersicum* cDNA clone cLEC24E8, mRNA sequence." May 18, 2001.

C95300 Galibert, et al., "NrtA-type periplasmic nitrate transport binding protein, probable SMa0585 [imported]—*Sinorhizobium meliloti* (strain 1021) magaplasmid pSymA." Sep. 30, 2001.

AAAA01000340 Yu, et al., "*Oryza sativa* (indica cultivar-group) scaffold000340, whole genome shotgun sequence." Apr. 4, 2002.

BQ594583 Herwig, et al., "E012444-024-024-P06-SP6 MPIZ-ADIS-024-developing root *Beta vulgaris* cDNA clone 024-024-P06 5-Prime, mRNA sequence." Dec. 6, 2002.

B1469275 Shoemaker, et al., "sai09g02.y1 Gm-c1053 Glycine max cDNA clone Genome Systems Clone ID: Gm-c1053-2979 5' similar to TR:O81834 O81834 Hypo.." Jul. 8, 2004.

BU046688 Callahan, et al., "PP_LEa0027D08f Peach developing fruit mesocarp *Prunus persica* cDNA clone PP_LEa0027D08f, mRNA sequence." Aug. 26, 2002.

AP000604 Nakamura,Y. "*Arabidopsis thaliana* genomic DNA, chromosome 3, P1 clone: MSA6, complete sequence." Oct. 15, 1999.

GenBank Accession No. AF426252, Nov. 11, 2004, Abstract, 2 pages.

GenBank Accession No. AK117844, Dec. 13, 2002, Abstract, 2 pages.

* cited by examiner

```
                                                                   B-domain
                                                         |─────────────────────────────────
G4000  (8)   -----------MGAARDSTAAGQKRGTGTRCELCGGAAAVHCAADSAFLCLRCDAKVHG
G4012  (16)  -----------MEVG-----NGKCGGGGAGCELCGGVAAVHCAADSAFLCLVCDDKVHG
G4011  (14)  ------------------------MGGEAERCALCGAAAAVHCEADAAFLCAACDAKVHG
G4297  (18)  -----------MGAA------GDAAAAGTRCELCGGAAAVHCAADSAFLCPRCDAKVHG
G4007  (10)  ------------------------MKRACELCSQEAALHCASDEAFLCFDCDDRVHK
G4009  (12)  ------------------------MAVKVCELCKGEAGVYCDSDAAYLCFDCDSNVHN
G1988  (2)   ------------------------MVSFCELCGAEADLHCAADSAFLCRSCDAKFHA
G4004  (4)   ------------------------MKPKTCELCHQLASLYCPSDSAFLCFHCDAAVHA
G4005  (6)   ------------------------MKGKTCELCDQQASLYCPSDSAFLCSDCDAAVHA
G4014  (38)  ------------------------MRKCELCNSPAKLFCESDQASLCWKCDAKVHS
G1481  (34)  ------------------------MGKKCDLCNGVARMYCESDQASLCWDCDGKVHG
G1478  (32)  MCRGFEKEEERRSDNGGCQRLCTESHKAPVSCELCGENATVYCEADAAFLCRKCDRWVHS
G1929  (36)  MCRGLNNEESRRSDGGGCRSLCTR-PSVPVRCELCDGDASVFCEADSAFLCRKCDRWVHG
G4019  (44)  MCKGAEGEKQHGFCSSFLHKECAT--RSATCCELCGLQASLYCQADDAYLCRKCDKRVHE
Cnsns  (69)                          CXLCXXXAXXXCXXDXAXLCXXCDXXXHX
                                                         |─────────────────────────────────
                                                                   B-domain
```

FIG. 4A

```
                    B-domain
G4000  (8)   ANFLASRHVRRRLVP-----RRAADPE---ASSAASSGSSCVS---------------T
G4012  (16)  ANFLASRHRRRRLG------VEVVDEE---DDARSTASSSCVS---------------T
G4011  (14)  ANFLASRHHRRRVAAGAVVVVEVEEEEGYESGASAASSTSCVS---------------T
G4297  (18)  ANFLASRHVRRRLP------RGGADSG------ASASSGSCLS---------------T
G4007  (10)  ANFLVARHVRQTLCSQCKSLTGKFISGERSSSSLVPICPSC----------CSSTTSTS
G4009  (12)  ANFLVARHIRRVICSGCGSITGNPFSGDTPSLSRV-TCSSCSPGNKELDSISCSSSSTLS
G1988  (2)   SNFLFARHFRRVICPNCKSLTQNFVSGPLLPWPPRTTCCSES---------SSSSCCSS
G4004  (4)   ANFLVARHLRRLLCSKCNRFAAIHIS-GAISRHLSSTCTSCSL---EIPSAD-SDSLPSS
G4005  (6)   ANFLVARHLRRLLCSKCNRFAGFHISSGAISRHLSSTCSSCSP---ENPSADYSDSLPSS
G4014  (38)  ANFLVTKHPRILLCHVCQSLTAWHGTG----PKFVPTMSVCNT---------------
G1481  (34)  ANFLVAKHTRCLLCSACQSLTPWKATG----LRLGPTFSVCES---------------
G1478  (32)  ANFLARRHLRRVICTTCRKLTRRCLVG-------------------------------
G1929  (36)  ANFLAWRHVRRVLCTSCQKLTRRCLVG-------------------------------
G4019  (44)  ANFLALRHIRCFLCNTCQNLTRRYLIG-------------------------------
Cnsns  (69)  XNFLXXRHXR
             ─────────
              B-domain
```

FIG. 4B

```
G4000  (8)   ADSAESAATAPAPCPSRTAGR---------------------RAPARARRPRAEAVLEG
G4012  (16)  ADSASSTAAAAALE-SEDVRR---------------------RGRRGRRAPRAEAVLEG
G4011  (14)  ADSDVAASAA-----ARRGRR---------------------RRPRAAARPRAEVVLEG
G4297  (18)  ADSVQSRAAPPP---GRGRGR---------------------RAP-----PRAEAVLEG
G4007  (10)  SDCISSTESSAAEKMGRERKR----VRACSSSVSDISG----EKAAAVTDSKA-EGIFAI
G4009  (12)  SACISSTETTRFENT-RKGVK----TTSSSSSVRNIPGRSLRDRLKRSRNLRS-EGVFVN
G1988  (2)   LDCVSSSELS---STTRDVNR----ARGRENRVN---------AKAVAVTVA-DGIFVN
G4004  (4)   STCVSSSESCSTNQIKAEKKRRRRRRSFSSSSVTDDASP---AAKKRRRNGGSVAEVFEK
G4005  (6)   STCVSSSESCSTKQIKAEKKR-----SWSGSSVTDDASP---AAKKRQRSGGS-EEVFEK
G4014  (38)  --CVNNNSTETCSQQNHEDDD-------------------------DDGTGEDHAEND
G1481  (34)  --CVALKN----------------------------------------AGGGRGNRVLSE
G1478  (32)  ------------------------------------------------DN-FNVVLPE
G1929  (36)  ------------------------------------------------DHDFHVVLPS
G4019  (44)  ------------------------------------------------AS-IEVVLPA
```

FIG. 4C

```
G4000  (8)   WAKRMGFAAG--PARRRAAAAAAALRALGRGVAAARVPLRVGMAGALWSEVPAG----CR
G4012 (16)   WAKRMGLSSG--AARRRAAAAGAALRAVGRGVAASRVPIRVAMAAALWSEVASSSSRRRR
G4011 (14)   WGKRMGLAAG--AARRRAAAAGRALRACGGDVAAARVPLRVAMAAALWWEVAAHR--VSG
G4297 (18)   WARRKGVAAG--PACRR----------------RVPLRVAMAAARWSEVSAG------
G4007 (10)   WCRRLGLNGNNSNCNSVVVVSLASRALGLCLERTTALPLRACLAASFWFGLRMCG-----
G4009 (12)   WCKRLGLNGS------LVVQRATRAMALCFGR-LALPFRVSLAASFWFGLRLCG-----
G1988  (2)   WCGKLGLNRDLTN----AVVSYAS--LALAVETRPRATKRVFLAAAFWFGV---------
G4004  (4)   WSREIGLGLG------VNGNRVASNALSVCLGKWRSLPFRVAAATSFWLGLRFCG-----
G4005  (6)   WSREIGLGLGLG----VNGNRVASNALSVCLGKWRWLPFRVAAATSFWLGLRFCG-----
G4014 (38)   DGGVAEDDDD--------------------------------------------------
G1481 (34)   NRGQEEVNSL--------------------------------------------------
G1478 (32)   IR----------------------------------------------------------
G1929 (36)   VT----------------------------------------------------------
G4019 (44)   NINW--------------------------------------------------------
```

FIG. 4D

```
G4000  (8)   GNGGEEASLLQRLEAPAHVPARLVLTPASWMARRPDARQEDP----EEGWAECS------
G4012  (16)  RPGAGQAALLLRLEASAHVPARLLLTVASWMAR--ASTPPAA----EEGWAECS------
G4011  (14)  VSGAGHADALRRLEACAHVPARLLTAVASSMARARARRRAAAD--NEEGWDECSCSEAPN
G4297  (18)  --GGAEAAVLA-------VAAWWMTRAAR--ARPPAAGAPDL----EEGWAECSPEFVVR
G4007  (10)  DKTVATWPNLRRLEAISGVPAKLIVAVEGKIARVMAVRRRRPRQVLEEGWAECNV-----
G4009  (12)  DKSVTTWENLRRLEEVSGVPNKLIVTVEMKIEQALRSKRLQLQKEMEEGWAECSV-----
G1988  (2)   -KNTTTWQNLKKVEDVTGVSAGMIRAVESKLARAMTQQLRRWRVDSEEGWAENDNV----
G4004  (4)   DRGLATCQNLARLEAISGVPAKLILGAHANLARVFTHRR-----ELQEGWGES-------
G4005  (6)   DRGLASCQNLARLEAISGVPVKLILAAHGDLARVFTHRR-----ELQEGWGES-------
G4014  (38)  -DDDEENQVVPWTSTPPPPASTSSNSVTTSSTRFSDVEEGGSD-----------------
G1481  (34)  -CSDDE------IGSSSAQGSNYSRPLKRSAFKSTVVV----------------------
G1478  (32)  --MIAR------IEEHS--SDHKIPFVFL-------------------------------
G1929  (36)  --TVGETT----VENRSEQDNHEVPFVFL-------------------------------
G4019  (44)  --TIGNLPSNRGIHRKCSRMHNNLSLLL--------------------------------
```

FIG. 4E

```
G4000  (8)   ----------------
G4012  (16)  ----------------
G4011  (14)  ALGGPHVSDTARQK
G4297  (18)  QGPHPSATTCGRR-
G4007  (10)  ----------------
G4009  (12)  ----------------
G1988  (2)   ----------------
G4004  (4)   ----------------
G4005  (6)   ----------------
G4014  (38)  ----------------
G1481  (34)  ----------------
G1478  (32)  ----------------
G1929  (36)  ----------------
G4019  (44)  ----------------
```

FIG. 4F

US 8,071,846 B2

YIELD AND STRESS TOLERANCE IN TRANSGENIC PLANTS II

RELATIONSHIP TO COPENDING APPLICATIONS

This application is a divisional application of prior-filed U.S. patent application Ser. No. 11/821,448, filed Jun. 22, 2007, which issued as U.S. Pat. No. 7,692,067 on Apr. 6, 2010. U.S. patent application Ser. No. 11/821,448 claims the benefit of U.S. provisional application 60/817,886, filed Jun. 29, 2006 (expired). U.S. patent application Ser. No. 11/821,448 is also a continuation-in-part of prior-filed U.S. patent application Ser. No. 11/642,814, filed Dec. 20, 2006 (pending), which is a divisional application of prior-filed U.S. patent application Ser. No. 10/666,642, filed Sep. 18, 2003, and which issued as U.S. Pat. No. 7,196,245 on Mar. 27, 2007, the latter application claiming the benefit of prior-filed U.S. provisional application 60/411,837, filed Sep. 18, 2002 (expired), U.S. provisional application 60/434,166, filed Dec. 17, 2002 (expired), and U.S. provisional application 60/465,809, filed Apr. 24, 2003 (expired). The entire contents of each of these applications are hereby incorporated by reference.

JOINT RESEARCH AGREEMENT

The claimed invention, in the field of functional genomics and the characterization of plant genes for the improvement of plants, was made by or on behalf of Mendel Biotechnology, Inc. and Monsanto Company as a result of activities undertaken within the scope of a joint research agreement in effect on or before the date the claimed invention was made.

"REFERENCE TO A "SEQUENCE LISTING," A TABLE, OR A COMPUTER PROGRAM LISTING APPENDIX SUBMITTED ON A COMPACT DISK

The Sequence Listing written in file-9-1. APP, 86,016 bytes, created on Jun. 19, 2007 on duplicate copies of compact disc of the written form of the Sequence Listing, i.e., "Copy 1 of 3" and "Copy 2 of 3", and the sequence information recorded in computer readable form on compact disc, i.e., "Copy 3 of 3" for Application No. 60/817,886, Creelman et al., IMPROVED YIELD AND STRESS TOLERANCE IN TRANSGENIC PLANTS, is hereby incorporated by reference.

FIELD OF THE INVENTION

The present invention relates to plant genomics and plant improvement.

BACKGROUND OF THE INVENTION

The Effects of Various Factors on Plant Yield

Yield of commercially valuable species in the natural environment may be suboptimal as plants often grow under unfavorable conditions, such as at an inappropriate temperature or with a limited supply of soil nutrients, light, or water availability. For example, nitrogen (N) and phosphorus (P) are critical limiting nutrients for plants. Phosphorus is second only to nitrogen in its importance as a macronutrient for plant growth and to its impact on crop yield. Plants have evolved several strategies to help cope with P and N deprivation that include metabolic as well as developmental adaptations. Most, if not all, of these strategies have components that are regulated at the level of transcription and therefore are amenable to manipulation by transcription factors. Metabolic adaptations include increasing the availability of P and N by increasing uptake from the soil though the induction of high affinity and low affinity transporters, and/or increasing its mobilization in the plant. Developmental adaptations include increases in primary and secondary roots, increases in root hair number and length, and associations with mycorrhizal fungi (Bates and Lynch (1996); Harrison (1999)).

Nitrogen and carbon metabolism are tightly linked in almost every biochemical pathway in the plant. Carbon metabolites regulate genes involved in N acquisition and metabolism, and are known to affect germination and the expression of photosynthetic genes (Coruzzi et al. (2001)) and hence growth. Early studies on nitrate reductase (NR) in 1976 showed that NR activity could be affected by Glc/Suc (Crawford (1995); Daniel-Vedele et al. (1996)). Those observations were supported by later experiments that showed sugars induce NR mRNA in dark-adapted, green seedlings (Cheng et al. (1992)). C and N may have antagonistic relationships as signaling molecules; light induction of NR activity and mRNA levels can be mimicked by C metabolites and N-metabolites cause repression of NR induction in tobacco (Vincentz et al. (1992)). Gene regulation by C/N (carbon-nitrogen balance) status has been demonstrated for a number of N-metabolic genes (Stitt (1999)); Coruzzi et al. (2001)). Thus, a plant with altered C/N sensing may exhibit improved germination and/or growth under nitrogen-limiting conditions.

Water deficit is a major limitation of crop yields. In water-limited environments, crop yield is a function of water use, water use efficiency (WUE; defined as aerial biomass yield/water use) and the harvest index (HI; the ratio of yield biomass to the total cumulative biomass at harvest). WUE is a complex trait that involves water and $CO_2$ uptake, transport and exchange at the leaf surface (transpiration). Improved WUE has been proposed as a criterion for yield improvement under drought. Water deficit can also have adverse effects in the form of increased susceptibility to disease and pests, reduced plant growth and reproductive failure. Useful genes for expression especially during water deficit are genes which promote aspects of plant growth or fertility, genes which impart disease resistance, genes which impart pest resistance, and the like. These limitations can delay growth and development, reduce productivity, and in extreme cases, cause the plant to die. Enhanced tolerance to these stresses would lead to yield increases in conventional varieties and reduce yield variation in hybrid varieties.

Another factor affecting yield is the number of plants that can be grown per acre. For crop species, planting or population density varies from a crop to a crop, from one growing region to another, and from year to year.

A plant's traits, including its biochemical, developmental, or phenotypic characteristics that enhance yield or tolerance to various abiotic stresses, may be controlled through a number of cellular processes. One important way to manipulate that control is through transcription factors—proteins that influence the expression of a particular gene or sets of genes. Transformed and transgenic plants that comprise cells having altered levels of at least one selected transcription factor, for example, possess advantageous or desirable traits. Strategies for manipulating traits by altering a plant cell's transcription factor content can therefore result in plants and crops with commercially valuable properties.

SUMMARY OF THE INVENTION

An object of this invention is to provide plants which can express genes to increase yield of commercially significant plants, as well as to ameliorate the adverse effects of water or nutrient deficit.

The present invention thus pertains to novel recombinant polynucleotides, expression vectors, host plant cells and transgenic plants that contain them, and methods for producing the transgenic plants.

The recombinant polynucleotides may include any of the following sequences:
(a) the nucleotide sequences found in the sequence listing;
(b) nucleotide sequences encoding polypeptides found in the sequence listing;
(c) sequence variants that are at least 30% sequence identical to any of the nucleotide sequences of (a) or (b);
(d) polypeptide sequences that are at least 30% identical, or at least 32%, at least 33%, at least 36%, at least 40%, at least 45%, or at least 67% identical in their amino acid sequence to any of SEQ ID NOs: 2, 4, 6, 8, 10, 12, 14, 16, 18, 20, 22, or 24;
(e) orthologous and paralogous nucleotide sequences that are at least 40% identical to any of the nucleotide sequences of (a) or (b);
(e) nucleotide sequence that hybridize to any of the nucleotide sequences of (a) or (b) under stringent conditions, which may include, for example, hybridization with wash steps of 6×SSC and 65° C. for ten to thirty minutes per step; and
(f) polypeptides, and the nucleotide sequences that encode them, having a B-box zinc finger conserved domain required for the function of regulating transcription and altering a trait in a transgenic plant, the conserved domain being at least about 56% sequence identity, or at least about 58% sequence identity, or at least about 60% sequence identity, or at least about 65%, or at least about 67%, or at least about 70%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%, identical in its amino acid residue sequence to the B-box zinc-finger (ZF) conserved domains of SEQ ID NO: 2, 4, 6, 8, 10, 12, 14, 16, 18, 20, 22 or 24 (i.e., a polypeptide listed in the sequence listing, or encoded by any of the above nucleotide sequences, the conserved domains being represented by SEQ ID NOs: 45-56, respectively). The conserved domains of the invention listed in Table 1 comprise a domain required for the function of regulating transcription and altering a trait in a transgenic plant, said trait selected from the group consisting of increasing yield, increasing height, altering C/N sensing, increasing low nitrogen tolerance, increasing low phosphorus tolerance, increasing tolerance to water deprivation, reducing stomatal conductance, and increasing tolerance to a hyperosmotic stress, as compared to the control plant. Additionally, the polypeptides of the invention may comprise several signature residues closer to the C-terminus than the B-box domain. These residues comprise, in order from N to C termini:

$W-X_4-G$
(SEQ ID NO: 62, where X represents any amino acid; seen in FIG. 4D)

$R-X_3-A-X_3-W$
(SEQ ID NO: 57, where X represents any amino acid; seen in FIG. 4D)
and EGWXE
(SEQ ID NO: 58; where X represents any amino acid; seen in FIG. 4E)

The expression vectors, and hence the transgenic plants, of the invention, comprise putative transcription factor polynucleotides sequences and, in particular, B-box zinc finger sequences. When any of these polypeptide of the invention is overexpressed in a plant, the polypeptide confers at least one regulatory activity to the plant, which in turn in manifested in a trait selected from the group consisting of increased yield, greater height, increased secondary rooting, greater cold tolerance, greater tolerance to water deprivation, reducing stomatal conductance, altered C/N sensing, increased low nitrogen tolerance, increased low phosphorus tolerance, and increased tolerance to hyperosmotic stress as compared to the control plant.

The invention is also directed to transgenic seed produced by any of the transgenic plants of the invention, and to methods for making the transgenic plants and transgenic seed of the invention.

BRIEF DESCRIPTION OF THE SEQUENCE LISTING AND DRAWINGS

The Sequence Listing provides exemplary polynucleotide and polypeptide sequences of the invention. The traits associated with the use of the sequences are included in the Examples.

Incorporation of the Sequence Listing. The Sequence Listing provides exemplary polynucleotide and polypeptide sequences. The copy of the Sequence Listing, being submitted electronically with this patent application, provided under 37 CFR §1.821-1.825, is a read-only memory computer-readable file in ASCII text format. The Sequence Listing is named "MBI-0076DIV_ST25.txt", the electronic file of the Sequence Listing was created on Mar. 25, 2010, and is 85,416 bytes in size (84 kilobytes in size as measured in MS-WINDOWS). The Sequence Listing is herein incorporated by reference in its entirety.

FIG. 1 shows a conservative estimate of phylogenetic relationships among the orders of flowering plants (modified from Soltis et al. (1997)). Those plants with a single cotyledon (monocots) are a monophyletic Glade nested within at least two major lineages of dicots; the eudicots are further divided into rosids and asterids. *Arabidopsis* is a rosid eudicot classified within the order Brassicales; rice is a member of the monocot order Poales. FIG. 1 was adapted from Daly et al. (2001).

Figure 2:
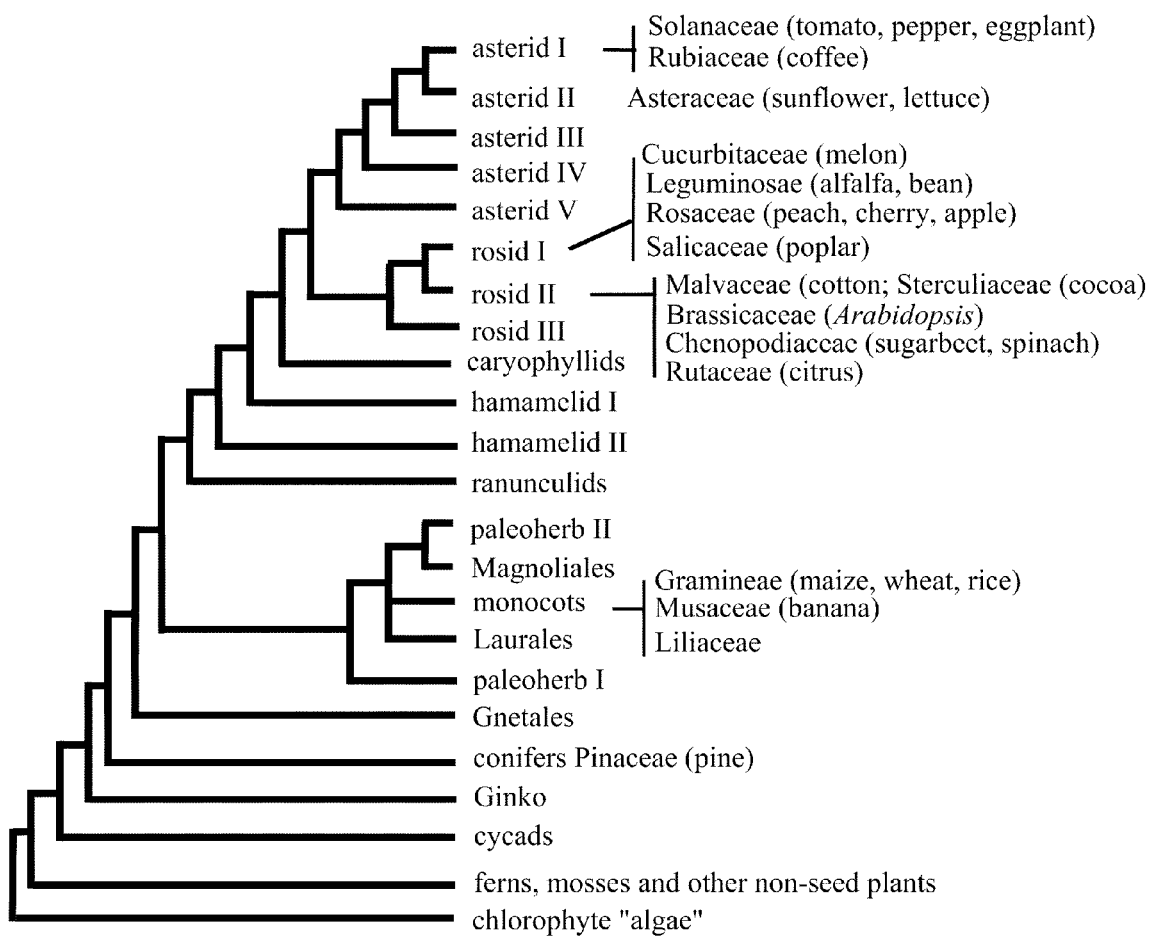

FIG. 2 shows a phylogenic dendogram depicting phylogenetic relationships of higher plant taxa, including clades containing tomato and *Arabidopsis*; adapted from Ku et al. (2000); and Chase et al. (1993).

Figure 3:
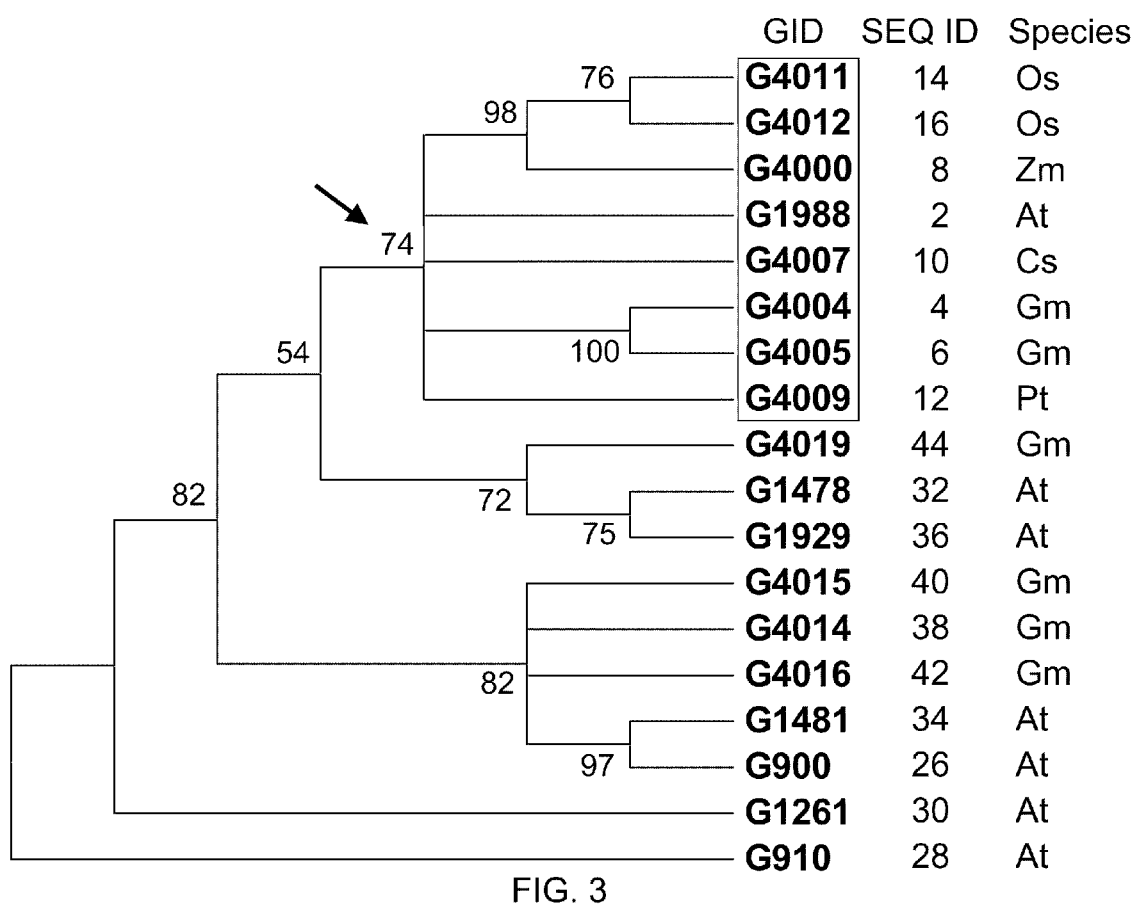

In FIG. 3, a phylogenetic tree and multiple sequence alignments of G1988 and related full length proteins were constructed using ClustalW (CLUSTAL W Multiple Sequence Alignment Program version 1.83, 2003). ClustalW multiple alignment parameters were:

Gap Opening Penalty: 10.00
Gap Extension Penalty: 0.20
Delay divergent sequences: 30%
DNA Transitions Weight: 0.50
Protein weight matrix: Gonnet series
DNA weight matrix: IUB
Use negative matrix: OFF A FastA formatted alignment was then used to generate a phylogenetic tree in MEGA2 software (MEGA2 (http://www.megasoftware.net) using the neighbor joining algorithm and a p-distance model. A test of phylogeny was done via bootstrap with 1000 replications and Random Seed set to default. Cut off values of the bootstrap tree were set to 50%. Closely-related homologs of G1988 are considered as being those proteins within the node of the tree below with a bootstrap value of 74, bounded by G4011 and G4009 (indicated by the box around these sequences). The ancestral sequence is represented by the node of the tree indicated by the arrow in FIG. 3 having a bootstrap value of 74. Abbreviations: At—*Arabidopsis thaliana*; Ct—*Citrus sinensis*; Gm—*Glycine max*; Os—*Oryza sativa*; Pt—*Populus trichocarpa*; Zm—*Zea mays*.

FIGS. 4A-4F show a Clustal W alignment of the G1988 Glade and related proteins. SEQ ID NOs: appear in parentheses after each Gene IDentifier (GID). Some members of the G1988 Glade appear in the large boxes in each of FIGS. 4A-4F. The highly conserved B-box zinc-finger (ZF) conserved domain (B domain) is identified in FIGS. 4A-4B by the horizontal line below the alignment. Several characteristic or signature residues within characteristic motifs outside of and nearer to the C-terminus than the B-domain are indicated by the small dark triangles in FIGS. 4D and 4E.

Figure 5:
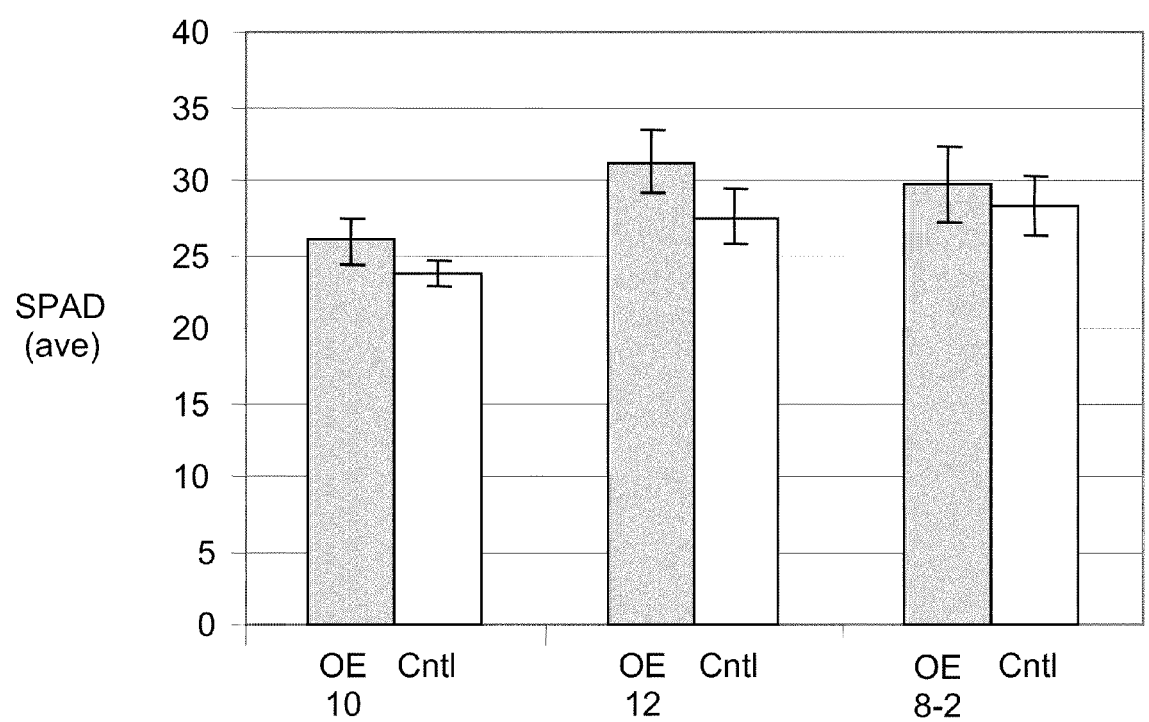

FIG. 5 shows the average measure leaf SPAD chlorophyll level (SPAD or "Soil Plant Analysis Development", measured with a Minolta SPAD-502 leaf chlorophyll meter, vertical axis) measured in G1988 *Arabidopsis* overexpressor lines (OE lines 10, 12 and 8-2; horizontal axis). Also shown are measurements for control plants (Cntl) for each of the three experimental lines. Plants were grown in 10 hr light, 0.1 mM $NH_4NO_3$, pre-bolting and were assayed 7.5 weeks after planting. The error bars represent the standard deviation of the mean. The three G1988 lines had higher chlorophyll content under low nitrogen conditions than the controls. Results obtained for lines 10 and 12 were significant at $p<0.01$.

Figure 6:
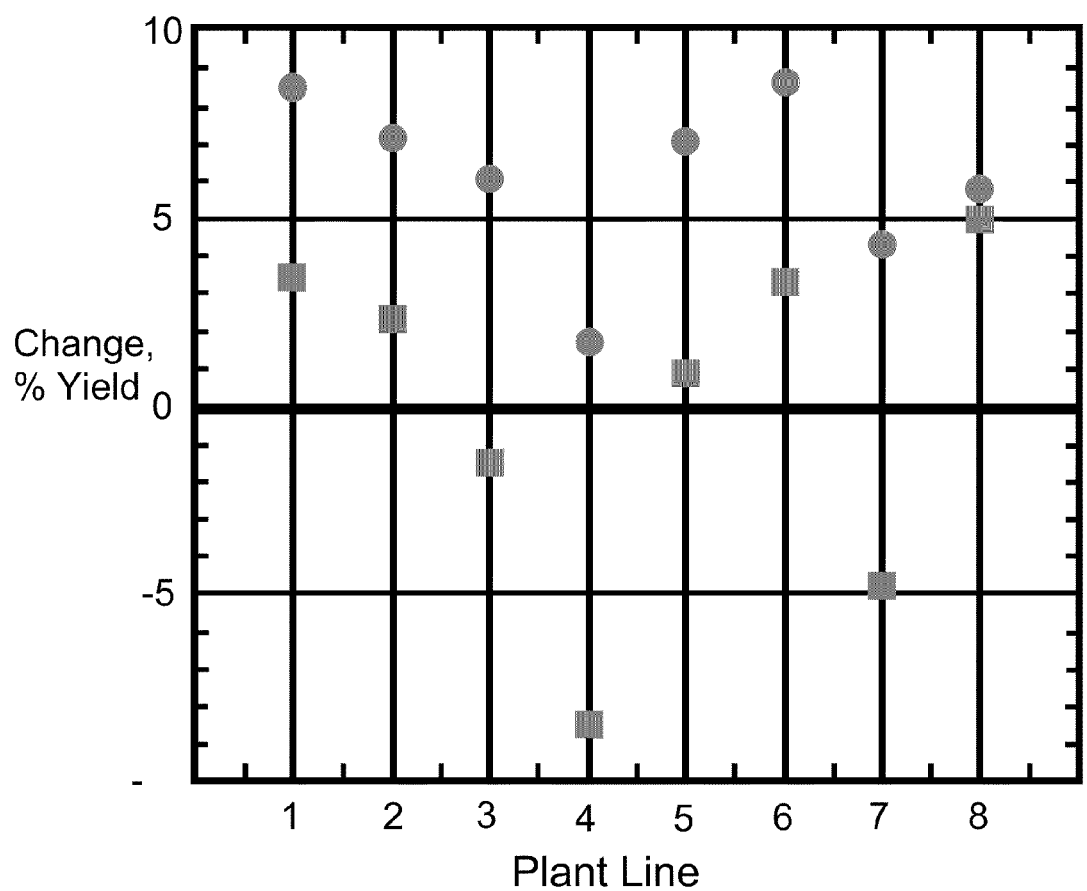

FIG. 6 compares the effects on yield (vertical axis: change in percentage yield) in various lines (horizontal axis) of transgenic soybean plants overexpressing G1988 (35S::G1988) in year 2004 and 2005 field trials. Data are averaged across multiple locations and a consistent increase in yield, as compared with controls harboring an empty construct, was observed. In the 2005 analysis, G1988 significantly increased yield in 17 of 19 locations. If line 4, which unlike other lines presented in this graph showed little or no expression of G1988 in leaf tissue, is removed from the analysis, the average yield increase in 2005 was about 6.7%.

Figure 7:
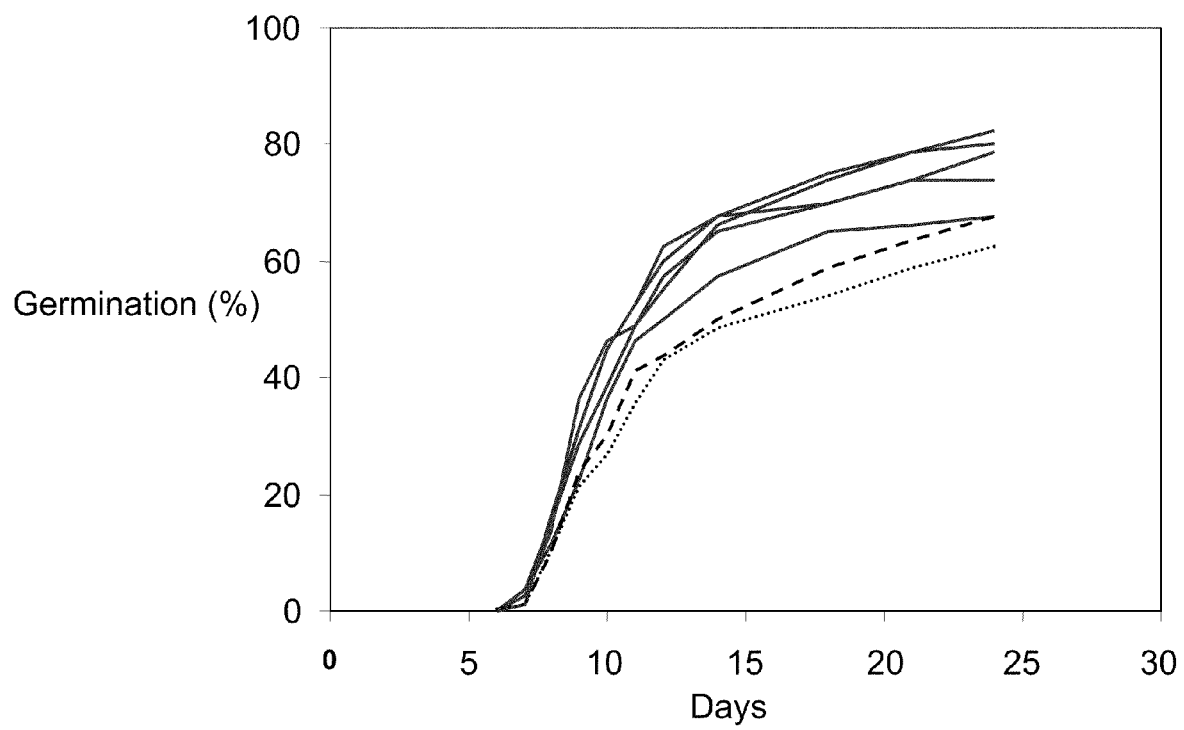

FIG. 7 shows experimental data obtained in 2005 with seed from a California field trial comparing a wild-type control soybean line and numerous 35S::G1988 overexpressing lines of soybean plants. The dotted curve represents the percentage of wild type germinating line. The dashed curve above it represents a low overexpressor that ultimately produced a small increase in yield over the control. The darker solid curves above that of the low overexpressor represent other 35S::G1988 overexpressors showing a higher degree of expression, ultimately produced significantly higher yield, and improved germination in cold as compared to the controls. Similar results were obtained with seed derived in the same year from a field trial conducted in Kansas and two field trials in Illinois. These data demonstrated that G1988 overexpression results in improved cold germination of soy.

Figure 8:
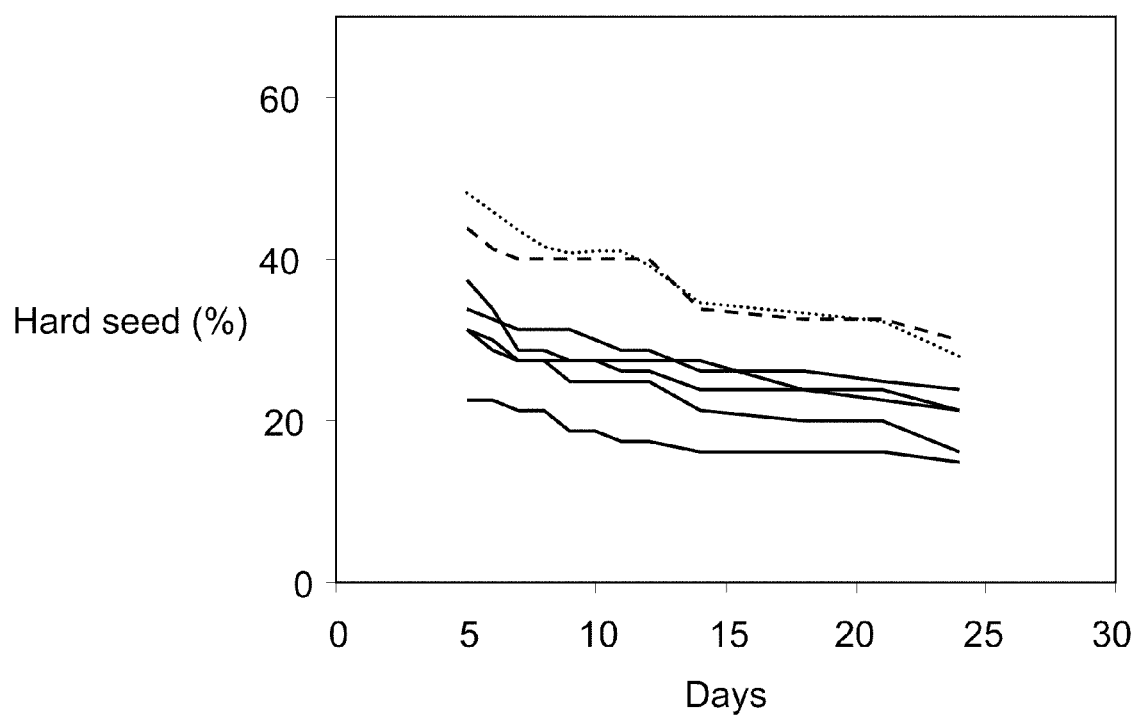
Figure 9:
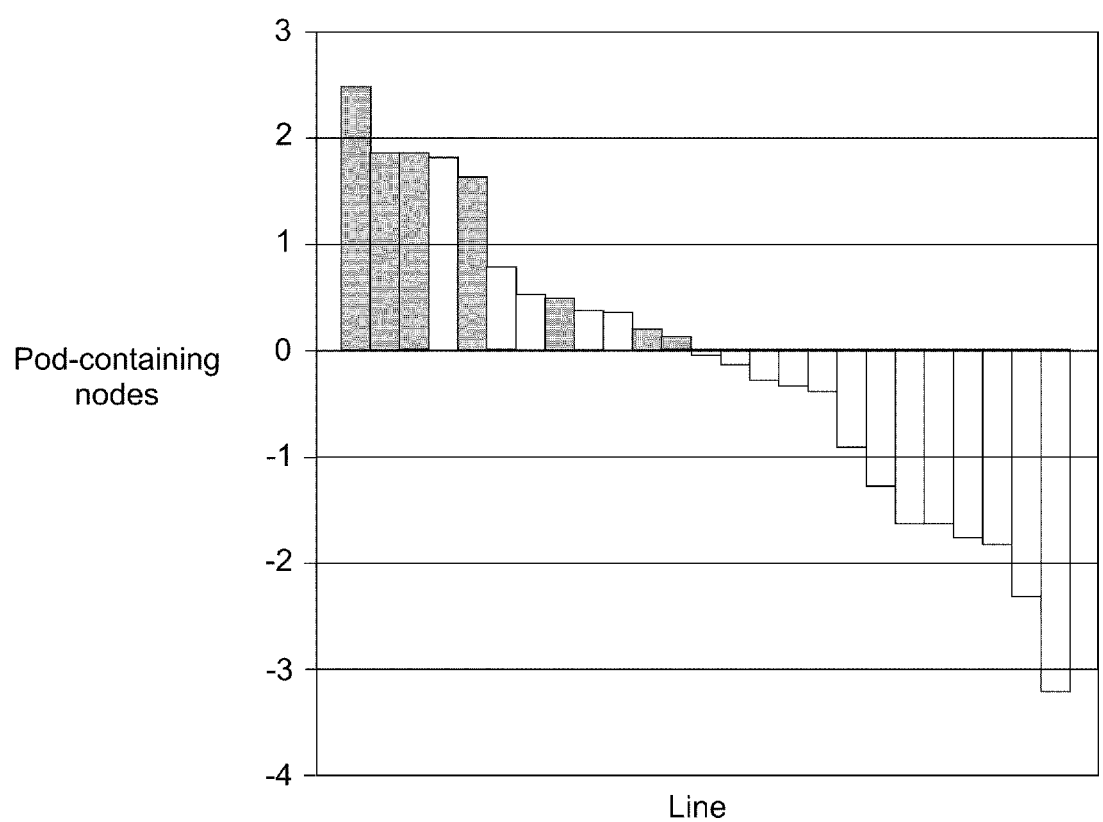

FIG. 8 compares the overall germination of soybeans from the California field trial. The germination of the control (dotted curve) was poor and it was noted that a high percentage of the seed were "hard seed", a stress-induced phenomenon that results in seeds that resist imbibition under standard conditions. The dashed curve below the dotted control curve represents the low overexpressor that appeared to have a similar percentage of hard seed, that is, the same percentage of seed that did not germinate at various time points, as the control. The darker solid curves below the control and low overexpressor represent other 35S::G1988 overexpressing lines that had a lower percentage of hard seed and eventually produced a higher yield than controls FIG. 9 shows the mean number of pod-containing mainstem nodes, relative to the parental control line represented by the "0" line, observed in various lines of soybean plants overexpressing a number of sequences. The shaded bars denote G1988 overexpressing lines, which generally produced a significantly greater number of pod-bearing nodes than the control plants.

Figure 10:
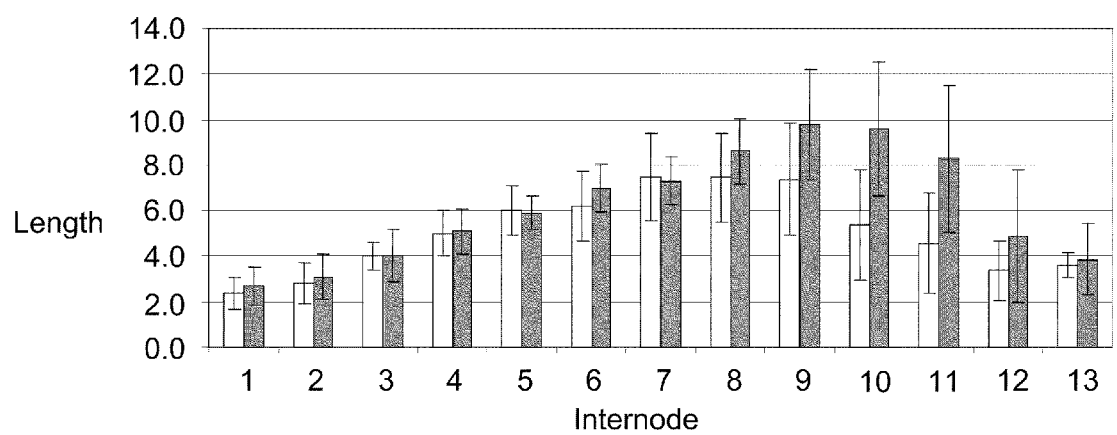

FIG. 10 demonstrates how the increased soybean plant height that is characteristic of G1988 overexpression in short day periods (10 hours light, 14 hours dark) is largely due to an increased in internode length in the upper portion of the plant. The most readily observable differences between a transgenic line and a control line were observed for internodes 8 through 12. The differences in plant height between G1988 transgenic plants and controls were thus accentuated late in the growing season. The control untransformed line used in these experiments is represented by the unshaded bars. The shaded bars show the internode length (in centimeters) of overexpressor line 178.

Figure 11:
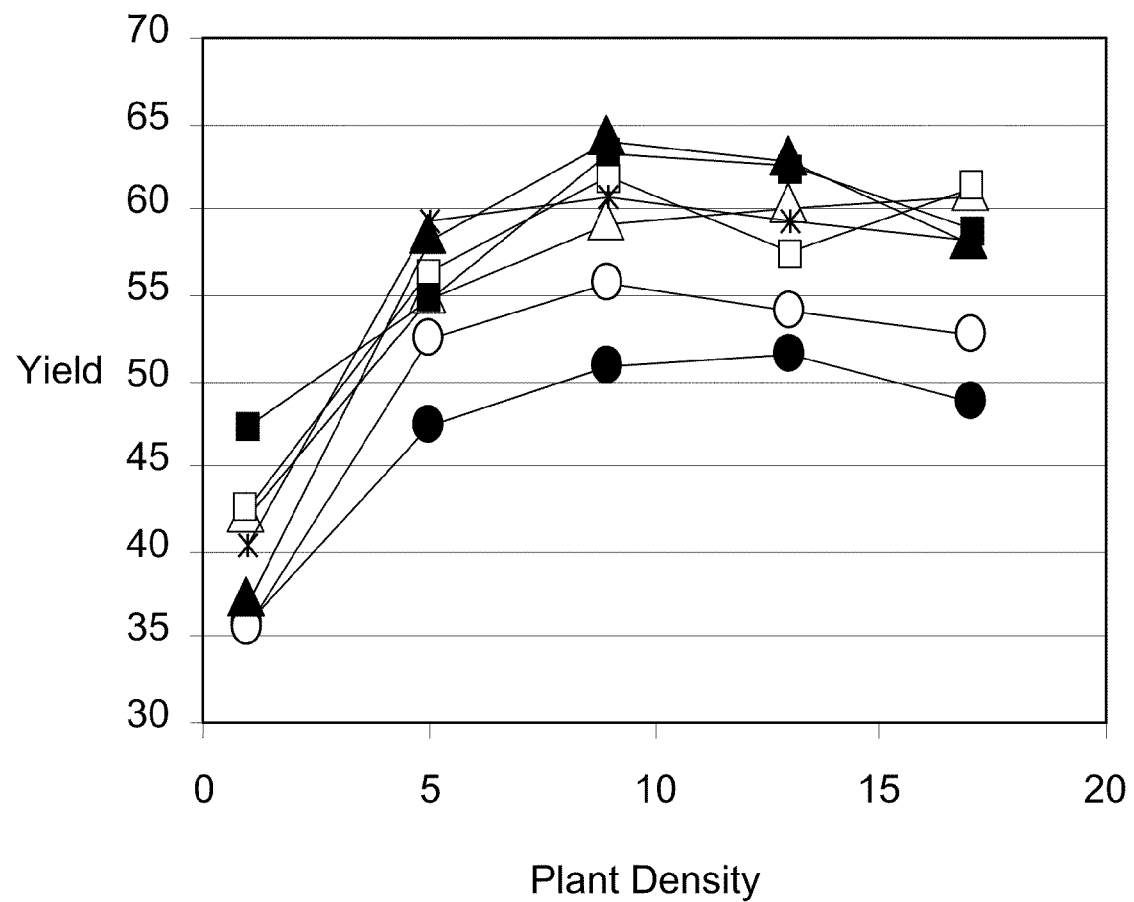

FIG. 11 shows the results of a plant density field trial. As seen in this figure, soybean plants overexpressing G1988 demonstrated an observable yield increase across a range of plant densities, relative to control plants that either did not overexpress G1988 (unfilled circles), or Line 217 transgenic plants that expressed G1988 to a lower degree (about 40% lower) than high yielding transgenic lines (filled circles). Plant stand count did not have large contribution to harvestable yield. Overexpressor line 178 plants are represented by unfilled triangles. Overexpressor line 189 plants are represented by filled triangles. Overexpressor line 209 plants are represented by unfilled squares. Overexpressor line 200 plants are represented by filled squares. Overexpressor line 213 plants are represented by asterisks.

Figure 12:
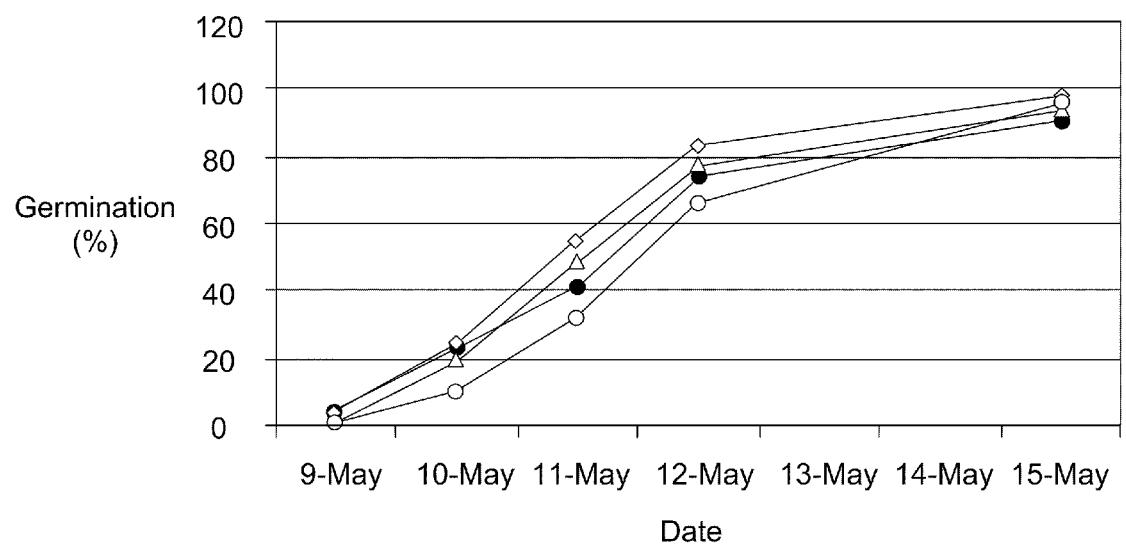

FIG. 12 illustrates that the constitutive overexpression of G1988 (SEQ ID NO: 2) in soy plants promotes germination. Transgenic plants overexpressing G1988 that had been shown to increase yield in soy (line 218, unfilled diamonds; and line 178, unfilled triangles) generally demonstrated a percentage germination above line 217, which expressed G1988 to a lower degree than high yielding transgenic lines (filled circles) and untransformed control plants (unfilled circles). Seeds in these experiments were germinated in 1.0 µM gibberellic acid.

DETAILED DESCRIPTION

The present invention relates to polynucleotides and polypeptides for modifying phenotypes of plants, particularly those associated with increased abiotic stress tolerance and increased yield with respect to a control plant (for example, a wild-type plant). Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

DEFINITIONS

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al. (1976)). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. Alignments such as those of FIGS. 4A-4F may be used to identify conserved domains and relatedness within these domains. An alignment may suitably be determined by means of computer programs known in the art, such as MACVECTOR software (1999) (Accelrys, Inc., San Diego, Calif.).

A "conserved domain" or "conserved region" as used herein refers to a region in heterologous polynucleotide or polypeptide sequences where there is a relatively high degree of sequence identity between the distinct sequences. A "B-box zinc finger" domain", such as is found in a polypeptide member of B-box zinc finger family, is an example of a conserved domain. With respect to polynucleotides encoding presently disclosed polypeptides, a conserved domain is preferably at least nine base pairs (bp) in length. A conserved domain with respect to presently disclosed polypeptides refers to a domain within a polypeptide family that exhibits a higher degree of sequence homology, such as at least about 56% sequence identity, or at least about 58% sequence identity, or at least about 60% sequence identity, or at least about 65%, or at least about 67%, or at least about 70%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%, amino acid residue sequence identity, to a conserved domain of a polypeptide of the invention (e.g., any of SEQ ID NOs: 45-56). Sequences that possess or encode for conserved domains that meet these criteria of percentage identity, and that have comparable biological activity to the present polypeptide sequences, thus being members of the G1988 Glade polypeptides, are encompassed by the invention. A fragment or domain can be referred to as outside a conserved domain, outside a consensus sequence, or outside a consensus DNA-binding site that is known to exist or that exists for a particular polypeptide class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al. (2000a, 2000b)). Thus, by using alignment methods well known in the art, the conserved domains of the plant polypeptides, for example, for the B-box zinc finger proteins (Putterill et al. (1995)), may be determined.

The conserved domains for many of the polypeptide sequences of the invention are listed in Table 1. Also, the polypeptides of Table 1 have conserved domains specifically indicated by amino acid coordinate start and stop sites. A comparison of the regions of these polypeptides allows one of skill in the art (see, for example, Reeves and Nissen (1990, 1995)) to identify domains or conserved domains for any of the polypeptides listed or referred to in this disclosure.

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al. (1985), Sambrook et al. (1989), and by Haymes et al. (1985), which references are incorporated herein by reference.

In general, stringency is determined by the temperature, ionic strength, and concentration of denaturing agents (e.g., formamide) used in a hybridization and washing procedure (for a more detailed description of establishing and determining stringency, see the section "Identifying Polynucleotides or Nucleic Acids by Hybridization", below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known related polynucleotide sequences. Numerous variations are possible in the conditions and means by which nucleic acid hybridization can be performed to isolate related polynucleotide sequences having similarity to sequences known in the art and are not limited to those explicitly disclosed herein. Such an approach may be used to isolate polynucleotide sequences having various degrees of similarity with disclosed polynucleotide sequences, such as, for example, encoded transcription factors having 56% or greater identity with the conserved domains of disclosed sequences.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent polypeptides. Thus, it will be readily appreciated by those of skill in the art, that any of a variety of polynucleotide sequences is capable of encoding the polypeptides and homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840, 544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the polynucleotides listed in the Sequence Listing. Exemplary fragments also include fragments that comprise a region that encodes an conserved domain of a polypeptide. Exemplary fragments also include fragments that comprise a conserved domain of a polypeptide. Exemplary fragments include fragments that comprise an conserved domain of a polypeptide, for example, amino acid residues 5-50 of G1988 (SEQ ID NO: 2), amino acid residues 6-51 of G4004 (SEQ ID NO: 4) or amino acid residues 6-51 of G4005 (SEQ ID NO: 6).

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The invention also encompasses production of DNA sequences that encode polypeptides and derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding polypeptides or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, FIG. 1, adapted from Daly et al. (2001), FIG. 2, adapted from Ku et al. (2000); and see also Tudge (2000).

A "control plant" as used in the present invention refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present invention that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the controlled expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a polypeptide's expression is altered, e.g., in that it has been knocked out, overexpressed, or ectopically expressed.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular polypeptide in a suspension cell is the expression levels of a set of genes in a cell knocking out or overexpressing that polypeptide compared with the expression levels of that same set of genes in a suspension cell that has normal levels of that polypeptide. The transcript profile can be presented as a list of those genes whose expression level is significantly different between the two treatments, and the difference ratios. Differences and similarities between expression levels may also be evaluated and calculated using statistical and clustering methods.

With regard to gene knockouts as used herein, the term "knockout" refers to a plant or plant cell having a disruption in at least one gene in the plant or cell, where the disruption results in a reduced expression or activity of the polypeptide encoded by that gene compared to a control cell. The knockout can be the result of, for example, genomic disruptions, including transposons, tilling, and homologous recombination, antisense constructs, sense constructs, RNA silencing constructs, or RNA interference. A T-DNA insertion within a gene is an example of a genotypic alteration that may abolish expression of that gene.

"Ectopic expression or altered expression" in reference to a polynucleotide indicates that the pattern of expression in, e.g., a transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more polypeptides are under the control of a strong promoter (e.g., the cauliflower mosaic virus 35S transcription initiation region). Overexpression may also under the control of an inducible or tissue specific promoter. Thus, overexpression may occur throughout a plant, in specific tissues of the plant, or in the presence or absence of particular environmental signals, depending on the promoter used.

Overexpression may take place in plant cells normally lacking expression of polypeptides functionally equivalent or identical to the present polypeptides. Overexpression may also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors possess an conserved domain. The transcription factors also comprise an amino acid subsequence that forms a transcription activation domain that regulates expression of one or more abiotic stress tolerance genes in a plant when the transcription factor binds to the regulating region.

"Yield" or "plant yield" refers to increased plant growth, increased crop growth, increased biomass, and/or increased plant product production, and is dependent to some extent on temperature, plant size, organ size, planting density, light, water and nutrient availability, and how the plant copes with various stresses, such as through temperature acclimation and water or nutrient use efficiency.

"Planting density" refers to the number of plants that can be grown per acre. For crop species, planting or population density varies from a crop to a crop, from one growing region to another, and from year to year. Using corn as an example, the average prevailing density in 2000 was in the range of 20,000-25,000 plants per acre in Missouri, USA. A desirable higher population density (a measure of yield) would be at least 22,000 plants per acre, and a more desirable higher population density would be at least 28,000 plants per acre, more preferably at least 34,000 plants per acre, and most preferably at least 40,000 plants per acre. The average prevailing densities per acre of a few other examples of crop plants in the USA in the year 2000 were: wheat 1,000,000-1,500,000; rice 650,000-900,000; soybean 150,000-200,000, canola 260,000-350,000, sunflower 17,000-23,000 and cotton 28,000-55,000 plants per acre (Cheikh et al. (2003) U.S. Patent Application No. 20030101479). A desirable higher population density for each of these examples, as well as other valuable species of plants, would be at least 10% higher than the average prevailing density or yield.

DESCRIPTION OF THE SPECIFIC EMBODIMENTS

Transcription Factors Modify Expression of Endogenous Genes

A transcription factor may include, but is not limited to, any polypeptide that can activate or repress transcription of a single gene or a number of genes. As one of ordinary skill in the art recognizes, transcription factors can be identified by the presence of a region or domain of structural similarity or identity to a specific consensus sequence or the presence of a specific consensus DNA-binding motif (see, for example, Riechmann et al. (2000a)). The plant transcription factors of the present invention belong to the B-box zinc finger family (Putterill et al. (1995)) and are putative transcription factors.

Generally, transcription factors are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to osmotic stresses. The sequences of the invention may also be used to transform a plant and introduce desirable traits not found in the wild-type cultivar or strain. Plants may then be selected for those that produce the most desirable degree of over- or under-expression of target genes of interest and coincident trait improvement.

The sequences of the present invention may be from any species, particularly plant species, in a naturally occurring form or from any source whether natural, synthetic, semi-synthetic or recombinant. The sequences of the invention may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

Expression of genes that encode polypeptides that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) and Peng et al. (1999). In addition, many others have demonstrated that an Arabidopsis transcription factor expressed in an exogenous plant species elicits the same or very similar phenotypic response. See, for example, Fu et al. (2001); Nandi et al. (2000); Coupland (1995); and Weigel and Nilsson (1995)).

In another example, Mandel et al. (1992b), and Suzuki et al. (2001), teach that a transcription factor expressed in another plant species elicits the same or very similar phenotypic response of the endogenous sequence, as often predicted in earlier studies of *Arabidopsis* transcription factors in *Arabidopsis* (see Mandel et al. (1992a); Suzuki et al. (2001)). Other examples include Müller et al. (2001); Kim et al. (2001); Kyozuka and Shimamoto (2002); Boss and Thomas (2002); He et al. (2000); and Robson et al. (2001).

In yet another example, Gilmour et al. (1998) teach an *Arabidopsis* AP2 transcription factor, CBF1, which, when overexpressed in transgenic plants, increases plant freezing tolerance. Jaglo et al. (2001) further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus*, wheat, rye, and tomato revealed the presence of conserved consecutive amino acid residues, PKK/RPAGRxKFxETRHP (SEQ ID NO: 69) and DSAWR (SEQ ID NO: 70), which bracket the AP2/EREBP DNA binding domains of the proteins and distinguish them from other members of the AP2/EREBP protein family. (Jaglo et al. (2001))

Transcription factors mediate cellular responses and control traits through altered expression of genes containing cis-acting nucleotide sequences that are targets of the introduced transcription factor. It is well appreciated in the art that the effect of a transcription factor on cellular responses or a cellular trait is determined by the particular genes whose expression is either directly or indirectly (e.g., by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene and other genes in the MYB family have been shown to control anthocyanin biosynthesis through regulation of the expression of genes known to be involved in the anthocyanin biosynthetic pathway (Bruce et al. (2000); and Borevitz et al. (2000)). Further, global transcript profiles have been used successfully as diagnostic tools for specific cellular states (e.g., cancerous vs. non-cancerous; Bhattacharjee et al. (2001); and Xu et al. (2001)). Consequently, it is evident to one skilled in the art that similarity of transcript profile upon overexpression of different transcription factors would indicate similarity of transcription factor function.

Polypeptides and Polynucleotides of the Invention

The present invention includes putative transcription factors (TFs), and isolated or recombinant polynucleotides encoding the polypeptides, or novel sequence variant polypeptides or polynucleotides encoding novel variants of polypeptides derived from the specific sequences provided in the Sequence Listing; the recombinant polynucleotides of the invention may be incorporated in expression vectors for the purpose of producing transformed plants. Also provided are methods for modifying yield from a plant by modifying the mass, size or number of plant organs or seed of a plant by controlling a number of cellular processes, and for increasing a plant's resistance to abiotic stresses. These methods are based on the ability to alter the expression of critical regulatory molecules that may be conserved between diverse plant species. Related conserved regulatory molecules may be originally discovered in a model system such as *Arabidopsis* and homologous, functional molecules then discovered in other plant species. The latter may then be used to confer increased yield or abiotic stress tolerance in diverse plant species.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known polypeptides. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known polypeptides.

Additional polynucleotides of the invention were identified by screening *Arabidopsis thaliana* and/or other plant cDNA libraries with probes corresponding to known polypeptides under low stringency hybridization conditions. Additional sequences, including full length coding sequences, were subsequently recovered by the rapid amplification of cDNA ends (RACE) procedure using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

Many of the sequences in the Sequence Listing, derived from diverse plant species, have been ectopically expressed in overexpressor plants. The changes in the characteristic(s) or trait(s) of the plants were then observed and found to confer increased yield and/or increased abiotic stress tolerance. Therefore, the polynucleotides and polypeptides can be used to improve desirable characteristics of plants.

The polynucleotides of the invention were also ectopically expressed in overexpressor plant cells and the changes in the expression levels of a number of genes, polynucleotides, and/ or proteins of the plant cells observed. Therefore, the polynucleotides and polypeptides can be used to change expression levels of genes, polynucleotides, and/or proteins of plants or plant cells.

The data presented herein represent the results obtained in experiments with polynucleotides and polypeptides that may be expressed in plants for the purpose of reducing yield losses that arise from biotic and abiotic stress.

Background Information for G1988, the G1988 Glade, and related sequences

G1988 belongs to the CONSTANS-like family of zinc finger proteins, which was defined based on a Zn-finger domain known as the B-box. The B-box has homology to a protein-protein interaction domain found in animal transcription factors (Robson et al., 2001; Borden, 1998; Torok and Etkin, 2001) and the B-domain of G1988 and its close homolog Glade members functions in the same protein-protein interaction capacity. The CONSTANS-like proteins contain one or two N-terminal B-box motifs (the G1988 Glade contains a single N-terminal B-box domain). G1988 and its homologs from other species share conserved C-terminal motifs that define a clear Glade that is distinct from other B-box proteins, and generally contain the signature residues identified by the triangles in FIGS. 4D and 4E, and by SEQ ID NOs: 62, 57, and 58. G1988 is expressed in many tissues. G1988 and its homologs are diurnally regulated As disclosed below in the Examples, constitutive expression of G1988 in *Arabidopsis* modulates diverse plant growth processes, including elongation of hypocotyls, extended petioles and upheld leaves, early flowering; enhanced root and/or shoot growth in phosphate-limited media; more secondary roots on control media, enhanced growth and reduced anthocyanin in low nitrogen/high sucrose media supplemented with glutamine, enhanced root growth on salt-containing media, and enhanced root growth on polyethylene glycol-containing media, as compared to control plants. G1988 overexpression in soybean plants has been shown to result in a statistically significant increase in yield in field trials (see FIG. 6 and Examples presented below) as compared to parental line controls.

The G1988 Glade includes a number of sequences descended from a common ancestral sequence, as shown in the phylogenetic tree seen in FIG. 3. The ancestral sequence is represented by the node of the tree indicated by the arrow in FIG. 3 having a bootstrap value of 74. Examples of Glade members include those sequences within the box and bounded by G4011 and G4009 in FIG. 3. Polypeptide members of the G1988 Glade examined to date, including G1988 and phylogenetically-related sequences from diverse species, comprise several characteristic structural features, including a highly conserved B-domain, indicated in FIGS. 4A and 4B, and several characteristic or signature residues outside of and nearer to the C-terminus than the B-domain. Signature residues are indicated by the small dark triangles in FIGS. 4D and 4E. These residues comprise, in order from N to C termini:

$W-X_4-G$
(SEQ ID NO: 62, where X represents any amino acid; seen in FIG. 4D)

$R-X_3-A-X_3-W$
(SEQ ID NO: 57, where X represents any amino acid; seen in FIG. 4D)

followed by:

EGWXE
(SEQ ID NO: 58; where X represents any amino acid; seen in FIG. 4E).

Thus, a G1988 Glade sequence may be defined as having a highly conserved B-domain at least 56% identical in its amino acid sequence to SEQ ID NO: 45. G1988 Glade members examined thus far may be further defined by having amino acid residues characterized by a tryptophan residue and a glycine residue at the positions corresponding to the first and fifth residues shown in FIG. 4D nearer the C-terminus than said B-domain, and/or by having SEQ ID NO: 57 nearer the C-terminus than said tryptophan residue, and/or by having SEQ ID NO: 58 nearer the C-terminus than SEQ ID NO: 57.

It is likely that the ectopic expression of G1988 product can affect light signaling, or downstream hormonal pathways. Based upon the observations described above, G1988 appears to be involved in photomorphogenesis and plant growth and development. Hence, its overexpression may improve plant vigor, thus explaining the yield enhancements seen in 35S:: G1988 soybean plants as noted below.

A number of sequences have been found in other plant species that are closely-related to G1988. Table 1 shows a number of polypeptides of the invention and includes the SEQ ID NO: (Column 1), the species from which the sequence was derived and the Gene Identifier ("GID"; Column 2), the percent identity of the polypeptide in Column 1 to the full length G1988 polypeptide, SEQ ID NO: 1, as determined by a BLASTp analysis with a wordlength (W) of 3, an expectation (E) of 10, and the BLOSUM62 scoring matrix Henikoff & Henikoff (1989, 1991) (Column 3), the amino acid residue coordinates for the conserved B-box ZF domains, in amino acid coordinates beginning at the n-terminus, of each of the sequences (Column 4), the conserved B-box ZF domain sequences of the respective polypeptides (Column 5); the SEQ ID NO: of each of the B-box ZF domains (Column 6), and the percentage identity of the conserved domain in Column 5 to the conserved domain of the *Arabidopsis* G1988 sequence, SEQ ID NO: 45 (Column 7).

TABLE 1

Conserved domains of G1988 and closely related sequences

| Column 1 Polypeptide SEQ ID NO: | Column 2 Species/ GID No. | Column 3 Percent identity of polypeptide in Column 1 to G1988 | Column 4 B-box Z domain in amino acid coordinates | Column 5 B-box ZF domain | Column 6 SEQ ID NO: of B-box ZF domain | Column 7 Percent identity of B-box ZF domain in Column 5 to conserved domain of G1988 |
|---|---|---|---|---|---|---|
| 2 | At/G1988 | 100% | 5-50 | CELCGAEADLHC AADSAFLCRSCD AKFHASNFLFAR HFRRVICPNC | 45 | 100% |
| 18 | Zm/G4297 | 30% | 14-55 | CELCGGAAAVH CAADSAFLCPRC DAKVHGANFLA SRHVRRRL | 53 | 70% |
| 24 | Zm/G4001 | 30% | 20-61 | CELCGGAAAVH CAADSAFLCLRC DAKVHGANFLA SRHVRRRL | 56 | 70% |
| 16 | Os/G4012 | 32% | 15-56 | CELCGGVAAVH CAADSAFLCLVC DDKVHGANFLA SRHRRRRL | 52 | 67% |
| 20 | Os/G4298 | 67% | 15-55 | CELCGGVAAVH CAADSAFLCLVC DDKVHGANFLA SRHPRRR | 54 | 67% |
| 14 | Os/G4011 | 33% | 8-49 | CALCGAAAAVH CEADAAFLCAA CDAKVHGANFL ASRHHRRRV | 51 | 65% |
| 8 | Zm/G4000 | 30% | 20-61 | CELCGGAAAVH CAADSAFLCLRC DAKVHGANFLA SRHVRRRL | 48 | 65% |
| 66 | Ta/Ta1988 | 33% | 13-54 | CELCGGVAAVH CAADSAFLCVPC DAKVHGANFLA SRHLRRRL | 68 | 61% |
| 4 | Gm/G4004 | 33% | 6-51 | CELCHQLASLYC PSDSAFLCFHCD AAVHAANFLVA RHLRRLLCSKC | 46 | 60% |
| 6 | Gm/G4005 | 32% | 6-51 | CELCDQQASLYC PSDSAFLCSDCD AAVHAANFLVA RHLRRLLCSKC | 47 | 60% |
| 10 | Ct/G4007 | 45% | 5-50 | CELCSQEAALHC ASDEAFLCFDCD DRVHKANFLVA RHVRQTLCSQC | 49 | 58% |

TABLE 1-continued

Conserved domains of G1988 and closely related sequences

| Column 1 Polypeptide SEQ ID NO: | Column 2 Species/ GID No. | Column 3 Percent identity of polypeptide in Column 1 to G1988 | Column 4 B-box Z domain in amino acid coordinates | Column 5 B-box ZF domain | Column 6 SEQ ID NO: of B-box ZF domain | Column 7 Percent identity of B-box ZF domain in Column 5 to conserved domain of G1988 |
|---|---|---|---|---|---|---|
| 22 | Le/G4299 | 36% | 9-54 | CELCNDQAALFC PSDSAFLCFHCD AKVHQANFLVA RHLRLTLCSHC | 55 | 58% |
| 12 | Pt/G4009 | 40% | 6-51 | CELCKGEAGVY CDSDAAYLCFDC DSNVHNANFLV ARHIRRVICSGC | 50 | 56% |

Species abbreviations for Table 1: At - *Arabidopsis thaliana*; Ct - *Citrus sinensis*; Gm - *Glycine max*; Le - *Lycopersicon esculenturn*; Os - *Oryza sativa*; Pt - *Populus trichocarpa*; Ta - *Triticum aestivum*; Zm - *Zea mays*.
[1]phenotype observed in both *Arabidopsis* and soy plants Tables 2 and 3 list some of the morphological and physiological traits that conferred to *Arabidopsis*, soy or corn plants overexpressing G1988 or orthologs from diverse species of plants, including *Arabidopsis*, soy, may, rice, and tomato, in experiments conducted to date. All observations are made with respect to control plants that did not overexpress a G1988 Glade transcription factor.

TABLE 2

G1988 homologs and potentially valuable morphology-related traits

| Col. 1 GID (SEQ ID No.) Species | Col. 2 Reduced light response: elongated hypocotyls, elongated petioles or upright leaves | Col. 3 Increased yield* | Col. 4 Increased secondary roots | Col. 5 Delayed development and/or time to flowering |
|---|---|---|---|---|
| G1988 (2) At | +[1] | +[3] | +[1] | +[1,3] |
| G4004 (4) Gm | +[1] | n/d | n/d | +[1] |
| G4005 (6) Gm | +[1] | n/d | n/d | +[1] |
| G4000 (8) Zm | +[1] | n/d | n/d | +[1] |
| G4012 (16) Os | +[1] | n/d | n/d | +[1] |
| G4299 (22) Sl | +[1] | n/d | n/d | +[1] |

*yield may be increased by morphological improvements and/or increased tolerance to various physiological stresses

TABLE 3

G1988 homologs and potentially valuable physiological traits

| Col. 1 GID (SEQ ID No.) Species | Col. 2 Better germination in cold conditions | Col. 3 Increased water deprivation tolerance | Col. 4 Altered C/N sensing or low N tolerance | Col. 5 Increased low P tolerance | Col. 6 Increased hyperosmotic stress (sucrose) tolerance |
|---|---|---|---|---|---|
| G1988 (2) At | +[3] | +[1,3] | +[1] | +[1] | +[1] |
| G4004 (4) Gm | +[1,2,3] | n/d | +[1,2] | −[1] | |
| G4005 (6) Gm | −[1] | | +[1] | | −[1] |
| G4000 (8) Zm | n/d | n/d | n/d | n/d | n/d |

TABLE 3-continued

G1988 homologs and potentially valuable physiological traits

| Col. 1 GID (SEQ ID No.) Species | Col. 2 Better germination in cold conditions | Col. 3 Increased water deprivation tolerance | Col. 4 Altered C/N sensing or low N tolerance | Col. 5 Increased low P tolerance | Col. 6 Increased hyperosmotic stress (sucrose) tolerance |
|---|---|---|---|---|---|
| G4012 (16) Os | n/d | n/d | n/d | n/d | n/d |
| G4299 (22) Sl | n/d | n/d | n/d | n/d | n/d |

Species abbreviations for Tables 2 and 3:
At—*Arabidopsis thaliana*;
Gm—*Glycine max*;
Os—*Oryza sativa*;
Sl—*Solanum lycopersicum*;
Zm—*Zea mays*
(+) indicates positive assay result/more tolerant or phenotype observed, relative to controls. (−) indicates negative assay result/less tolerant or phenotype observed, relative to controls
empty cell - assay result similar to controls
[1] phenotype observed in *Arabidopsis* plants
[2] phenotype observed in maize plants
[3] phenotype observed in soy plants
n/d - assay not yet done or completed
N - Altered C/N sensing or low nitrogen tolerance
P—phosphorus Water deprivation tolerance was indicated in soil-based drought or plate-based desiccation assays Hyperosmotic stress was indicated by greater tolerance to 9.4% sucrose than controls Increased cold tolerance was indicated by greater tolerance to 8° C. during germination or growth than controls Altered C/N sensing or low nitrogen tolerance assays were conducted in basal media minus nitrogen plus 3% sucrose or basal media minus nitrogen plus 3% sucrose and 1 mM glutamine; for the nitrogen limitation assay, the nitrogen source of 80% MS medium was reduced to 20 mg/L of $NH_4NO_3$.

Increased low P tolerance was indicated by better growth in MS medium lacking a phosphorus source A reduced light sensitivity phenotype was indicated by longer petioles, longer hypocotyls and/or upturned leaves relative to control plants n/d—assay not done or completed Orthologs and Paralogs Homologous sequences as described above can comprise orthologous or paralogous sequences. Several different methods are known by those of skill in the art for identifying and defining these functionally homologous sequences. General methods for identifying orthologs and paralogs, including phylogenetic methods, sequence similarity and hybridization methods, are described herein; an ortholog or paralog, including equivalogs, may be identified by one or more of the methods described below.

As described by Eisen (1998) *Genome Res.* 8: 163-167, evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (i.e., by evolutionary processes) rather than on the sequence similarity itself (Eisen, supra). In fact, many specific examples exist in which gene function has been shown to correlate well with gene phylogeny (Eisen, supra). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships . . . . After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, supra).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same Glade (a group of similar genes) when a gene family phylogeny is analyzed using programs such as CLUSTAL (Thompson et al. (1994); Higgins et al. (1996)). Groups of similar genes can also be identified with pair-wise BLAST analysis (Feng and Doolittle (1987)). For example, a Glade of very similar MADS domain transcription factors from *Arabidopsis* all share a common function in flowering time (Ratcliffe et al. (2001)), and a group of very similar AP2 domain transcription factors from *Arabidopsis* are involved in tolerance of plants to freezing (Gilmour et al. (1998)). Analysis of groups of similar genes with similar function that fall within one Glade can yield sub-sequences that are particular to the Glade. These sub-sequences, known as consensus sequences, can not only be used to define the sequences within each Glade, but define the functions of these genes; genes within a Glade may contain paralogous sequences, or orthologous sequences that share the same function (see also, for example, Mount (2001))

Transcription factor gene sequences are conserved across diverse eukaryotic species lines (Goodrich et al. (1993); Lin et al. (1991); Sadowski et al. (1988)). Plants are no exception to this observation; diverse plant species possess transcription factors that have similar sequences and functions. Speciation, the production of new species from a parental species, gives rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994); Higgins et al. (1996)) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

By using a phylogenetic analysis, one skilled in the art would recognize that the ability to deduce similar functions conferred by closely-related polypeptides is predictable. This predictability has been confirmed by our own many studies in which we have found that a wide variety of polypeptides have orthologous or closely-related homologous sequences that function as does the first, closely-related reference sequence. For example, distinct transcription factors, including:

(i) AP2 family *Arabidopsis* G47 (found in U.S. Pat. No. 7,135,616), a phylogenetically-related sequence from soybean, and two phylogenetically-related homologs from rice all can confer greater tolerance to drought, hyperosmotic stress, or delayed flowering as compared to control plants;

(ii) CAAT family *Arabidopsis* G481 (found in PCT patent publication WO2004076638), and numerous phylogenetically-related sequences from eudicots and monocots can confer greater tolerance to drought-related stress as compared to control plants;

(iii) Myb-related *Arabidopsis* G682 (found in U.S. Pat. Nos. 7,223,904 and 7,193,129) and numerous phylogenetically-related sequences from eudicots and monocots can confer greater tolerance to heat, drought-related stress, cold, and salt as compared to control plants;

(iv) WRKY family *Arabidopsis* G1274 (found in U.S. Pat. No. 7,196,245) and numerous closely-related sequences from eudicots and monocots have been shown to confer increased water deprivation tolerance, and (v) AT-hook family soy sequence G3456 (found in US patent publication 20040128712A1) and numerous phylogenetically-related sequences from eudicots and monocots, increased biomass compared to control plants when these sequences are overexpressed in plants.

The polypeptides sequences belong to distinct clades of polypeptides that include members from diverse species. In each case, most or all of the clade member sequences derived from both eudicots and monocots have been shown to confer increased yield or tolerance to one or more abiotic stresses when the sequences were overexpressed. These studies each demonstrate that evolutionarily conserved genes from diverse species are likely to function similarly (i.e., by regulating similar target sequences and controlling the same traits), and that polynucleotides from one species may be transformed into closely-related or distantly-related plant species to confer or improve traits.

As shown in Table 1, polypeptides that are phylogenetically related to the polypeptides of the invention may have conserved domains that share at least 56%, 58%, 60%, 65%, 67%, or 70%, 75%, 80%, 85%, 90%, or 95% amino acid sequence identity, and have similar functions in that the polypeptides of the invention may, when overexpressed, confer at least one regulatory activity selected from the group consisting of greater yield, more rapid growth, greater size, increased secondary rooting, greater cold tolerance, greater tolerance to water deprivation, reduced stomatal conductance, altered C/N sensing or increased low nitrogen tolerance, increased low phosphorus tolerance, increased tolerance to hyperosmotic stress, and/or reduced light sensitivity as compared to a control plant.

At the nucleotide level, the sequences of the invention will typically share at least about 30% or 40% nucleotide sequence identity, preferably at least about 50%, about 60%, about 70% or about 80% sequence identity, and more preferably about 85%, about 90%, about 95% or about 97% or more sequence identity to one or more of the listed full-length sequences, or to a listed sequence but excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded protein.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp (1988). The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Software for performing BLAST analyses is publicly available, e.g., through the National Center for Biotechnology Information (see interne website at http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990); Altschul et al. (1993)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0).

For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989, 1991)). Unless otherwise indicated for comparisons of predicted polynucleotides, "sequence identity" refers to the % sequence identity generated from a tblastx using the NCBI version of the algorithm at the default settings using gapped alignments with the filter "off" (see, for example, internet website at http://www.ncbi.nlm.nih.gov/).

Other techniques for alignment are described by Doolittle (1996). Preferably, an alignment program that permits gaps in the sequence is utilized to align the sequences. The Smith-Waterman is one type of algorithm that permits gaps in sequence alignments (see Shpaer (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method (see, for example, Hein (1990)) Identity between sequences can also be determined by other methods known in the art, e.g., by varying hybridization conditions (see US Patent Application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al. (1997)), PFAM, and other databases which contain previously identified and annotated motifs, sequences and gene functions. Methods that search for primary sequence patterns with secondary structure gap penalties (Smith et al. (1992)) as well as algorithms such as Basic Local Alignment Search Tool (BLAST; Altschul (1990); Altschul et al. (1993)), BLOCKS (Henikoff and Henikoff (1991)), Hidden Markov Models (HMM; Eddy (1996); Sonnhammer et al. (1997)), and the like, can be used to manipulate and analyze polynucleotide and polypeptide sequences encoded by polynucleotides. These databases, algorithms and other methods are well known in the art and are described in Ausubel et al. (1997), and in Meyers (1995).

A further method for identifying or confirming that specific homologous sequences control the same function is by comparison of the transcript profile(s) obtained upon overexpression or knockout of two or more related polypeptides. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler and Thomashow (2002), have shown that three paralogous AP2 family genes (CBF1, CBF2 and CBF3) are induced upon cold treatment, and each of which can condition improved freezing tolerance, and all have highly similar transcript profiles. Once a polypeptide has been shown to provide a specific function, its transcript profile becomes a diagnostic tool to determine whether paralogs or orthologs have the same function.

Furthermore, methods using manual alignment of sequences similar or homologous to one or more polynucleotide sequences or one or more polypeptides encoded by the polynucleotide sequences may be used to identify regions of similarity and B-box zinc finger domains. Such manual methods are well-known of those of skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed polypeptides may be cloned using compositions provided by the present invention according to methods well known in the art. cDNAs can be cloned using mRNA from a plant cell or tissue that expresses one of the present sequences. Appropriate mRNA sources may be identified by interrogating Northern blots with probes designed from the present sequences, after which a library is prepared from the mRNA obtained from a positive cell or tissue. Polypeptide-encoding cDNA is then isolated using, for example, PCR, using primers designed from a presently disclosed gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of orthologs of the *Arabidopsis* polypeptide sequences and their functionally similar orthologs are listed in Table 1 and the Sequence Listing. In addition to the sequences in Table 1 and the Sequence Listing, the invention encompasses isolated nucleotide sequences that are phylogenetically and structurally similar to sequences listed in the Sequence Listing) and can function in a plant by increasing yield and/or and abiotic stress tolerance when ectopically expressed in a plant.

Since a significant number of these sequences are phylogenetically and sequentially related to each other and have been shown to increase yield from a plant and/or abiotic stress tolerance, one skilled in the art would predict that other similar, phylogenetically related sequences falling within the present clades of polypeptides would also perform similar functions when ectopically expressed.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited below (e.g., Sambrook et al. (1989); Berger and Kimmel (1987); and Anderson and Young (1985)).

Encompassed by the invention are polynucleotide sequences that are capable of hybridizing to the claimed polynucleotide sequences, including any of the polynucleotides within the Sequence Listing, and fragments thereof under various conditions of stringency (see, for example, Wahl and Berger (1987); and Kimmel (1987)). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art. See, for example, Sambrook et al. (1989); Berger (1987), pages 467-469; and Anderson and Young (1985).

Stability of DNA duplexes is affected by such factors as base composition, length, and degree of base pair mismatch. Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

(I) DNA-DNA:

$$T_m(° C.)=81.5+16.6(\log [Na+])+0.41(\% G+C)-0.62(\% \text{ formamide})-500/L$$

(II) DNA-RNA:

$$T_m(° C.)=79.8+18.5(\log [Na+])+0.58(\% G+C)+0.12(\% G+C)^2-0.5(\% \text{ formamide})-820/L$$

(III) RNA-RNA:

$$T_m(° C.)=79.8+18.5(\log [Na+])+0.58(\% G+C)+0.12(\% G+C)^2-0.35(\% \text{ formamide})-820/L$$

where L is the length of the duplex formed, [Na+] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson and Young (1985)). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guidelines high stringency is typically performed at $T_m$-5° C. to $T_m$-20° C., moderate stringency at $T_m$-20° C. to $T_m$-35° C. and low stringency at $T_m$-35° C. to $T_m$-50° C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m$-25° C. for DNA-DNA duplex and $T_m$-15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or Northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present polypeptides include, for example:

6×SSC at 65° C.;
50% formamide, 4×SSC at 42° C.; or
0.5×SSC, 0.1% SDS at 65° C.;

with, for example, two wash steps of 10-30 minutes each. Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl, with 1.5 mM trisodium citrate, and 0.1% SDS over 30 minutes. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (see, for example, US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a polypeptide known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences that are capable of hybridizing to the claimed polynucleotide sequences, including any of the polynucleotides within the Sequence Listing, and fragments thereof under various conditions of stringency (see, for example, Wahl and Berger (1987), pages 399-407; and Kimmel (1987)). In addition to the nucleotide sequences in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

EXAMPLES

It is to be understood that this invention is not limited to the particular devices, machines, materials and methods described. Although particular embodiments are described, equivalent embodiments may be used to practice the invention.

The invention, now being generally described, will be more readily understood by reference to the following examples, which are included merely for purposes of illustration of certain aspects and embodiments of the present invention and are not intended to limit the invention. It will be recognized by one of skill in the art that a polypeptide that is associated with a particular first trait may also be associated with at least one other, unrelated and inherent second trait which was not predicted by the first trait.

Example I

Project Types and Vector and Cloning Information

A number of constructs were used to modulate the activity of sequences of the invention. An individual project was defined as the analysis of lines for a particular construct (for example, this might include G1988 lines that constitutively overexpressed a sequence of the invention). In the present study, a full-length wild-type version of a gene was directly fused to a promoter that drove its expression in transgenic plants. Such a promoter could be the native promoter of that gene, or a constitutive promoter such as the cauliflower mosaic virus 35S promoter. Alternatively, a promoter that drives tissue specific or conditional expression could be used in similar studies.

In the present study, expression of a given polynucleotide from a particular promoter was achieved by a direct-promoter fusion construct in which that sequence was cloned directly behind the promoter of interest. A direct fusion approach has the advantage of allowing for simple genetic analysis if a given promoter-polynucleotide line is to be crossed into different genetic backgrounds at a later date.

For analysis of G1988-overexpressing plants, transgenic lines were created with the expression vector P2499 (SEQ ID NO: 59), which contained a G1988 cDNA clone. This construct constituted a 35S::G1988 direct promoter-fusion carrying a kanamycin resistance marker and was introduced into *Arabidopsis* plants.

G4004 (polynucleotide SEQ ID NO: 3 and polypeptide SEQ ID NO: 4) is a sequence derived from soybean. G4004 was identified as a closely-related homolog of G1988 based on phylogenetic analysis described above. P26748 (SEQ ID NO: 60) contained a G4004 cDNA clone, and was a 35S::G4004 direct promoter-fusion construct carrying a kanamycin resistance marker. This construct was used to generate lines of transgenic *Arabidopsis* plants constitutively overexpressing the G4004 polypeptide.

G4005 (polynucleotide SEQ ID NO: 5 and polypeptide SEQ ID NO: 6) was also derived from soybean, and was also identified as a closely-related homolog of G1988 based on phylogenetic analysis described above. P26749 (SEQ ID NO: 61) contained a G4005 cDNA clone, and was a 35S::G4005 direct promoter-fusion construct carrying a kanamycin resistance marker. This construct was used to generate lines of transgenic *Arabidopsis* plants constitutively overexpressing the G4005 polypeptide.

A list of constructs (these expression vectors are identified by a "PID" designation provided in the second column) used to created plants overexpressing G1988 Glade members found in this report is provided in Table 4 and in the Sequence Listing.

TABLE 4

Expression constructs used to create plants overexpressing G1988 clade members

| Gene Identifier | Construct (PID) | SEQ ID NO: of PID | Promoter | Project type |
|---|---|---|---|---|
| G1988 (2) At | P2499 | 59 | 35S | Direct promoter-fusion |
| G4004 (4) Gm | P26748 | 60 | 35S | Direct promoter-fusion |
| G4005 (6) Gm | P26749 | 61 | 35S | Direct promoter-fusion |
| G4000 (8) Zm | P27404 | 63 | 35S | Direct promoter-fusion |
| G4012 (16) Os | P27406 | 64 | 35S | Direct promoter-fusion |
| G4299 (22) Sl | P27428 | 65 | 35S | Direct promoter-fusion |

Species abbreviations for Table 4:
At—*Arabidopsis thaliana*;
Gm—*Glycine max*;
Os—*Oryza sativa*;
Sl—*Solanum lycopersicum*;
Zm—*Zea mays*

Example II

Transformation

Transformation of *Arabidopsis* was performed by an *Agrobacterium*-mediated protocol based on the method of Bechtold and Pelletier (1998). Unless otherwise specified, all experimental work was done using the Columbia ecotype.

Plant preparation. *Arabidopsis* seeds were sown on mesh covered pots. The seedlings were thinned so that 6-10 evenly spaced plants remained on each pot 10 days after planting. The primary bolts were cut off a week before transformation to break apical dominance and encourage auxiliary shoots to form. Transformation was typically performed at 4-5 weeks after sowing.

Bacterial culture preparation. *Agrobacterium* stocks were inoculated from single colony plates or from glycerol stocks and grown with the appropriate antibiotics and grown until saturation. On the morning of transformation, the saturated cultures were centrifuged and bacterial pellets were re-suspended in Infiltration Media (0.5×MS, 1× B5 Vitamins, 5% sucrose, 1 mg/ml benzylaminopurine riboside, 200 µl/L Silwet L77) until an A600 reading of 0.8 was reached.

Transformation and seed harvest. The *Agrobacterium* solution was poured into dipping containers. All flower buds and rosette leaves of the plants were immersed in this solution for 30 seconds. The plants were laid on their side and wrapped to keep the humidity high. The plants were kept this way overnight at 4° C. and then the pots were turned upright, unwrapped, and moved to the growth racks.

The plants were maintained on the growth rack under 24-hour light until seeds were ready to be harvested. Seeds were harvested when 80% of the siliques of the transformed plants were ripe (approximately 5 weeks after the initial transformation). This seed was deemed T0 seed, since it was obtained from the T0 generation, and was later plated on selection plates (either kanamycin or sulfonamide). Resistant plants that were identified on such selection plates comprised the T1 generation, from which transgenic seed comprising an expression vector of interest could be derived.

Example III

Morphology Analysis

Morphological analysis was performed to determine whether changes in polypeptide levels affect plant growth and development. This was primarily carried out on the T1 generation, when at least 10-20 independent lines were examined. However, in cases where a phenotype required confirmation or detailed characterization, plants from subsequent generations were also analyzed.

Primary transformants were selected on MS medium with 0.3% sucrose and 50 mg/l kanamycin. T2 and later generation plants were selected in the same manner, except that kanamycin was used at 35 mg/l. In cases where lines carry a sulfonamide marker (as in all lines generated by super-transformation), seeds were selected on MS medium with 0.3% sucrose and 1.5 mg/l sulfonamide. KO lines were usually germinated on plates without a selection. Seeds were cold-treated (stratified) on plates for three days in the dark (in order to increase germination efficiency) prior to transfer to growth cabinets. Initially, plates were incubated at 22° C. under a light intensity of approximately 100 microEinsteins for 7 days. At this stage, transformants were green, possessed the first two true leaves, and were easily distinguished from bleached kanamycin or sulfonamide-susceptible seedlings. Resistant seedlings were then transferred onto soil (Sunshine potting mix). Following transfer to soil, trays of seedlings were covered with plastic lids for 2-3 days to maintain humidity while they became established. Plants were grown on soil under fluorescent light at an intensity of 70-95 microEinsteins and a temperature of 18-23° C. Light conditions consisted of a 24-hour photoperiod unless otherwise stated. In instances where alterations in flowering time were apparent, flowering time was re-examined under both 12-hour and 24-hour light to assess whether the phenotype was photoperiod dependent. Under our 24-hour light growth conditions, the typical generation time (seed to seed) was approximately 14 weeks.

Because many aspects of *Arabidopsis* development are dependent on localized environmental conditions, in all cases plants were evaluated in comparison to controls in the same flat. As noted below, controls for transgenic lines were wild-type plants or transgenic plants harboring an empty transformation vector selected on kanamycin or sulfonamide. Careful examination was made at the following stages: seedling (1 week), rosette (2-3 weeks), flowering (4-7 weeks), and late seed set (8-12 weeks). Seed was also inspected. Seedling morphology was assessed on selection plates. At all other stages, plants were macroscopically evaluated while growing on soil. All significant differences (including alterations in growth rate, size, leaf and flower morphology, coloration, and flowering time) were recorded, but routine measurements were not taken if no differences were apparent. In certain cases, stem sections were stained to reveal lignin distribution. In these instances, hand-sectioned stems were mounted in phloroglucinol saturated 2M HCl (which stains lignin pink) and viewed immediately under a dissection microscope.

Note that for a given project (gene-promoter combination, GAL4 fusion lines, RNAi lines etc.), ten lines were typically examined in subsequent plate based physiology assays.

Example IV

Physiology Experimental Methods

In subsequent Examples, unless otherwise indicted, morphological and physiological traits are disclosed in comparison to wild-type control plants. That is, a transformed plant that is described as large and/or drought tolerant was large and more tolerant to drought with respect to a control plant, the latter including wild-type plants, parental lines and lines transformed with a vector that does not contain a sequence of interest. When a plant is said to have a better performance than controls, it generally was larger, had greater yield, and/or showed less stress symptoms than control plants. The better performing lines may, for example, have produced less anthocyanin, or were larger, greener, or more vigorous in response to a particular stress, as noted below. Better performance generally implies greater size or yield, or tolerance to a particular biotic or abiotic stress, less sensitivity to ABA, or better recovery from a stress (as in the case of a soil-based drought treatment) than controls.

Plate Assays. Different plate-based physiological assays (shown below), representing a variety of abiotic and water-deprivation-stress related conditions, were used as a pre-screen to identify top performing lines (i.e. lines from transformation with a particular construct), that were generally then tested in subsequent soil based assays. Typically, ten lines were subjected to plate assays, from which the best three lines were selected for subsequent soil based assays. However, in projects where significant stress tolerance was not obtained in plate based assays, lines were not submitted for soil assays.

In addition, some projects were subjected to nutrient limitation studies. A nutrient limitation assay was intended to find genes that allowed more plant growth upon deprivation of nitrogen. Nitrogen is a major nutrient affecting plant growth and development that ultimately impacts yield and stress tolerance. These assays monitored primarily root but also rosette growth on nitrogen deficient media. In all higher plants, inorganic nitrogen is first assimilated into glutamate, glutamine, aspartate and asparagine, the four amino acids used to transport assimilated nitrogen from sources (e.g. leaves) to sinks (e.g. developing seeds). This process may be regulated by light, as well as by C/N metabolic status of the plant. A C/N sensing assay was thus used to look for alterations in the mechanisms plants use to sense internal levels of carbon and nitrogen metabolites which could activate signal transduction cascades that regulate the transcription of N-assimilatory genes. To determine whether these mechanisms are altered, we exploited the observation that wild-type plants grown on media containing high levels of sucrose (3%) without a nitrogen source accumulate high levels of anthocyanins. This sucrose induced anthocyanin accumulation can be relieved by the addition of either inorganic or organic nitrogen. We used glutamine as a nitrogen source since it also serves as a compound used to transport N in plants.

Germination assays. The following germination assays were conducted with *Arabidopsis* overexpressors of G1988 and closely-related sequences: NaCl (150 mM), mannitol (300 mM), sucrose (9.4%), ABA (0.3 µM), cold (8° C.), polyethylene glycol (10%, with Phytogel as gelling agent), or C/N sensing or low nitrogen medium. In the text below, −N refers to basal media minus nitrogen plus 3% sucrose and −N/+Gln is basal media minus nitrogen plus 3% sucrose and 1 mM glutamine.

All germination assays were performed in tissue culture. Growing the plants under controlled temperature and humidity on sterile medium produces uniform plant material that has not been exposed to additional stresses (such as water stress) which could cause variability in the results obtained. All assays were designed to detect plants that were more tolerant or less tolerant to the particular stress condition and were developed with reference to the following publications: Jang et al. (1997), Smeekens (1998), Liu and Zhu (1997), Saleki et al. (1993), Wu et al. (1996), Zhu et al. (1998), Alia et al. (1998), Xin and Browse, (1998), Leon-Kloosterziel et al. (1996). Where possible, assay conditions were originally tested in a blind experiment with controls that had phenotypes related to the condition tested.

Prior to plating, seed for all experiments were surface sterilized in the following manner: (1) 5 minute incubation with mixing in 70% ethanol, (2) 20 minute incubation with mixing in 30% bleach, 0.01% triton-X 100, (3) 5× rinses with sterile water, (4) Seeds were re-suspended in 0.1% sterile agarose and stratified at 4° C. for 3-4 days.

All germination assays follow modifications of the same basic protocol. Sterile seeds were sown on the conditional media that has a basal composition of 80% MS+Vitamins. Plates were incubated at 22° C. under 24-hour light (120-130 µE m$^{-2}$ s$^{-1}$) in a growth chamber. Evaluation of germination and seedling vigor was performed five days after planting.

Growth assays. The following growth assays were conducted with *Arabidopsis* overexpressors of G1988 and closely-related sequences: severe desiccation (a type of water deprivation assay), growth in cold conditions at 8° C., root development (visual assessment of lateral and primary roots, root hairs and overall growth), and phosphate limitation. For the nitrogen limitation assay, plants were grown in 80% Murashige and Skoog (MS) medium in which the nitrogen source was reduced to 20 mg/L of $NH_4NO_3$. Note that 80% MS normally has 1.32 g/L $NH_4NO_3$ and 1.52 g/L $KNO_3$. For phosphate limitation assays, seven day old seedlings were germinated on phosphate-free medium in MS medium in which $KH_2PO_4$ was replaced by $K_2SO_4$.

Unless otherwise stated, all experiments were performed with the *Arabidopsis thaliana* ecotype Columbia (col-0), soybean or maize plants. Assays were usually conducted on non-selected segregating T2 populations (in order to avoid the extra stress of selection). Control plants for assays on lines containing direct promoter-fusion constructs were Col-0 plants transformed an empty transformation vector (pMEN65). Controls for 2-component lines (generated by supertransformation) were the background promoter-driver lines (i.e. promoter::LexA-GAL4TA lines), into which the supertransformations were initially performed.

Procedures

For chilling growth assays, seeds were germinated and grown for seven days on MS+Vitamins +1% sucrose at 22° C. and then transferred to chilling conditions at 8° C. and evaluated after another 10 days and 17 days.

For severe desiccation (plate-based water deprivation) assays, seedlings were grown for 14 days on MS+Vitamins+ 1% Sucrose at 22° C. Plates were opened in the sterile hood for 3 hr for hardening and then seedlings were removed from the media and let dry for two hours in the hood. After this time the plants were transferred back to plates and incubated at 22° C. for recovery. The plants were then evaluated after five days.

For the polyethylene glycol (PEG) hyperosmotic stress tolerance screen, plant seeds were gas sterilized with chlorine gas for 2 hrs. The seeds were plated on each plate containing 3% PEG, ½×MS salts, 1% phytagel, and 10 μg/ml glufosinate-ammonium (BASTA). Two replicate plates per seed line were planted. The plates were placed at 4° C. for 3 days to stratify seeds. The plates were held vertically for 11 additional days at temperatures of 22° C. (day) and 20° C. (night). The photoperiod was 16 hrs. with an average light intensity of about 120 mmol/m2/s. The racks holding the plates were rotated daily within the shelves of the growth chamber carts. At 11 days, root length measurements are made. At 14 days, seedling status was determined, root length was measured, growth stage was recorded, the visual color was assessed, pooled seedling fresh weight was measured, and a whole plate photograph was taken.

Wilt screen assay. Transgenic and wild-type soybean plants were grown in 5" pots in growth chambers. After the seedlings reached the V1 stage (the V1 stage occurs when the plants have one trifoliolate, and the unifoliolate and first trifoliolate leaves are unrolled), water was withheld and the drought treatment thus started. A drought injury phenotype score was recorded, in increasing severity of effect, as 1 to 4, with 1 designated no obvious effect and 4 indicating a dead plant. Drought scoring was initiated as soon as one plant in one growth chamber had a drought score of 1.5. Scoring continued every day until at least 90% of the wild type plants had achieved scores of 3.5 or more. At the end of the experiment the scores for both transgenic and wild type soybean seedlings were statistically analyzed using Risk Score and Survival analysis methods (Glantz (2001); Hosmer and Lemeshow (1999)).

Water use efficiency (WUE). WUE was estimated by exploiting the observation that elements can exist in both stable and unstable (radioactive) forms. Most elements of biological interest (including C, H, O, N, and S) have two or more stable isotopes, with the lightest of these present in much greater abundance than the others. For example, $^{12}C$ is more abundant than $^{13}C$ in nature ($^{12}C$=98.89%, $^{13}C$=1.11%, $^{14}C$=<10-10%). Because $^{13}C$ is slightly larger than $^{12}C$, fractionation of $CO_2$ during photosynthesis occurs at two steps:

1. $^{12}CO_2$ diffuses through air and into the leaf more easily;

2. $^{12}CO_2$ is preferred by the enzyme in the first step of photosynthesis, ribulose bisphosphate carboxylase/oxygenase.

WUE has been shown to be negatively correlated with carbon isotope discrimination during photosynthesis in several C3 crop species. Carbon isotope discrimination has also been linked to drought tolerance and yield stability in drought-prone environments and has been successfully used to identify genotypes with better drought tolerance. $^{13}C/^{12}C$ content was measured after combustion of plant material and conversion to $CO_2$, and analysis by mass spectroscopy. With comparison to a known standard, $^{13}C$ content was altered in such a way as to suggest that overexpression of G1988 or related sequences improves water use efficiency.

Another potential indicator of WUE was stomatal conductance, that is, the extent to which stomata were open.

Data Interpretation

At the time of evaluation, plants were given one of the following scores:

(++) Substantially enhanced performance compared to controls. The phenotype was very consistent and growth was significantly above the normal levels of variability observed for that assay.

(+) Enhanced performance compared to controls. The response was consistent but was only moderately above the normal levels of variability observed for that assay.

(wt) No detectable difference from wild-type controls.

(−) Impaired performance compared to controls. The response was consistent but was only moderately above the normal levels of variability observed for that assay.

(−−) Substantially impaired performance compared to controls. The phenotype was consistent and growth was significantly above the normal levels of variability observed for that assay.

(n/d) Experiment failed, data not obtained, or assay not performed.

Example V

Soil Drought (Clay Pot)

The soil drought assay (performed in clay pots) was based on that described by Haake et al. (2002).

Experimental Procedure.

Previously, we have performed clay-pot assays on segregating T2 populations, sown directly to soil. However, in the current procedure, seedlings were first germinated on selection plates containing either kanamycin or sulfonamide.

Seeds were sterilized by a 2 minute ethanol treatment followed by 20 minutes in 30% bleach/0.01% Tween and five washes in distilled water. Seeds were sown to MS agar in 0.1% agarose and stratified for three days at 4° C., before transfer to growth cabinets with a temperature of 22° C. After seven days of growth on selection plates, seedlings were transplanted to 3.5 inch diameter clay pots containing 80 g of a 50:50 mix of vermiculite:perlite topped with 80 g of Pro-Mix. Typically, each pot contained 14 seedlings, and plants of the transgenic line being tested were in separate pots to the wild-type controls. Pots containing the transgenic line versus control pots were interspersed in the growth room, maintained under 24-hour light conditions (18-23° C., and 90-100 $\mu E\ m^{-2}\ s^{-1}$) and watered for a period of 14 days. Water was then withheld and pots were placed on absorbent paper for a period of 8-10 days to apply a drought treatment. After this period, a visual qualitative "drought score" from 0-6 was assigned to record the extent of visible drought stress symptoms. A score of "6" corresponded to no visible symptoms whereas a score of "0" corresponded to extreme wilting and the leaves having a "crispy" texture. At the end of the drought period, pots were re-watered and scored after 5-6 days; the number of surviving plants in each pot was counted, and the proportion of the total plants in the pot that survived was calculated.

Analysis of results. In a given experiment, we typically compared 6 or more pots of a transgenic line with 6 or more pots of the appropriate control. The mean drought score and mean proportion of plants surviving (survival rate) were calculated for both the transgenic line and the wild-type pots. In each case a p-value* was calculated, which indicated the significance of the difference between the two mean values. The results for each transgenic line across each planting for a particular project were then presented in a results table.

Calculation of p-values. For the assays where control and experimental plants were in separate pots, survival was analyzed with a logistic regression to account for the fact that the random variable is a proportion between 0 and 1. The reported p-value was the significance of the experimental proportion contrasted to the control, based upon regressing the logit-transformed data.

Drought score, being an ordered factor with no real numeric meaning, was analyzed with a non-parametric test between the experimental and control groups. The p-value was calculated with a Mann-Whitney rank-sum test.

Example VI

Soil Drought Physiological and Biochemical Measurements

These experiments determined the physiological basis for the drought tolerance conferred by each lead and were typically performed under soil grown conditions. Usually, the experiment was performed under photoperiodic conditions of 10-hr or 12-hr light. Where possible, a given project (gene/promoter combination or protein variant) was represented by three independent lines. Plants were usually at late vegetative/early reproductive stage at the time measurements were taken. Typically we assayed three different states: a well-watered state, a mild-drought state and a moderately severe drought state. In each case, we made comparisons to wild-type plants with the same degree of physical stress symptoms (wilting). To achieve this, staggered samplings were often required. Typically, for a given line, ten individual plants were assayed for each state.

The following physiological parameters were routinely measured: relative water content, ABA content, proline content, and photosynthesis rate. In some cases, measurements of chlorophyll levels, starch levels, carotenoid levels, and chlorophyll fluorescence were also made.

Analysis of results. In a given experiment, for a particular parameter, we typically compared about 10 samples from a given transgenic line with about 10 samples of the appropriate wild-type control at each drought state. The mean values for each physiological parameter were calculated for both the transgenic line and the wild-type pots. In each case, a p-value (calculated via a simple t-test) was determined, which indicated the significance of the difference between the two mean values.

A typical procedure is described below; this corresponds to method used for the drought time-course experiment which we performed on wild-type plants during our baseline studies at the outset of the drought program.

Procedure. Seeds were stratified for three days at 4° C. in 0.1% agarose and sown on Metromix 200 in 2.25 inch pots (square or round). Plants were maintained in individual pots within flats grown under short days (10 hours light, 14 hours dark). Seedlings were watered as needed to maintain healthy plant growth and development. At 7 to 8 weeks after planting, plants were used in drought experiments.

Plants matched for equivalent growth development (rosette size) were removed from plastic flats and placed on absorbent paper. Pots containing plants used as well-watered controls were placed within a weigh boat and the dish placed on the diaper paper. The purpose of the weigh boat was to retain any water that might leak from well-watered pots and affect pots containing plants undergoing the drought stress treatment.

On each day of sampling, up to 18 plants subjected to drought conditions and 6 well-watered controls (from each transgenic line) were picked from a randomly generated pool (given that they passed quality control standards). Biochemical analysis for photosynthesis, ABA, and proline was performed on the next three youngest, most fully expanded leaves. Relative water content was analyzed using the remaining rosette tissue.

Measurement of Photosynthesis. Photosynthesis was measured using a LICOR LI-6400 (Li-Cor Biosciences, Lincoln, Nebr.). The LI-6400 used infrared gas analyzers to measure carbon dioxide to generate a photosynthesis measurement. It was based upon the difference of the $CO_2$ reference (the amount put into the chamber) and the $CO_2$ sample (the amount that leaves the chamber). Since photosynthesis is the process of converting $CO_2$ to carbohydrates, we expected to see a decrease in the amount of $CO_2$ sample. From this difference, a photosynthesis rate could be generated. In some cases, respiration may occur and an increase in $CO_2$ detected. To perform measurements, the LI-6400 as set-up and calibrated as per LI-6400 standard directions. Photosynthesis was measured in the youngest, most fully expanded leaf at 300 and 1000 ppm $CO_2$ using a metal halide light source. This light source provided about 700 $\mu E\ m^{-2}\ s^{-1}$.

Fluorescence was measured in dark and light adapted leaves using either a LI-6400 (LICOR) with a leaf chamber fluorometer attachment or an Os-1 (Opti-Sciences, Hudson, N.H.) as described in the manufacturer's literature. When the LI-6400 was used, all manipulations were performed under a dark shade cloth. Plants were dark adapted by placing in a box under this shade cloth until used. The OS-30 utilized small clips to create dark adapted leaves.

Measurement of Abscisic Acid and Proline. The purpose of this experiment was to measure ABA and proline in plant tissue. ABA is a plant hormone believed to be involved in stress responses and proline is an osmoprotectant.

Three of the youngest, most fully expanded mature leaves were harvested, frozen in liquid nitrogen, lyophilized, and a dry weight measurement taken. Plant tissue was then homogenized in methanol to which 500 ng of d6-ABA has been added to act as an internal standard. The homogenate was filtered to removed plant material and the filtrate evaporated to a small volume. To this crude extract, approximately 3 ml of 1% acetic acid was added and the extract was further evaporated to remove any remaining methanol. The volume of the remaining aqueous extract was measured and a small aliquot (usually 200 to 500 µl) removed for proline analysis (Protocol described below). The remaining extract was then partitioned twice against ether, the ether removed by evaporation and the residue methylated using ethereal diazomethane. Following removal of any unreacted diazomethane, the residue was dissolved in 100 to 200 µl ethyl acetate and analyzed by gas chromatography-mass spectrometry. Analysis was performed using an HP 6890 GC coupled to an HP 5973 MSD using a DB-5 ms gas capillary column.

Column pressure was 20 psi. Initially, the oven temperature was 150° C. Following injection, the oven was heated at 5° C./min to a final temperature of 250° C. ABA levels was estimated using an isotope dilution equation and normalized to tissue dry weight.

Free proline content was measured according to Bates (Bates et al., 1973). The crude aqueous extract obtained above was brought up to a final volume of 500 µl using distilled water. Subsequently, 500 µl of glacial acetic was added followed by 500 µl of Chinard's Ninhydrin. Chinard's Ninhydrin was prepared by dissolving 2.5 g ninhydrin (triketohydrindene hydrate) in 60 ml glacial acetic acid at 70° C. to which 40 ml of 6 M phosphoric acid was added.

The samples were then heated at 95° to 100° C. for one hour. After this incubation period, samples were cooled and 1.5 ml of toluene were added. The upper toluene phase was removed and absorbance measured at 515 nm. Amounts of proline were estimated using a standard curve generated using L-proline and normalized to tissue dry weight.

Measurement of Relative Water Content. Relative Water Content (RWC) indicated the amount of water that is stored within the plant tissue at any given time. It was obtained by taking the field weight of the rosette minus the dry weight of the plant material and dividing by the weight of the rosette saturated with water minus the dry weight of the plant material. The resulting RWC value could be compared from plant to plant, regardless of plant size.

$$\text{Relative Water Content} = \frac{\text{Field Weight} - \text{Dry Weight}}{\text{Turgid Weight} - \text{Dry Weight}} \times 100$$

After tissue had been removed for array and ABA/proline analysis, the rosette was cut from the roots using a small pair of scissors. The field weight was obtained by weighing the rosette. The rosette was then immersed in cold water and placed in an ice water bath in the dark. The purpose of this was to allow the plant tissue to take up water while preventing any metabolism which could alter the level of small molecules within the cell. The next day, the rosette was carefully removed, blotted dry with tissue paper, and weighed to obtain the turgid weight. Tissue was then frozen, lyophilized, and weighed to obtain the dry weight.

Starch determination. Starch was estimated using a simple iodine based staining procedure. Young, fully expanded leaves were harvested either at the end or beginning of a 12 hour light period and placed in tubes containing 80% ethanol or 100% methanol. Leaves were decolorized by incubating tubes in a 70° to 80° C. water bath until chlorophyll had been removed from leaf tissue. Leaves were then immersed in water to displace any residual methanol which may be present in the tissue. Starch was then stained by incubating leaves in an iodine stain (2 g KI, 1 g $I_2$ in 100 ml water) for one min and then washing with copious amounts of water. Tissue containing large amounts of starch stained dark blue or black; tissues depleted in starch were colorless.

Chlorophyll/carotenoid determination. For some experiments, chlorophyll was estimated in methanolic extracts using the method of Porra et al. (1989). Carotenoids were estimated in the same extract at 450 nm using an A(1%) of 2500. We measured chlorophyll using a Minolta SPAD-502 (Konica Minolta Sensing Americas, Inc., Ramsey, N.J.). When the SPAD-502 was used to measure chlorophyll, both carotenoid and chlorophyll content and amount could also be determined via HPLC. Pigments were extracted from leave tissue by homogenizing leaves in acetone:ethyl acetate (3:2). Water was added, the mixture centrifuged, and the upper phase removed for HPLC analysis. Samples were analyzed using a Zorbax (Agilent Technologies, Palo Alto, Calif.) C18 (non-endcapped) column (250×4.6) with a gradient of acetonitrile:water (85:15) to acetonitrile:methanol (85:15) in 12.5 minutes. After holding at these conditions for two minutes, solvent conditions were changed to methanol:ethyl acetate (68:32) in two minutes.

Carotenoids and chlorophylls were quantified using peak areas and response factors calculated using lutein and beta-carotene as standards.

Nuclear and cytoplasmically-enriched fractions. We developed a platform to prepare nuclear and cytoplasmic protein extracts in a 96-well format using a tungsten carbide beads for cell disruption in a mild detergent and a sucrose cushion to separate cytoplasmic from nuclear fractions. We used histone antibodies to demonstrate that this method effectively separates cytoplasmic from nuclear-enriched fractions. An alternate method (spun only) used the same disruption procedure, but simply pelleted the nuclei to separate them from the cytoplasm without the added purification of a sucrose cushion.

Quantification of mRNA level. Three shoot and three root biological replicates were typically harvested for each line, as described above in the protein quantification methods section. RNA was prepared using a 96-well format protocol, and cDNA synthesized from each sample. These preparations were used as templates for RT-PCR experiments. We measured the levels of transcript for a gene of interest relative to 18S RNA transcript for each sample using an ABI 7900 Real-Time RT-PCR machine with SYBR® Green technology (Applied Biosystems, Foster City, Calif.).

Phenotypic Analysis: Flowering time. Plants were grown in soil. Flowering time was determined based on either or both of (i) number to days after planting to the first visible flower bud. (ii) the total number of leaves (rosette or rosette plus cauline) produced by the primary shoot meristem.

Phenotypic Analysis: Heat stress. In preliminary experiments described in this report, plants were germinated growth chamber at 30° C. with 24 hour light for 11 days. Plants were allowed to recover in 22° C. with 24 hour light for three days, and photographs were taken to record health after the treatment. In a second experiment, seedlings were grown at 22° C. for four days on selective media, and the plates transferred to 32° C. for one week. They were then allowed to recover at 22° C. for three days. Forty plants from two separate plates were harvested for each line, and both fresh weight and chlorophyll content measured.

Phenotypic Analysis: dark-induced senescence. In preliminary experiments described in this report, plants were grown on soil for 27-30 days in 12 h light at 22° C. They were moved to a dark chamber at 22° C., and visually evaluated for senescence after 10-13 days. In some cases we used Fv/Fm as a measure of chlorophyll (Pourtau et al., 2004) on the youngest most fully-expanded leaf on each plant. The Fv/Fm mean for the 12 plants from each line was normalized to the Fv/Fm mean for the 12 matched controls.

Microscopy. Light microscopy, electron and confocal microscopy were performed.

Various Definitions/Abbreviations Used:
RWC=Relative water content (field wt.–dry weight)/(turgid wt.–dry wt.)×100
ABA=Abscisic acid, µg/gdw
Proline=Proline, µmole/gdw
Chl SPAD=Chlorophyll estimated by a Minolta SPAD-502, ratio of 650 nm to 940 nm A 300=net assimilation rate, μmole $CO_2/m^2/s$ at 300 ppm $CO_2$
A 1000=net assimilation rate, μmole $CO_2/m^2/s$ at 1000 ppm $CO_2$
Total Chl=mg/gfw, estimated by HPLC
Carot=mg/gfw, estimated by HPLC
Fo=minimal fluorescence of a dark adapted leaf
Fm=maximal fluorescence of a dark adapted leaf
Fo'=minimal fluorescence of a light adapted leaf
Fm'=maximal fluorescence of a light adapted leaf
Fs=steady state fluorescence of a light adapted leaf
Psi if =water potential (Mpa) of a leaf
Psi p=turgor potential (Mpa) of a leaf
Psi pi=osmotic potential (Mpa) of a leaf
Fv/Fm=(Fm−Fo)/Fm; maximum quantum yield of PSII
Fv'/Fm'=(Fm'−Fo')/Fm'; efficiency of energy harvesting by open PRII reaction centers
PhiPS2=(Fm'−Fs)/Fm', actual quantum yield of PSII
ETR=PhiPS2× light intensity absorbed×0.5; we use 100 g/m²/s for an average light intensity and 85% as the amount of light absorbed
qP=(Fm'−Fs)/(Fm'Fo'); photochemical quenching (includes photosynthesis and photorespiration); proportion of open PRII
qN=(Fm−Fm')/(Fm−Fo'); non-photochemical quenching (includes mechanisms like heat dissipation)
NPQ=(Fm−Fm')/Fm'; non-photochemical quenching (includes mechanisms like heat dissipation)
Screening for Water Use Efficiency An aspect of this invention provides transgenic plants with enhanced yield resulting from enhanced water use efficiency and/or water deprivation tolerance.

This example describes a high-throughput method for greenhouse selection of transgenic plants to wild type plants (tested as inbreds or hybrids) for water use efficiency. This selection process imposed three drought/re-water cycles on the plants over a total period of 15 days after an initial stress free growth period of 11 days. Each cycle consisted of five days, with no water being applied for the first four days and a water quenching on the fifth day of the cycle. The primary phenotypes analyzed by the selection method were the changes in plant growth rate as determined by height and biomass during a vegetative drought treatment. The hydration status of the shoot tissues following the drought was also measured. The plant heights were measured at three time points. The first was taken just prior to the onset drought when the plant was 11 days old, which was the shoot initial height (SIH). The plant height was also measured halfway throughout the drought/re-water regimen, on day 18 after planting, to give rise to the shoot mid-drought height (SMH). Upon the completion of the final drought cycle on day 26 after planting, the shoot portion of the plant was harvested and measured for a final height, which was the shoot wilt height (SWH) and also measured for shoot wilted biomass (SWM). The shoot was placed in water at 40° C. in the dark. Three days later, the weight of the shoot was determined to provide the shoot turgid weight (STM). After drying in an oven for four days, the weights of the shoots were determined to provide shoot dry biomass (SDM). The shoot average height (SAH) was the mean plant height across the three height measurements. If desired, the procedure described above may be adjusted for +/−~one day for each step. To correct for slight differences between plants, a size corrected growth value was derived from SIH and SWH. This was the Relative Growth Rate (RGR). Relative Growth Rate (RGR) was calculated for each shoot using the formula [RGR %=(SWH−SIH)/((SWH+SIH)/2)*100]. Relative water content (RWC) is a measurement of how much (%) of the plant was water at harvest. Water Content (RWC) was calculated for each shoot using the formula [RWC %=(SWM−SDM)/(STM−SDM)*100]. For example, fully watered corn plants of this stage of development have around 98% RWC.

Example VII

Morphological Observations with G1988 and Related Sequence Overexpressors in *Arabidopsis*

In our earlier studies, overexpression of G1988 in *Arabidopsis* produced a small number of lines that flowered early, and in several overexpressing lines seedlings grew faster than control seedlings. We also demonstrated that, when grown on phosphate-free media, all lines of *Arabidopsis* seedlings constitutively overexpressing G1988 under the regulatory control of the 35S promoter appeared larger and had more root growth than controls. 35S::G1988 plants with high levels of G1988 expression produced long hypocotyls, long petioles, and upright leaves, phenotypes that suggest a role for this gene in light signaling, which may be one of the factors responsible for conferring increased yield in crop plants. 35S::G1988 lines showed additional striking phenotypes when grown under long days (16 hr light) or continuous light; the plants were stunted and displayed premature chlorosis and delayed development. In addition, occasional water-soaking of leaves was noted.

For the present study, fifty-one new 35S::G1988 direct promoter fusion lines were generated. Nine of these lines showed a long hypocotyl phenotype in the T1 generation. Ten lines that had not shown long hypocotyls in the T1 were examined in the T2 generation, and six of these lines showed at least some plants with long hypocotyls and long petioles, suggesting that the penetrance of the phenotype may be influenced by gene dosage or environmental conditions. The majority of T1 lines examined exhibited upraised leaves. Effects on flowering were inconsistent; some T1 lines were again noted to flower early, but careful characterization of two 35S::G1988 lines with high G1988 expression levels revealed either no difference in flowering or a slight delay, depending on the day length in which the plants were grown.

Morphological Similarities Conferred by G1988 and Orthologs

35S::G4000 (maize SEQ ID NOs: 7 and 8), 35S::G4012 (rice SEQ ID NOs: 15 and 16), 35S::G4299 (tomato SEQ ID NOs: 21 and 22), 35S::G4004 (soy SEQ ID NOs: 3 and 4) and 35S::G4005 (soy SEQ ID NOs: 5 and 6) lines showed similar morphology to 35S::G1988 lines. A number of 35S::G4012, 35S::G4004 and 35S::G4005 T1 seedlings had extended petioles on cotyledons, and 35S::G4000, 35S::G4012, 35S::G4299, and 35S::G4004 seedlings also had longer hypocotyls than controls under continuous light. Adult 35S::G4004 and 35S::G4005 plants also appeared very similar to high-expressing 35S::G1988 plants when grown under continuous light. When constitutively overexpressed, all of these sequences produced plants that had upright leaves, similar to the continuous light grown 35S::G1988 plants. The observations of upheld leaves, long hypocotyls and long petioles suggest that G4004 and G4005 function similarly to G1988 in light signaling, which may be a factor that can contribute to improved yield in G1988 clade-overexpressing plants. A number of 35S::G4004 lines were late in their development relative to the controls.

Of the twenty transgenic lines examined, one of the 35S::G4005 lines was larger in size than controls at the seedling stage, another line was wild-type in size, and all other lines were smaller in size than controls at this stage.

Effect of Ectopic Expression of G1988 on Early Season Growth

Constitutive overexpression of G1988 in soybean plants resulted in consistent increases in early season growth relative to control plants. This effect was particularly evident when the seeds of the overexpressors and controls were planted in late as opposed to early spring. In particular, lines of G1988 overexpressors that were associated with high yield, such as lines 178, 189, 200, 209, 213 and 218 (see, for example, Table 12) generally exhibited greater early season growth than controls.

Effect of Ectopic Expression of G1988 on Stem Diameter in Soy Plants

When grown in controlled short day conditions (10 hours of light), lines of soybean plants overexpressing G1988 did not appear to show increased stem diameters relative to control plants to any significant extent. However, at long day lengths (20 hours of light), G1988 overexpressors generally produced significantly greater stem diameter than controls. Increased stem diameters of G1988 overexpressors were confirmed in soybean plants grown in field conditions. Increased stem diameter can positively impact biomass as well as contribute to increased resistance to lodging.

TABLE 5

Soybean stem diameters of various G1988 overexpressors and controls grown at short and long day lengths

| Line | Day length | Average stem diameter (mm) | Difference from controls, average stem diameter (mm) | P-value |
|---|---|---|---|---|
| 206** | Short day | 4.35 | −0.47 | 0.025 |
| 178 | Short day | 4.43 | −0.39 | 0.049 |
| 218 | Short day | 4.60 | −0.22 | 0.250 |
| A3244 (control) | Short day | 4.82 | — | |
| 209 | Short day | 4.89 | +0.07 | 0.338 |
| 213 | Short day | 4.89 | +0.07 | 0.268 |
| A3244 (control) | Long day | 15.75 | — | |
| 178 | Long day | 16.83 | +1.08 | 0.071 |
| 213 | Long day | 16.92 | +1.07* | 0.021 |
| 218 | Long day | 17.46 | +1.71* | 0.004 |
| 206** | Long day | 16.29 | +0.54 | 0.104 |
| 209 | Long day | 17.17 | +1.42* | 0.027 |

*line showed a greater stem diameter relative to controls (significant at p < 0.05)
**did not express G1988 to a significant level Effect of Ectopic Expression of G1988 on Internode Length in Soy Plants In short day experiments (10 hours of light per day), soybean internode length increased, relative to controls. This effect was generally noticeable for almost all of the plants' internodes, but was particularly conspicuous for internodes 8-12 which formed relatively late in the plants' development (FIG. 10). However, internode length was generally greater at virtually all stages of growth, including during early season growth as seen with the early internodes (for example, internodes 1-5) compared in FIG. 10.

Effect of Ectopic Expression of G1988 on Canopy Coverage

Constitutive overexpression of G1988 in soybean plants resulted in consistent increases in late season canopy coverage relative to control plants. Increased canopy coverage was positively associated with lines that produced increased yield. Line 217, which did not overexpress as G1988 to the same extend as did the high-yielding lines (line 217 ectopically expressed about 60% of the level of G1988 as generally found in high-yielding lines), did not exhibit significantly greater canopy coverage relative to controls.

Example VIII

Plate-Based Experimental Results

This report provides experimental observations for transgenic seedlings overexpressing G1988-related polypeptides in plate-based assays, testing for tolerance to abiotic stresses including water deprivation, cold, and low nitrogen or altered C/N sensing.

G1988 (SEQ ID NO: 1 and 2; *Arabidopsis thaliana*)—Constitutive 35S Promoter

Plate-Based Physiology Assay Results in *Arabidopsis*

In our earlier studies, we demonstrated that seedlings germinated on plates that contained limited nitrogen (supplemented with glutamine) appeared less stressed than controls.

35S::G1988 plants were found to have altered performance in an assay measuring response to altered carbon/nitrogen ratios (C/N sensing assay). Nine out of ten 35S::G4004 lines also showed a significantly different response compared to control seedlings in a C/N sensing assay, consistent with the phenotype observed for 35S::G1988 plants.

Ten 35S::G1988 *Arabidopsis* plant lines were examined in physiological assays. In addition to the C/N sensing phenotype observed in previous analyses, enhanced performance on low nitrogen in a root growth assay was also observed. Three out of ten lines also showed dehydration tolerance in a plate-based severe desiccation assay, a type of water deprivation assay. Tolerance to sucrose (hyperosmotic stress in 9.4% sucrose) in a germination assay was also observed in six lines. These latter results suggested that the overexpressors would be more tolerant to other forms of water deprivation, such as drought and other related stresses. This supposition was confirmed by the results of a soil-based drought assay as noted below.

TABLE 6

G1988 (SEQ ID NO: 1 and 2 from *Arabidopsis thaliana* col) - Constitutive 35S Direct Promoter Fusion

| Line | Sucrose germ. | ABA germ. | Cold germ. | Growth in cold | Severe desiccation | Low N germ. | Germ. in low N + gln | Low N root growth |
|---|---|---|---|---|---|---|---|---|
| 321 | | | | | | + | + | + |
| 322 | + | | | | | + | + | + |
| 323 | | | | | | + | + | + |
| 324 | | | | | | | + | |
| 325 | + | | | | + | | | |
| 326 | + | | | | + | | | + |
| 327 | | | | | | + | + | + |

TABLE 6-continued

G1988 (SEQ ID NO: 1 and 2 from *Arabidopsis thaliana* col) -
Constitutive 35S Direct Promoter Fusion

| Line | Sucrose germ. | ABA germ. | Cold germ. | Growth in cold | Severe desiccation | Low N germ. | Germ. in low N + gln | Low N root growth |
|------|---------------|-----------|------------|----------------|--------------------|-------------| ---------------------|--------------------|
| 328  | +             |           |            |                |                    | +           | +                    | +                  |
| 329  | +             |           |            |                |                    | +           | +                    | +                  |
| 330  | +             |           |            |                |                    | +           | +                    | +                  | germ. = germination,
gln = glutamine
(+) indicates positive assay result/more tolerant or phenotype observed, relative to controls
(empty cell) indicates plants overexpressing G1988 in the line in the first column were wild-type in their performance In addition to the experimental results shown in Table 6, 35S::G1988 seedlings were also found to be more tolerant to growth on 3% polyethylene glycol in a PEG-based hyperosmotic stress tolerance screen than control seedlings. 35S::G1988 seedlings showed more extensive root growth than controls on 3% polyethylene glycol.

Although G1988, SEQ ID NO: 1 and 2, did not confer increased cold tolerance in *Arabidopsis* in this set of experiments, G1988 was able to confer greater tolerance to cold, relative to controls, in germinating soybean plants overexpressing the *Arabidopsis* G1988 protein.

G4004 (SEQ ID NO: 3 and 4 from *Glycine max*)—Overexpressed with the Constitutive CaMV 35S Promoter Based on the results conducted to date, 35S::G4004 overexpressors were more tolerant to low nitrogen conditions and demonstrated a C/N sensing phenotype In addition, seven of the 35S::G4004 lines performed better than control seedlings in a germination assay under cold conditions, as evidenced by less anthocyanin accumulation occurring in the transgenic plants, suggesting that this gene may also have utility in conferring improved cold germination (Table 7). Seedlings on control germination plates were noted to have long hypocotyls for seven out of ten lines examined. Seedlings were also noted to be small and stunted on control growth plates; given that these assays were performed under continuous light, this phenotype was consistent with the stunting noted in morphological assays. These transgenic plants were also more tolerant to cold during their germination than controls, as evidenced by less anthocyanin accumulation occurring in the transgenic plants. (Table 7).

TABLE 7

G4004 (SEQ ID NO: 3 and 4 from *Glycine max*) -
Constitutive 35S Direct Promoter Fusion

| Line | Sucrose germ. | Cold germ. | Severe desiccation | Low N germ. | Germ. in low N + gln |
|------|---------------|------------|--------------------|-------------|----------------------|
| 301  | −             |            |                    | +           | +                    |
| 302  | +             |            |                    | +           | +                    |
| 303  | +             |            |                    | +           | +                    |
| 304  | +             |            |                    | +           | +                    |
| 305  | +             |            |                    | +           | +                    |
| 306  | +             |            |                    | +           | +                    |
| 308  |               | +          |                    | +           | +                    |
| 309  |               |            |                    | +           | +                    |
| 310  |               |            |                    |             | +                    |
| 311  |               | +          |                    | +           | +                    | germ. = germination
(+) indicates positive assay result/more tolerant or phenotype observed, relative to controls
(empty cell) indicates plants overexpressing G1988 in the line in the first column were wild-type in their performance
(−) indicates a more sensitive phenotype was observed relative to controls Example IX Drought Assay Results in *Arabidopsis* and Soybean Water is a major limiting factor for crop yield. In water-limited environments, crop yield is a function of water use, water use efficiency (WUE; defined as aerial biomass yield/water use) and the harvest index (HI; the ratio of yield biomass to the total aerial biomass at harvest). WUE is a trait that has been proposed as a criterion for yield improvement under drought.

In a soil drought assay (a form of water deprivation assay that can be used to compare WUE), three well-characterized 35S::G1988 *Arabidopsis* lines were examined. Two of these lines, lines 10-6-3 and 12-2-2, had high levels of G1988 expression and exhibited long hypocotyls, upraised leaves, and elongated petioles. These lines each showed enhanced recovery from drought in one out of two assays performed. The third line, line 8-5-1, had lower levels of G1988 and did not exhibit the characteristic morphology of the other two lines. This line showed no improvement in survival, and, in fact, performed worse in one replicate of the assay (not shown in Table 8). Nonetheless, two individual lines were identified that did show significantly improved drought performance, and thus could be selected on that basis for further development and use as a product.

Soil Drought—Clay Pot-Based Physiology Summary.

TABLE 8

35S::G1988 drought assay results:

| PID | Line | Project Type | Mean drought score line | Mean drought score control | p-value for drought score difference | Mean survival for line | Mean survival for control | p-value for difference in survival |
|-----|------|--------------|-------------------------|----------------------------|---------------------------------------|------------------------|---------------------------|------------------------------------|
| P2499 | 10-6-3 | DPF | 3.1 | 2.2 | 0.29 | 0.55 | 0.41 | 0.015* |
| P2499 | 10-6-3 | DPF | 1.9 | 2.4 | 0.28 | 0.39 | 0.37 | 0.81 |

TABLE 8-continued

35S::G1988 drought assay results:

| PID | Line | Project Type | Mean drought score line | Mean drought score control | p-value for drought score difference | Mean survival for line | Mean survival for control | p-value for difference in survival |
|---|---|---|---|---|---|---|---|---|
| P2499 | 12-2-2 | DPF | 2.4 | 2.8 | 0.58 | 0.41 | 0.48 | 0.28 |
| P2499 | 12-2-2 | DPF | 2.8 | 2.1 | 0.17 | 0.49 | 0.36 | 0.022* |

DPF = direct promoter fusion project
Survival = proportion of plants in each pot that survived
Drought scale: 6 (highest score) = no stress symptoms, 0 (lowest score; most severe effect) = extreme stress symptoms
*line performed better than control (significant at p < 0.11)

In addition to *Arabidopsis* plants, soybean plants overexpressing also performed better than controls in a water use efficiency (WUE) screen. Tissue was harvested from dry locations and $^{13}C/^{12}C$ content was measured after combustion of plant material and conversion to $CO_2$, and analysis by mass spectroscopy. With comparison to a known standard, $^{13}C$ content was altered in such a way as to indicate that overexpression of G1988 improved water use efficiency.

Stomatal conductance was also measured. In the first field trial, three independent transgenic lines were found to have statistically significant lower conductance. Other 35S::G1988 soybean lines tested also had lower stomatal conductance, but the data obtained with these lines were not statistically significant. Significant differences in stomatal conductance was not observed in a subsequent field trial.

Taken together, the isotope discrimination and stomatal conductance analysis suggest that plants overexpressing G1988 have increased transpiration efficiency, which indicates enhanced water use efficiency by said plants.

A survival analysis of soybean plants overexpressing G1988 was performed using a wilt screen assay. When analyzed against wild-type control plants some of the lines of the transgenic lines tested showed significant (p<0.1) high risk score and prolonged time reaching wilting. Almost all of the eleven lines of overexpressors tested showed prolonged time to wilting, and the differences in time to wilting for three lines as compared to controls were statistically significant (Table 9, data presented in order of decreasing statistical significance). The only two lines that appeared to show more advanced wilting than controls (results not significant) did not express G1988 to a significant degree.

Taken together, these data clearly indicated that overexpression of G1988, SEQ ID NOs: 1 and 2, in soybean can significantly improve tolerance to water deficit conditions.

TABLE 9

Time to wilting of 35S::G1988 soy plants and controls

| Line | Mean time to wilting, overexpressors (days) | Mean time to wilting, controls (days) | Difference, time to wilting (days) | p value |
|---|---|---|---|---|
| 651* | 8.867 | 6.308 | 2.559 | 0.0008 |
| 200* | 7.933 | 6.308 | 1.625 | 0.0718 |
| 652* | 8.615 | 7.333 | 1.282 | 0.0834 |
| 189 | 8.714 | 8.200 | 0.514 | 0.1491 |
| 213 | 5.800 | 4.714 | 1.086 | 0.1619 |
| 217*** | 6.067 | 4.714 | 1.353 | 0.2022 |
| 198** | 6.938 | 8.200 | −1.262 | 0.2174 |
| 206** | 5.933 | 6.308 | −0.375 | 0.3105 |
| 209 | 7.200 | 6.308 | 0.892 | 0.4200 |

TABLE 9-continued

Time to wilting of 35S::G1988 soy plants and controls

| Line | Mean time to wilting, overexpressors (days) | Mean time to wilting, controls (days) | Difference, time to wilting (days) | p value |
|---|---|---|---|---|
| 178 | 8.000 | 7.083 | 0.917 | 0.6613 |
| 218 | 7.600 | 7.083 | 0.517 | 0.9039 |

*line showed a significant prolonged time to wilting relative to controls (significant at p < 0.10)
**did not express G1988 to a significant level
***expressed G1988 to a lower degree than high yielding transgenic lines Example X Results for Cold Tolerance in Soybean FIG. 7 displays experimental data obtained with a wild-type control line and numerous 35S::G1988 overexpressing lines showing that G1988 overexpression results in improved cold germination. The overall germination of the control seed from this field trial conducted in Winters, Calif., represented by the dotted line in FIG. 7, was poor and it was noted that a high percentage of the seed were "hard seed", a stress-induced phenomenon that results in seeds that resist imbibition under standard conditions. A significantly greater percentage of G1988 overexpressing seed germinated at various time points in this field trial and with seed obtained in trials conducted in Illinois and Kansas. These data indicate a role for G1988 in overcoming stress responses and enhancing cell growth.

G4004 (SEQ ID NO: 4), a soy homolog of G1988 that is phylogenetically related to G1988 (FIG. 3 and FIGS. 4A-4F) was transformed into corn plants. The germination index of the corn plants overexpressing G4004 was then determined. The germination index is a function of percentage germination and rate of germination, and can be defined by the formula:

$$\text{Germination index} = [(T-T1+1) \times P1 + (T-T2+1) \times (P2-P1) + (T-T3+1) \times (P3-P2) + \ldots + (T-TT+1) \times (PT-PT-1)]/T$$

where T is the number of days for which germination was tested.

P1, P2, P3, . . . and PT are the percentage of seeds germinated on day T1, T2, T3, . . . and T.

As shown in Table 10, germination of some of the G4004-overexpressing corn lines demonstrated the greater tolerance to cold of the overexpressors as compared to control plants.

TABLE 10

Phenotypic data from cold germination experiments of corn plants overexpressing G4004

| | Germination index | | | |
|---|---|---|---|---|
| | Trial 1 | | Trial 2 | |
| Line | % change | p value | % change | p value |
| 609 | −14 | 0.145 | −20 | 0.073 |
| 610 | −1 | 0.889 | −8 | 0.465 |
| 612 | 14 | 0.131 | 13 | 0.242 |
| 616 | 25* | 0.010* | 41* | 0.000* |
| 619 | 7 | 0.436 | 38 | 0.001 |
| 710 | 28* | 0.004* | 45 | 0.000* |
| 711 | 30* | 0.002* | 33 | 0.003* |
| 117 | −35 | 0.000** | −30 | 0.008** |

The data are presented as the percentage change over wild type controls.
*Germination index significantly greater than controls ($p < 0.05$)
**Germination index significantly less than controls ($p < 0.05$)

The present invention thus demonstrates that transformation of plants, including monocots, with a member of the G1988 Glade of polypeptides can confer to the transformed plants greater tolerance to cold conditions than the level of cold tolerance exhibited by control plants.

Example XI

Field Trial Results for Nitrogen Use Efficiency in Corn

A number of corn plants overexpressing the soybean G4004 polypeptide sequence (SEQ ID NO: 4) were more efficient in their use of nitrogen than control plants, as measured by increased chlorophyll and fresh shoot mass when grown in a greenhouse in low nitrogen media containing 2.0 mM ammonium nitrate as the nitrogen source (Table 11).

TABLE 11

Phenotypic data from low nitrogen screen of corn plants overexpressing G4004

| | Leaf chlorophyll | | Shoot fresh mass | |
|---|---|---|---|---|
| Line | Trial 1 | Trial 2 | Trial 1 | Trial 2 |
| 609 | 4.4 | 2.9 | 0.2 | −2.8 |
| 610 | 6.1* | 5.8* | 0.5 | 1.1 |
| 612 | 0.9 | 3.1 | −9.4** | −6.2** |
| 616 | 10.8* | 3.6 | 2.0 | −1.2 |
| 619 | 9.5* | 6.0* | 15.8* | 4.9* |
| 710 | 1.6 | 5.6* | 3.1 | −0.3 |
| 711 | 6.8* | 12.4* | 7.9* | 5.0 |
| 117 | 7.0* | 12.6* | 9.9* | 3.5 |

The data are presented as the percentage change over wild type controls.
*Value significantly greater than controls at $p < 0.05$
**Value significantly less than controls at $p < 0.10$ The present invention thus demonstrates that transgenic plants, including monocots, transformed with a member of the G1988 Glade of polypeptides can confer greater tolerance to low nitrogen conditions and increased nitrogen use efficiency to said transgenic plants, relative to the tolerance to low nitrogen conditions and nitrogen use efficiency of control plants.

Example XII

Improved Yield in Soybean Field Trials

*Arabidopsis thaliana* sequence G1988 (SEQ ID NOs: 1 and 2), a putative transcription factor, was shown to increase yield potential in *Glycine max* (soybean). In consecutive years of broad acre yield trials, transgenic plants constitutively expressing G1988 outperformed control cultivars, with a construct average of greater than 6% yield increase. Field observations of G1988 transgenic soybean identified several yield-related traits that were modulated by the transgene, including increased height, improved early season vigor and increased estimated stand count. G1988-overexpressing soy plants were slightly early flowering (less than one day as a construct average), slightly delayed in maturity (approximately one day as a construct average), and produced additional mainstem pod-containing nodes late at the end of the season (FIG. 9).

Table 12 shows results obtained with nine 35S::G1988 soybean lines tested for broad acre yield in 2004 at ten locations in the U.S., with two replicates per location. Each replicate was planted at a density of nine seeds per foot in two twelve foot rows divided by a three foot alley. Yield was recorded as bushels per acre and compared by spatial analysis to a non-transformed parental control line. The G1988 overexpressors showed increased yield in six of seven lines that showed significant expression of the transgene (Table 12). In addition to increased in yield, several of the lines showed early flowering, delayed maturity, and early stand count.

TABLE 12

Yield of 35S::G1988 overexpressing soy plants relative to control plants in a 2004 field trial

| Line | Yield (bushels/acre) | p value | mRNA expression (normalized average) |
|---|---|---|---|
| 206** | −5.86 | 0.000 | 19044 |
| 198** | −2.88 | 0.043 | 63330 |
| 217*** | −2.69 | 0.047 | 1412864 |
| 200* | 0.35 | 0.798 | 1972981 |
| 178* | 2.4 | 0.077 | 2155338 |
| 189* | 2.63 | 0.052 | 2197454 |
| 213* | 3.21 | 0.018 | 2088695 |
| 209* | 3.63 | 0.007 | 2175037 |
| 218* | 4.13 | 0.002 | 2158073 |

*showed significant increase in yield over controls
**did not express G1988 to a significant level
***expressed G1988 to a lower degree than high yielding transgenic lines Various lines of transgenic soybean plants overexpressing G1988 (35S::G1988) were also grown in field trials in 2005. In both 2004 and 2005, on average, G1988 overexpressing soybean plants were somewhat taller than control plants. When yield data were averaged across multiple locations, a consistent increase in yield in bushels per acre, as compared with parental line, was observed for both years (FIG. 6). In the 2005 field trial, G1988 overexpression significantly increased yield in 17 of 19 locations tested. If the line shown as line 4 in FIG. 6, which unlike other lines presented in FIG. 6 graph showed little or no expression of G1988 in leaf tissue, was removed from the statistical analysis, the average yield increase in 2005 was about 6.7%.

Analysis of soybean yield across three years of field trials showed that G1988, when overexpressed in numerous transgenic lines, was able to confer increased yield relative to controls (Table 13).

TABLE 13

Across year analysis of soybean yield of transgenic
lines overexpressing G1988

| Plant Line | Yield (bushels/acre) | Difference relative to control (bushels/acre) | % Difference | P value |
|---|---|---|---|---|
| 178* | 63.8 | +3.9 | 6.5 | 0.000 |
| 189* | 63.6 | +3.7 | 6.1 | 0.000 |
| 209* | 63.0 | +3.1 | 5.2 | 0.001 |
| 218* | 62.8 | +2.9 | 4.9 | 0.001 |
| 213* | 62.6 | +2.7 | 4.5 | 0.001 |
| 200* | 62.2 | +2.3 | 3.9 | 0.007 |
| 217*** | 59.8 | −0.2 | −0.3 | 0.827 |
| 206** | 58.1 | −1.8 | −3.1 | 0.031 |

*showed significant increase in yield over controls
**did not express G1988 to a significant level
***expressed G1988 to a lower degree than high yielding transgenic lines Table 14 demonstrates yet another means by which G1988 overexpression may increase yield in soy plants. In this table, the final stand count of transgenic and control plants from both early and late planting dates were compared. High yielding lines demonstrated a significantly greater final stand count than the control line tested under the same conditions. In numerous instances, these results were significant at $p<0.05$.

TABLE 14

Across year analysis of soybean yield of
transgenic lines overexpressing G1988

| Planting time | Line | Final Stand (plants per plot) | Emergence (%) | Difference from control plants (# plants) | P value |
|---|---|---|---|---|---|
| Early | 178 | 151 | 70 | 16 | 0.05* |
| Early | 189 | 147 | 68 | 11 | 0.15 |
| Early | 200 | 146 | 67 | 7 | 0.40 |
| Early | 206** | 141 | 65 | 4 | 0.65 |
| Early | 209 | 139 | 64 | 2 | 0.84 |
| Early | 213 | 150 | 69 | 16 | 0.05* |
| Early | 217*** | 142 | 66 | 6 | 0.45 |
| Early | 218 | 157 | 73 | 28 | 0.001* |
| Early | Control | 134 | 62 | 0 | |
| Late | 178 | 168 | 78 | 19 | 0.009* |
| Late | 189 | 161 | 74 | 14 | 0.04* |
| Late | 200 | 162 | 75 | 17 | 0.01* |
| Late | 206** | 152 | 71 | 5 | 0.42 |
| Late | 209 | 157 | 73 | 12 | 0.08* |
| Late | 213 | 164 | 76 | 18 | 0.01* |
| Late | 217*** | 153 | 71 | 4 | 0.56 |
| Late | 218 | 162 | 75 | 19 | 0.008* |
| Late | Control | 153 | 71 | 0 | |

*significant at p < 0.05
**did not express G1988 to a significant level
***expressed G1988 to a lower degree than high yielding transgenic lines FIG. 11 shows the results of a plant density field trial. The soybean plants represented in this figure that overexpressed G1988 demonstrated an observable yield increase across a wide range of plant densities, relative to control plants that either did not overexpress G1988 (shown as the unfilled circles), or control transgenic plants that did not express G1988 to a significant degree (shown as the filled circles).

Five lines of overexpressors are represented by the unfilled triangles, filled triangles, unfilled squares, filled squares, and asterisks. As shown in this figure, each of the five lines expressing G1988 to a significant degree provided a greater yield than the controls at all densities tested, and thus, the plant stand count did not have large contribution on harvestable yield.

One possible explanation for the increase in soy yield is an increase in pod-containing mainstem nodes relative to control plants that do not overexpress the G1988 polypeptide. As shown in FIG. 9, when various lines of soybean plants overexpressing a number of sequences were compared, a considerable range of the mean number of pod-containing mainstem nodes relative to the parental control line was observed (the observed difference for the control line was "0", and hence is represented in FIG. 9 by the "0" ordinate line). The shaded bars denote G1988 overexpressing lines, all of which produced more nodes than the control, with four of the five lines producing the highest positive difference in nodes observed.

The present invention thus demonstrates that transgenic plants, including legumes, and particularly including soybeans, transformed with a member of the G1988 Glade of polypeptides can show increased yield relative to the yield exhibited by control plants.

Example XIII

Utilities of G1988 and its Phylogenetically-Related
Sequences for Improving Yield Increased Abiotic Stress Tolerance May Improve Yield.

G1988 also improved stress tolerance in *Arabidopsis*, and early experiments have shown that G1988 closely related homologs also confer improved abiotic stress tolerance, relative to controls, to conditions such as cold or low nitrogen. Improved abiotic stress tolerance may have a significant impact on yield, including during periods of mild, moderate, and considerable stress.

Increased Stem Diameter May Improve Yield.

Increased stem diameter can positively impact biomass of a plant, and also provide increased resistance to lodging.

More Secondary Rooting May Improve Yield.

Providing greater secondary rooting by transforming plants with G1988 Glade member sequences can confer better anchorage relative to control plants. Transformed plants may also be produced that have the capacity to thrive in otherwise unproductive soils, such as in low nutrient environments, or in regions or periods of low water availability. Osmotic stress tolerance may also be mediated by increased root growth. These factors increase the effective planting range of the crop and/or increase survival and yield.

Increasing Numbers of Mainstem Nodes May Improve Yield.

The number of mainstem nodes of a variety of crops is related to the yield produced by the plant. For example, soybean and other seed-bearing crops produce seed-bearing pods from their mainstem nodes, and thus, increasing the number of mainstem nodes has a positive impact on seed number produced by the plant. Greater mainstem node number can also increase biomass or the yield of other crops such as cotton, where boll set is related to mainstem node number.

Reduced Light Sensitivity May Improve Yield.

Light exerts its influence on many aspects of plant growth and development, including germination, greening, and flowering time. Light triggers inhibition of hypocotyl elongation along with greening in young seedlings. Thus, differences in hypocotyl length are a good measure of responsiveness to light. Seedlings overexpressing G1988 exhibited elongated hypocotyls in light due to reduced inhibition of hypocotyl elongation. The G1988 overexpressors were also hyposensitive to blue, red and far-red wavelengths, indicating that G1988 acts downstream of the photoreceptors responsible for perceiving the different colors of light. This finding indicated that adult plants overexpressing G1988 had reduced sensitivity to the incumbent light.

Closely-related homologs of G1988 from corn (G4000, SEQ ID NO: 8), soybean (G4004, SEQ ID NO: 4), rice (G4012), and tomato (G4299, SEQ ID NO: 22), also conferred long hypocotyls when overexpressed in *Arabidopsis*. In experiments conducted thus far, overexpression of the soybean-derived homolog G4005, (SEQ ID NO: 6) did not cause long hypocotyls in the lines to be produced, but G4005 did confer other indications of an altered light response such as upright petioles and leaves. Thus, there is a strong correlation between G1988 and its orthologs from corn, soybean, rice and tomato in their ability to reduce light sensitivity, and these data indicate that G1988 and its closely related homologs function similarly in signaling pathways involved in light sensitivity. It is thus predicted that, like G1988, closely-related G1988 Glade member homologs may also improve traits that can be affected by reduced light sensitivity. Reduced light sensitivity may contribute to improvements in yield relative to control plants.

Greater Early Season Growth May Improve Yield.

For almost all commercial crops, it is desirable to use plants that establish quickly, since seedlings and young plants are particularly susceptible to stress conditions such as salinity or disease. Since many weeds may outgrow young crops or out-compete them for nutrients, it would also be desirable to determine means for allowing young crop plants to out compete weed species. Increasing seedling and young plant vigor allows for crops to be planted earlier in the season with less concern for losses due to environmental factors.

Greater Late Season Vigor may Improve yield.

Constitutive expression of G1988 significantly improved late season growth and vigor in soybeans. G1988 overexpressors had an increase in pod-containing mainstem nodes, greater plant height, and consistent increases in late season canopy coverage. These differences relative to control or untransformed plants may have had a significant positive impact on yield.

Because of the observed morphological, physiological and stress tolerance similarities between G1988 and its close-related homologs, the polypeptide members of the G1988 Glade, including the sequences presented in Table 1 and the Sequence Listing, are expected to increase yield, crop quality, and/or growth range, and decrease fertilizer and/or water usage in a variety of crop plants, ornamental plants, and woody plants used in the food, ornamental, paper, pulp, lumber or other industries.

Example XIV

Transformation of Eudicots to Produce Increased Yield and/or Abiotic Stress Tolerance Crop species that overexpress polypeptides of the invention may produce plants with increased water deprivation, cold and/or nutrient tolerance and/or yield in both stressed and non-stressed conditions. Thus, polynucleotide sequences listed in the Sequence Listing recombined into, for example, one of the expression vectors of the invention, or another suitable expression vector, may be transformed into a plant for the purpose of modifying plant traits for the purpose of improving yield and/or quality. The expression vector may contain a constitutive, tissue-specific or inducible promoter operably linked to the polynucleotide. The cloning vector may be introduced into a variety of plants by means well known in the art such as, for example, direct DNA transfer or *Agrobacterium tumefaciens*-mediated transformation. It is now routine to produce transgenic plants using most eudicot plants (see Weissbach and Weissbach (1989); Gelvin et al. (1990); Herrera-Estrella et al. (1983); Bevan (1984); and Klee (1985)). Methods for analysis of traits are routine in the art and examples are disclosed above.

Numerous protocols for the transformation of tomato and soy plants have been previously described, and are well known in the art. Gruber et al. (1993), in Glick and Thompson (1993) describe several expression vectors and culture methods that may be used for cell or tissue transformation and subsequent regeneration. For soybean transformation, methods are described by Miki et al. (1993); and U.S. Pat. No. 5,563,055, (Townsend and Thomas), issued Oct. 8, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al. (1987); Christou et al. (1992); Sanford (1993); Klein et al. (1987); U.S. Pat. No. 5,015,580 (Christou et al), issued May 14, 1991; and U.S. Pat. No. 5,322,783 (Tomes et al.), issued Jun. 21, 1994).

Alternatively, sonication methods (see, for example, Zhang et al. (1991)); direct uptake of DNA into protoplasts using $CaCl_2$ precipitation, polyvinyl alcohol or poly-L-ornithine (see, for example, Hain et al. (1985); Draper et al. (1982)); liposome or spheroplast fusion (see, for example, Deshayes et al. (1985); Christou et al. (1987)); and electroporation of protoplasts and whole cells and tissues (see, for example, Donn et al. (1990); D'Halluin et al. (1992); and Spencer et al. (1994)) have been used to introduce foreign DNA and expression vectors into plants.

After a plant or plant cell is transformed (and the transformed host plant cell then regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al (1986), and in U.S. Pat. No. 6,613,962, the latter method described in brief here. Eight day old cotyledon explants are precultured for 24 hours in Petri dishes containing a feeder layer of *Petunia hybrida* suspension cells plated on MS medium with 2% (w/v) sucrose and 0.8% agar supplemented with 10 μM α-naphthalene acetic acid and 4.4 μM 6-benzylaminopurine. The explants are then infected with a diluted overnight culture of *Agrobacterium tumefaciens* containing an expression vector comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS medium with 4.56 μM zeatin, 67.3 μM vancomycin, 418.9 μM cefotaxime and 171.6 μM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, U.S. Pat. No. 5,563,055 (Townsend et al., issued Oct. 8, 1996), described in brief here. In this method soybean seed is surface sterilized by exposure to chlorine gas evolved in a glass bell jar. Seeds are germinated by plating on 1/10 strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the expression vector comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example XV

Transformation of Monocots to Produce Increased Yield or Abiotic Stress Tolerance Cereal plants such as, but not limited to, corn, wheat, rice, sorghum, or barley, may be transformed with the present polynucleotide sequences, including monocot or eudicot-derived sequences such as those presented in the present Tables, cloned into a vector such as pGA643 and containing a kanamycin-resistance marker, and expressed constitutively under, for example, the CaMV 35S or COR15 promoters, or with tissue-specific or inducible promoters. The expression vectors may be one found in the Sequence Listing, or any other suitable expression vector may be similarly used. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3 \times 10^{-9}$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil (1994)) such as corn, wheat, rice, sorghum (Cassas et al. (1993)), and barley (Wan and Lemeaux (1994)). DNA transfer methods such as the microprojectile method can be used for corn (Fromm et al. (1990); Gordon-Kamm et al. (1990); Ishida (1990)), wheat (Vasil et al. (1992); Vasil et al. (1993); Weeks et al. (1993)), and rice (Christou (1991); Hiei et al. (1994); Aldemita and Hodges (1996); and Hiei et al. (1997)). For most cereal plants, embryogenic cells derived from immature scutellum tissues are the preferred cellular targets for transformation (Hiei et al. (1997); Vasil (1994)). For transforming corn embryogenic cells derived from immature scutellar tissue using microprojectile bombardment, the A188XB73 genotype is the preferred genotype (Fromm et al. (1990); Gordon-Kamm et al. (1990)). After microprojectile bombardment the tissues are selected on phosphinothricin to identify the transgenic embryogenic cells (Gordon-Kamm et al. (1990)). Transgenic plants from transformed host plant cells may be regenerated by standard corn regeneration techniques (Fromm et al. (1990); Gordon-Kamm et al. (1990)).

Example XVI

Expression and Analysis of Increased Yield or Abiotic Stress Tolerance in Non-*Arabidopsis* Species Since G1988 closely-related homologs, derived from various diverse plant species, that have been overexpressed in plants have the same functions of conferring increased yield, similar morphologies, reducing light sensitivity, and increasing abiotic stress tolerance, including tolerance to cold during germination and low nitrogen conditions, it is expected that structurally similar orthologs of the G1988 Glade of polypeptide sequences, including those found in the Sequence Listing, can confer increased yield, and/or increased tolerance to a number of abiotic stresses, including water deprivation, cold, and low nitrogen conditions, relative to control plants. As sequences of the invention have been shown to increase yield or improve stress tolerance in a variety of plant species, it is also expected that these sequences will increase yield of crop or other commercially important plant species.

Northern blot analysis, RT-PCR or microarray analysis of the regenerated, transformed plants may be used to show expression of a polypeptide or the invention and related genes that are capable of inducing abiotic stress tolerance, and/or larger size.

After a eudicot plant, monocot plant or plant cell has been transformed (and the latter plant host cell regenerated into a plant) and shown to have greater size, improved planting density, that is, able to tolerate greater planting density with a coincident increase in yield, improved late season vigor, or improved tolerance to abiotic stress, or produce greater yield relative to a control plant under the stress conditions, the transformed monocot plant may be crossed with itself or a plant from the same line, a non-transformed or wild-type monocot plant, or another transformed monocot plant from a different transgenic line of plants.

The function of specific polypeptides of the invention, including closely-related orthologs, have been analyzed and may be further characterized and incorporated into crop plants. The ectopic overexpression of these sequences may be regulated using constitutive, inducible, or tissue specific regulatory elements. Genes that have been examined and have been shown to modify plant traits (including increasing yield and/or abiotic stress tolerance) encode polypeptides found in the Sequence Listing. In addition to these sequences, it is expected that newly discovered polynucleotide and polypeptide sequences closely related to polynucleotide and polypeptide sequences found in the Sequence Listing can also confer alteration of traits in a similar manner to the sequences found in the Sequence Listing, when transformed into any of a considerable variety of plants of different species, and including dicots and monocots. The polynucleotide and polypeptide sequences derived from monocots (e.g., the rice sequences) may be used to transform both monocot and dicot plants, and those derived from dicots (e.g., the *Arabidopsis* and soy genes) may be used to transform either group, although it is expected that some of these sequences will function best if the gene is transformed into a plant from the same group as that from which the sequence is derived.

As an example of a first step to determine water deprivation-related tolerance, seeds of these transgenic plants may be subjected to germination assays to measure sucrose sensing, severe desiccation or drought. The methods for sucrose sensing, severe desiccation or drought assays are described above. Plants overexpressing sequences of the invention may be found to be more tolerant to high sucrose by having better germination, longer radicles, and more cotyledon expansion.

Sequences of the invention, that is, members of the G1988 Glade, may also be used to generate transgenic plants that are more tolerant to low nitrogen conditions or cold than control plants.

All of these abiotic stress tolerances conferred by G1988 may contribute to increased yield of commercially available plants. However, G1988 overexpressors have been shown to increase yield of plants in the apparent absence of significant of obvious abiotic stress, as evidenced by including increased height, increased early season vigor and estimated stand count, and decreased early season canopy coverage observed in soy plants overexpressing G1988. Thus, it is thus expected that members of the G1988 Glade will improve yield in plants relative to control plants, including in leguminous species, even in the absence of overt abiotic stresses.

Plants that are more tolerant than controls to water deprivation assays, low nitrogen conditions or cold are greener, more vigorous will have better survival rates than controls, or will recover better from these treatments than control plants.

It is expected that the same methods may be applied to identify other useful and valuable sequences of the present polypeptide clades, and the sequences may be derived from a diverse range of species.

REFERENCES CITED

Aldemita and Hodges (1996) *Planta* 199: 612-617
Alia et al. (1998) *Plant J.* 16: 155-161
Altschul (1990) *J. Mol. Biol.* 215: 403-410
Altschul (1993) *J. Mol. Evol.* 36: 290-300
Anderson and Young (1985) "Quantitative Filter Hybridisation", In: Hames and Higgins, ed., *Nucleic Acid Hybridisation, A Practical Approach.* Oxford, IRL Press, 73-111
Ausubel et al. (1997) Short Protocols in Molecular Biology, John Wiley & Sons, New York, N.Y., unit 7.7
Bairoch et al. (1997) *Nucleic Acids Res.* 25: 217-221
Bates et al. (1973) *Plant Soil* 39: 205-207
Bates and Lynch (1996) *Plant Cell Environ.* 19: 529-538
Bechtold and Pelletier (1998) *Methods Mol. Biol.* 82: 259-266
Berger and Kimmel (1987), "Guide to Molecular Cloning Techniques", in Methods in Enzymology, vol. 152, Academic Press, Inc., San Diego, Calif.
Bevan (1984) *Nucleic Acids Res.* 12: 8711-8721
Bhattacharjee et al. (2001) *Proc. Natl. Acad. Sci. USA* 98: 13790-13795
Borden (1998) *Biochem. Cell Biol.* 76: 351-358
Borevitz et al. (2000) *Plant Cell* 12: 2383-2393
Boss and Thomas (2002) *Nature,* 416: 847-850
Bruce et al. (2000) *Plant Cell* 12: 65-79
Cassas et al. (1993) *Proc. Natl. Acad. Sci. USA* 90: 11212-11216
Chase et al. (1993) *Ann. Missouri Bot. Gard.* 80: 528-580
Cheikh et al. (2003) U.S. Patent Application No. 20030101479
Cheng et al. (1992) *Proc Natl Acad Sci USA* 89: 1861-1864
Christou et al. (1987) *Proc. Natl. Acad. Sci. USA* 84: 3962-3966
Christou (1991) *Bio/Technol.* 9:957-962
Christou et al. (1992) *Plant. J.* 2: 275-281
Coruzzi et al. (2001) *Plant Physiol.* 125: 61-64
Coupland (1995) *Nature* 377: 482-483
Crawford (1995) *Plant Cell* 7: 859-886
Daly et al. (2001) *Plant Physiol.* 127: 1328-1333
Daniel-Vedele et al. (1996) *CR Acad Sci Paris* 319: 961-968
Deshayes et al. (1985) *EMBO J.,* 4: 2731-2737
D'Halluin et al. (1992) *Plant Cell* 4: 1495-1505
Donn et al. (1990) in *Abstracts of VIIth International Congress on Plant Cell and Tissue Culture IAPTC,* A2-38: 53
Doolittle, ed. (1996) *Methods in Enzymology,* vol. 266: "Computer Methods for Macromolecular Sequence Analysis" Academic Press, Inc., San Diego, Calif., USA
Draper et al. (1982) *Plant Cell Physiol.* 23: 451-458
Eddy (1996) *Curr. Opin. Str. Biol.* 6: 361-365
Eisen (1998) *Genome Res.* 8: 163-167
Feng and Doolittle (1987) *J. Mol. Evol.* 25: 351-360
Fowler and Thomashow (2002) *Plant Cell* 14: 1675-1690
Fromm et al. (1990) *Bio/Technol.* 8: 833-839
Fu et al. (2001) *Plant Cell* 13: 1791-1802
Gelvin et al. (1990) *Plant Molecular Biology Manual,* Kluwer Academic Publishers
Glantz (2001) Relative risk and risk score, in Primer of Biostatistics. 5$^{th}$ ed., McGraw Hill/Appleton and Lange, publisher.
Gilmour et al. (1998) *Plant J.* 16: 433-442
Gruber et al., in Glick and Thompson (1993) *Methods in Plant Molecular Biology and Biotechnology.* eds., CRC Press, Inc., Boca Raton
Goodrich et al. (1993) *Cell* 75: 519-530
Gordon-Kamm et al. (1990) *Plant Cell* 2: 603-618
Haake et al. (2002) *Plant Physiol.* 130: 639-648
Hain et al. (1985) *Mol. Gen. Genet.* 199: 161-168
Harrison (1999) *Annu. Rev. Plant Physiol. Plant Mol. Biol.* 50: 361-389
Haymes et al. (1985) *Nucleic Acid Hybridization: A Practical Approach,* IRL Press, Washington, D.C.

He et al. (2000) *Transgenic Res.* 9: 223-227
Hein (1990) *Methods Enzymol.* 183: 626-645
Henikoff and Henikoff (1989) *Proc. Natl. Acad. Sci. USA* 89:10915
Henikoff and Henikoff (1991) *Nucleic Acids Res.* 19: 6565-6572
Herrera-Estrella et al. (1983) *Nature* 303: 209
Hiei et al. (1994) *Plant J.* 6:271-282
Hiei et al. (1997) *Plant Mol. Biol.* 35:205-218
Higgins and Sharp (1988) *Gene* 73: 237-244
Higgins et al. (1996) *Methods Enzymol.* 266: 383-402
Hosmer and Lemeshow (1999) Applied Survival Analysis: regression Modeling of Time to Event Data. John Wiley & Sons, Inc. Publisher.
Ishida (1990) *Nature Biotechnol.* 14:745-750
Jaglo et al. (2001) *Plant Physiol.* 127: 910-917
Jang et al. (1997) *Plant Cell* 9: 5-19
Kashima et al. (1985) *Nature* 313: 402-404
Kim et al. (2001) *Plant J.* 25: 247-259
Kimmel (1987) *Methods Enzymol.* 152: 507-511
Klee (1985) *Bio/Technology* 3: 637-642
Klein et al. (1987) *Nature* 327: 70-73
Koornneef et al (1986) *In Tomato Biotechnology*: Alan R. Liss, Inc., 169-178
Ku et al. (2000) *Proc. Natl. Acad. Sci. USA* 97: 9121-9126
Kyozuka and Shimamoto (2002) *Plant Cell Physiol.* 43: 130-135
Leon-Kloosterziel et al. (1996) *Plant Physiol.* 110: 233-240
Lin et al. (1991) *Nature* 353: 569-571
Liu and Zhu (1997) *Proc. Natl. Acad. Sci. USA* 94: 14960-14964
Mandel (1992a) Nature 360: 273-277
Mandel et al. (1992b) *Cell* 71-133-143
Meyers (1995) Molecular Biology and Biotechnology, Wiley VCH, New York, N.Y., p 856-853
Miki et al. (1993) in *Methods in Plant Molecular Biology and Biotechnology*, p. 67-88, Glick and Thompson, eds., CRC Press, Inc., Boca Raton
Mount (2001), in *Bioinformatics: Sequence and Genome Analysis*, Cold Spring Harbor Laboratory Press, Cold Spring Harbor, N.Y., p. 543
Miller et al. (2001) *Plant J.* 28: 169-179
Nandi et al. (2000) *Curr. Biol.* 10: 215-218
Peng et al. (1997) *Genes Development* 11: 3194-3205)
Peng et al. (1999) *Nature* 400: 256-261
Porra et al. (1989) *Biochim. Biophys. Acta:* 975, 384-394
Pourtau et al., (2004) *Planta* 219: 765-772
Putterill et al. (1995) *Cell* 80: 847-857
Ratcliffe et al. (2001) *Plant Physiol.* 126: 122-132
Reeves and Nissen (1990) *J. Biol. Chem.* 265, 8573-8582
Reeves and Nissen (1995) *Prog. Cell Cycle Res.* 1: 339-349
Riechmann et al. (2000a) *Science* 290, 2105-2110
Riechmann, J. L., and Ratcliffe, O. J. (2000b) *Curr. Opin. Plant Biol.* 3, 423-434
Rieger et al. (1976) *Glossary of Genetics and Cytogenetics: Classical and Molecular*, 4th ed., Springer Verlag, Berlin
Robson et al. (2001) *Plant* 28: 619-631
Sadowski et al. (1988) *Nature* 335: 563-564
Saleki et al. (1993) *Plant Physiol.* 101: 839-845
Sambrook et al. (1989) *Molecular Cloning: A Laboratory Manual*, 2nd Ed., Cold Spring Harbor Laboratory, Cold Spring Harbor, N.Y.
Sanford et al. (1987) *Part. Sci. Technol.* 5:27-37
Sanford (1993) *Methods Enzymol.* 217: 483-509
Shpaer (1997) *Methods Mol. Biol.* 70: 173-187
Smeekens (1998) *Curr. Opin. Plant Biol.* 1: 230-234
Smith et al. (1992) *Protein Engineering* 5: 35-51
Soltis et al. (1997) *Ann. Missouri Bot. Gard.* 84: 1-49
Sonnhammer et al. (1997) *Proteins* 28: 405-420
Spencer et al. (1994) *Plant Mol. Biol.* 24: 51-61
Stitt (1999) *Curr. Opin. Plant. Biol.* 2: 178-186
Suzuki et al. (2001) *Plant J.* 28: 409-418
Thompson et al. (1994) *Nucleic Acids Res.* 22: 4673-4680
Torok and Etkin (2001) *Differentiation* 67: 63-71
Tudge (2000) in *The Variety of Life*, Oxford University Press, New York, N.Y. pp. 547-606
Vasil et al. (1992) *Bio/Technol.* 10:667-674
Vasil et al. (1993) *Bio/Technol.* 11:1553-1558
Vasil (1994) *Plant Mol. Biol.* 25: 925-937
Vincentz et al. (1992) *Plant J* 3: 315-324
Wahl and Berger (1987) Methods Enzymol. 152: 399-407
Wan and Lemeaux (1994) *Plant Physiol.* 104: 37-48
Weeks et al. (1993) *Plant Physiol.* 102:1077-1084
Weigel and Nilsson (1995) *Nature* 377: 482-500
Weissbach and Weissbach (1989) *Methods for Plant Molecular Biology*, Academic Press
Wu et al. (1996) *Plant Cell* 8: 617-627
Xin and Browse (1998) *Proc. Natl. Acad. Sci. USA* 95: 7799-7804
Xu et al. (2001) *Proc. Natl. Acad. Sci. USA* 98: 15089-15094
Zhang et al. (1991) *Bio/Technology* 9: 996-997
Zhu et al. (1998) *Plant Cell* 10: 1181-1191

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the Claims. Modifications that become apparent from the foregoing description and accompanying figures fall within the scope of the following Claims.

---

SEQUENCE LISTING

```
<160> NUMBER OF SEQ ID NOS: 70

<210> SEQ ID NO 1
<211> LENGTH: 678
<212> TYPE: DNA
<213> ORGANISM: Arabidopsis thaliana
<220> FEATURE:
<223> OTHER INFORMATION: G1988

<400> SEQUENCE: 1
```

```
atggtgagct tttgcgagct tgtggtgcc gaagctgatc tccattgtgc cgcggactct    60
gccttcctct gccgttcttg tgacgctaag ttccatgcct caaattttct cttcgctcgt   120
catttccggc gtgtcatctg cccaaattgc aaatctctta ctcaaaattt cgtttctggt   180
cctcttcttc cttggcctcc acgaacaaca tgttgttcag aatcgtcgtc ttcttcttgc   240
tgctcgtctc ttgactgtgt ctcaagctcc gagctatcgt caacgacgcg tgacgtaaac   300
agagcgcgag ggagggaaaa cagagtgaat gccaaggccg ttgcggttac ggtggcggat   360
ggcattttg taaattggtg tggtaagtta ggactaaaca gggatttaac aaacgctgtc   420
gtttcatatg cgtctttggc tttggctgtg gagacgaggc aagagcgac gaagagagtg    480
ttcttagcgg cggcgttttg gttcggcgtt aagaacacga cgacgtggca gaatttaaag   540
aaagtagaag atgtgactgg agtttcagct gggatgattc gagcggttga aagcaaattg   600
gcgcgtgcaa tgacgcagca gcttagacgg tggcgcgtgg attcggagga aggatgggct   660
gaaaacgaca acgtttga                                                 678
```

<210> SEQ ID NO 2
<211> LENGTH: 225
<212> TYPE: PRT
<213> ORGANISM: Arabidopsis thaliana
<220> FEATURE:
<223> OTHER INFORMATION: G1988 polypeptide

<400> SEQUENCE: 2

```
Met Val Ser Phe Cys Glu Leu Cys Gly Ala Glu Ala Asp Leu His Cys
 1               5                  10                  15

Ala Ala Asp Ser Ala Phe Leu Cys Arg Ser Cys Asp Ala Lys Phe His
            20                  25                  30

Ala Ser Asn Phe Leu Phe Ala Arg His Phe Arg Arg Val Ile Cys Pro
        35                  40                  45

Asn Cys Lys Ser Leu Thr Gln Asn Phe Val Ser Gly Pro Leu Leu Pro
    50                  55                  60

Trp Pro Pro Arg Thr Thr Cys Cys Ser Glu Ser Ser Ser Ser Ser Cys
65                  70                  75                  80

Cys Ser Ser Leu Asp Cys Val Ser Ser Glu Leu Ser Ser Thr Thr
            85                  90                  95

Arg Asp Val Asn Arg Ala Arg Gly Arg Glu Asn Arg Val Asn Ala Lys
        100                 105                 110

Ala Val Ala Val Thr Val Ala Asp Gly Ile Phe Val Asn Trp Cys Gly
    115                 120                 125

Lys Leu Gly Leu Asn Arg Asp Leu Thr Asn Ala Val Val Ser Tyr Ala
130                 135                 140

Ser Leu Ala Leu Ala Val Glu Thr Arg Pro Arg Ala Thr Lys Arg Val
145                 150                 155                 160

Phe Leu Ala Ala Ala Phe Trp Phe Gly Val Lys Asn Thr Thr Thr Trp
            165                 170                 175

Gln Asn Leu Lys Lys Val Glu Asp Val Thr Gly Val Ser Ala Gly Met
        180                 185                 190

Ile Arg Ala Val Glu Ser Lys Leu Ala Arg Ala Met Thr Gln Gln Leu
    195                 200                 205

Arg Arg Trp Arg Val Asp Ser Glu Glu Gly Trp Ala Glu Asn Asp Asn
210                 215                 220

Val
225
```

<210> SEQ ID NO 3
<211> LENGTH: 732
<212> TYPE: DNA
<213> ORGANISM: Glycine max
<220> FEATURE:
<223> OTHER INFORMATION: G4004

<400> SEQUENCE: 3

```
atgaagccca agacttgcga gctttgtcat caactagctt ctctctattg tccctccgat      60
tccgcatttc tctgcttcca ctgcgacgcc gccgtccacg ccgccaactt cctcgtagct     120
cgccacctcc gccgcctcct ctgctccaaa tgcaaccgtt tcgccgcaat tcacatctcc     180
ggtgctatat cccgccacct ctcctccacc tgcacctctt gctccctgga gattccttcc     240
gccgactccg attctctccc ttcctcttct acctgcgtct ccagttccga gtcttgctct     300
acgaatcaga ttaaggcgga agaagagagg aggaggagga ggaggagttt ctcgagttcc     360
tccgtgaccg acgacgcatc tccggcggcg aagaagcggc ggagaaatgg cggatcggtg     420
gcggaggtgt ttgagaaatg gagcagagag atagggttag ggttagggt gaacggaaat      480
cgcgtggcgt cgaacgctct gagtgtgtgc ctcggaaagt ggaggtcgct tccgttcagg     540
gtggctgctg cgacgtcgtt ttggttgggg ctgagatttt gtggggacag aggcctcgcc     600
acgtgtcaga atctggcgag gttggaggca atatctggag tgccagcaaa gctgattctg     660
ggcgcacatg ccaacctcgc acgtgtcttc acgcaccgcc gcgaattgca ggaaggatgg     720
ggcgagtcct ag                                                          732
```

<210> SEQ ID NO 4
<211> LENGTH: 243
<212> TYPE: PRT
<213> ORGANISM: Glycine max
<220> FEATURE:
<223> OTHER INFORMATION: G4004 polypeptide

<400> SEQUENCE: 4

```
Met Lys Pro Lys Thr Cys Glu Leu Cys His Gln Leu Ala Ser Leu Tyr
1               5                   10                  15

Cys Pro Ser Asp Ser Ala Phe Leu Cys Phe His Cys Asp Ala Ala Val
                20                  25                  30

His Ala Ala Asn Phe Leu Val Ala Arg His Leu Arg Arg Leu Leu Cys
            35                  40                  45

Ser Lys Cys Asn Arg Phe Ala Ala Ile His Ile Ser Gly Ala Ile Ser
        50                  55                  60

Arg His Leu Ser Ser Thr Cys Thr Ser Cys Ser Leu Glu Ile Pro Ser
65                  70                  75                  80

Ala Asp Ser Asp Ser Leu Pro Ser Ser Ser Thr Cys Val Ser Ser Ser
                85                  90                  95

Glu Ser Cys Ser Thr Asn Gln Ile Lys Ala Glu Lys Arg Arg Arg Arg
            100                 105                 110

Arg Arg Arg Ser Phe Ser Ser Ser Val Thr Asp Asp Ala Ser Pro
        115                 120                 125

Ala Ala Lys Lys Arg Arg Arg Asn Gly Gly Ser Val Ala Glu Val Phe
    130                 135                 140

Glu Lys Trp Ser Arg Glu Ile Gly Leu Gly Leu Gly Val Asn Gly Asn
145                 150                 155                 160

Arg Val Ala Ser Asn Ala Leu Ser Val Cys Leu Gly Lys Trp Arg Ser
                165                 170                 175

Leu Pro Phe Arg Val Ala Ala Ala Thr Ser Phe Trp Leu Gly Leu Arg
```

180             185             190
Phe Cys Gly Asp Arg Gly Leu Ala Thr Cys Gln Asn Leu Ala Arg Leu
        195                 200                 205

Glu Ala Ile Ser Gly Val Pro Ala Lys Leu Ile Leu Gly Ala His Ala
    210                 215                 220

Asn Leu Ala Arg Val Phe Thr His Arg Arg Glu Leu Gln Glu Gly Trp
225                 230                 235                 240

Gly Glu Ser

<210> SEQ ID NO 5
<211> LENGTH: 726
<212> TYPE: DNA
<213> ORGANISM: Glycine max
<220> FEATURE:
<223> OTHER INFORMATION: G4005

<400> SEQUENCE: 5
atgaagggta agacttgcga gctttgtgat caacaagctt ctctctattg tccctccgat    60
tccgcatttc tctgctccga ctgcgacgcc gccgtgcacg ccgccaactt tctcgtagct   120
cgtcacctcc gtcgcctcct ctgctccaaa tgcaaccgtt tcgccggatt tcacatctcc   180
tccggcgcta tatcccgcca cctctcgtcc acctgcagct cttgctcccc ggagaatcct   240
tccgctgact actccgattc tctcccttcc tcttctacct cgtgtccag ttccgagtct   300 tgctccacga agcagattaa ggcggagaag aagaggagtt ggtcgggttc ctccgtgacc   360
gacgacgcat tccggcggc gaagaagcgg cagaggagtg aggatcgga ggaggtgttt    420 gagaaatgga gcagagagat agggttaggg ttagggttag ggtaaacgg aaatcgcgtg   480 gcgtcgaacg ctctgagtgt gtgcctggga agtggaggt ggcttccgtt cagggtggct   540
gctgcgacgt cgttttggtt ggggctgaga ttttgtgggg acagagggct ggcctcgtgt   600
cagaatctgg cgaggttgga ggcaatatcc ggagtgccag ttaagctgat tctggccgca   660
catggcgacc tggcacgtgt cttcacgcac cgccgcgaat gcaggaagg atggggcgag   720 tcctag                                                             726

<210> SEQ ID NO 6
<211> LENGTH: 241
<212> TYPE: PRT
<213> ORGANISM: Glycine max
<220> FEATURE:
<223> OTHER INFORMATION: G4005  polypeptide

<400> SEQUENCE: 6

Met Lys Gly Lys Thr Cys Glu Leu Cys Asp Gln Gln Ala Ser Leu Tyr
1               5                   10                  15

Cys Pro Ser Asp Ser Ala Phe Leu Cys Ser Asp Cys Asp Ala Ala Val
            20                  25                  30

His Ala Ala Asn Phe Leu Val Ala Arg His Leu Arg Arg Leu Leu Cys
        35                  40                  45

Ser Lys Cys Asn Arg Phe Ala Gly Phe His Ile Ser Ser Gly Ala Ile
    50                  55                  60

Ser Arg His Leu Ser Ser Thr Cys Ser Ser Cys Ser Pro Glu Asn Pro
65                  70                  75                  80

Ser Ala Asp Tyr Ser Asp Ser Leu Pro Ser Ser Thr Cys Val Ser
            85                  90                  95

Ser Ser Glu Ser Cys Ser Thr Lys Gln Ile Lys Ala Glu Lys Lys Arg
            100                 105                 110

```
Ser Trp Ser Gly Ser Ser Val Thr Asp Asp Ala Ser Pro Ala Ala Lys
            115                 120                 125

Lys Arg Gln Arg Ser Gly Gly Ser Glu Glu Val Phe Glu Lys Trp Ser
            130                 135                 140

Arg Glu Ile Gly Leu Gly Leu Gly Leu Gly Val Asn Gly Asn Arg Val
145                 150                 155                 160

Ala Ser Asn Ala Leu Ser Val Cys Leu Gly Lys Trp Arg Trp Leu Pro
                165                 170                 175

Phe Arg Val Ala Ala Ala Thr Ser Phe Trp Leu Gly Leu Arg Phe Cys
                180                 185                 190

Gly Asp Arg Gly Leu Ala Ser Cys Gln Asn Leu Ala Arg Leu Glu Ala
                195                 200                 205

Ile Ser Gly Val Pro Val Lys Leu Ile Leu Ala Ala His Gly Asp Leu
210                 215                 220

Ala Arg Val Phe Thr His Arg Glu Leu Gln Glu Gly Trp Gly Glu
225                 230                 235                 240

Ser
```

<210> SEQ ID NO 7
<211> LENGTH: 709
<212> TYPE: DNA
<213> ORGANISM: Zea mays
<220> FEATURE:
<223> OTHER INFORMATION: G4000

<400> SEQUENCE: 7

```
gacgtcggga atgggcgctg ctcgtgactc cgcggcggcg ggccagaagc acggcaccgg    60
cacgcggtgc gagctctgcg ggggcgcggc ggccgtgcac tgcgccgcgg actcggcgtt   120
cctctgcctg cgctgcgacg ccaaggtgca cggcgccaac ttcctggcgt ccaggcacgt   180
gaggcggcgc ctggtgccgc gccgggccgc cgaccccgag cgtcgtcgg ccgcgtccag    240
cggctcctcc tgcgtgtcca cggccgactc cgcggagtcg gccgccacgg caccggctcc   300
gtgcccttcg aggacggcgg ggaggagggc tccggctcgt gcgcggcggc cgcgcgcgga   360
ggcggtcctg gaggggtggg ccaagcggat ggggttcgcg gcggggccgg cgcgccggcg   420
cgccgcggcg gcggccgccg cgctccgggc gctcggccgg ggcgtggccg ctgcccgcgt   480
gccgctccgc gtcgggatgg ccggcgcgct ctggtcggag gtcgccgccg ggtgccgagg   540
caatggaggg gaggaggcct cgctgctcca gcggctggag gccgccgcgc acgtgccggc   600
gcggctggtg ctgaccgccg cgtcgtggat ggcgcgccgg ccggacgccc ggcaggagga   660
ccacgaggag ggatgggccg agtgctcctg agttcctgat ccagacggg               709
```

<210> SEQ ID NO 8
<211> LENGTH: 226
<212> TYPE: PRT
<213> ORGANISM: Zea mays
<220> FEATURE:
<223> OTHER INFORMATION: G4000 polypeptide

<400> SEQUENCE: 8

```
Met Gly Ala Ala Arg Asp Ser Ala Ala Ala Gly Gln Lys His Gly Thr
1               5                   10                  15

Gly Thr Arg Cys Glu Leu Cys Gly Gly Ala Ala Val His Cys Ala
            20                  25                  30

Ala Asp Ser Ala Phe Leu Cys Leu Arg Cys Asp Ala Lys Val His Gly
            35                  40                  45

Ala Asn Phe Leu Ala Ser Arg His Val Arg Arg Arg Leu Val Pro Arg
```

```
            50                  55                  60
Arg Ala Ala Asp Pro Glu Ala Ser Ser Ala Ala Ser Ser Gly Ser Ser
65                  70                  75                  80

Cys Val Ser Thr Ala Asp Ser Ala Glu Ser Ala Ala Thr Ala Pro Ala
                85                  90                  95

Pro Cys Pro Ser Arg Thr Ala Gly Arg Arg Ala Pro Ala Arg Ala Arg
            100                 105                 110

Arg Pro Arg Ala Glu Ala Val Leu Glu Gly Trp Ala Lys Arg Met Gly
        115                 120                 125

Phe Ala Ala Gly Pro Ala Arg Arg Arg Ala Ala Ala Ala Ala Ala Ala
    130                 135                 140

Leu Arg Ala Leu Gly Arg Gly Val Ala Ala Arg Val Pro Leu Arg
145                 150                 155                 160

Val Gly Met Ala Gly Ala Leu Trp Ser Glu Val Ala Ala Gly Cys Arg
                165                 170                 175

Gly Asn Gly Gly Glu Glu Ala Ser Leu Leu Gln Arg Leu Glu Ala Ala
            180                 185                 190

Ala His Val Pro Ala Arg Leu Val Leu Thr Ala Ala Ser Trp Met Ala
        195                 200                 205

Arg Arg Pro Asp Ala Arg Gln Glu Asp His Glu Glu Gly Trp Ala Glu
    210                 215                 220

Cys Ser
225

<210> SEQ ID NO 9
<211> LENGTH: 732
<212> TYPE: DNA
<213> ORGANISM: Citrus sinensis
<220> FEATURE:
<223> OTHER INFORMATION: G4007

<400> SEQUENCE: 9
atgaaacgag cttgcgagct tgcagccaa gaagcggccc tccactgcgc ttccgacgaa     60
gccttccttt gtttcgactg cgacgatagg gttcataagg ccaactttct cgtggctcgt    120
cacgttcgtc aaactctgtg ctctcagtgc aaatctttga ccggaaagtt catctccggt    180
gaacgttcat cgtcatcgct ggtacccatt tgcccgtctt gttgttcttc tactacttcg    240
acgtcgtctg attgtatttc ttcaactgaa agctccgctg cggagaaaat gggcagagaa    300
cgtaaaaggg ttcgtgcatg ttcgagttct gtgtcggata tttccggcga aaaggcggcg    360
gctgtgacgg attccaaggc ggagggtatt tttgcgattt ggtgtaggag ctggggctg     420
aatggtaata atagtaattg taattcggtt gttgttgtct cttttggcga gtcggcgctg    480
gggttgtgtt tggaaaggac gacggcgttg cccttacggg cttgcttggc ggcgtcgttt    540
tggtttggtc tgagaatgtg cggggacaaa acggtcgcca cgtggccgaa tctgagaagg    600
cttgaggcga tatcaggagt gccggcgaag ttgatcgtgg ccgttgaggg gaagatcgcg    660
cgtgtgatgg cggtgagaag gagaagaccc aggcaggtct ggaggaagg atgggctgag    720
tgcaacgtat ga                                                       732

<210> SEQ ID NO 10
<211> LENGTH: 243
<212> TYPE: PRT
<213> ORGANISM: Citrus sinensis
<220> FEATURE:
<223> OTHER INFORMATION: G4007 polypeptide

<400> SEQUENCE: 10
```

Met Lys Arg Ala Cys Glu Leu Cys Ser Gln Glu Ala Ala Leu His Cys
1               5                   10                  15

Ala Ser Asp Glu Ala Phe Leu Cys Phe Asp Cys Asp Asp Arg Val His
            20                  25                  30

Lys Ala Asn Phe Leu Val Ala Arg His Val Arg Gln Thr Leu Cys Ser
        35                  40                  45

Gln Cys Lys Ser Leu Thr Gly Lys Phe Ile Ser Gly Glu Arg Ser Ser
50                  55                  60

Ser Ser Leu Val Pro Ile Cys Pro Ser Cys Cys Ser Ser Thr Thr Ser
65                  70                  75                  80

Thr Ser Ser Asp Cys Ile Ser Ser Thr Glu Ser Ser Ala Ala Glu Lys
                85                  90                  95

Met Gly Arg Glu Arg Lys Arg Val Arg Ala Cys Ser Ser Ser Val Ser
            100                 105                 110

Asp Ile Ser Gly Glu Lys Ala Ala Ala Val Thr Asp Ser Lys Ala Glu
        115                 120                 125

Gly Ile Phe Ala Ile Trp Cys Arg Arg Leu Gly Leu Asn Gly Asn Asn
    130                 135                 140

Ser Asn Cys Asn Ser Val Val Val Ser Leu Ala Ser Arg Ala Leu
145                 150                 155                 160

Gly Leu Cys Leu Glu Arg Thr Thr Ala Leu Pro Leu Arg Ala Cys Leu
                165                 170                 175

Ala Ala Ser Phe Trp Phe Gly Leu Arg Met Cys Gly Asp Lys Thr Val
            180                 185                 190

Ala Thr Trp Pro Asn Leu Arg Arg Leu Glu Ala Ile Ser Gly Val Pro
        195                 200                 205

Ala Lys Leu Ile Val Ala Val Glu Gly Lys Ile Ala Arg Val Met Ala
    210                 215                 220

Val Arg Arg Arg Pro Arg Gln Val Leu Glu Glu Gly Trp Ala Glu
225                 230                 235                 240

Cys Asn Val

<210> SEQ ID NO 11
<211> LENGTH: 750
<212> TYPE: DNA
<213> ORGANISM: Populus trichocarpa
<220> FEATURE:
<223> OTHER INFORMATION: G4009

<400> SEQUENCE: 11
atggctgtta aggtctgcga gctttgcaaa ggagaagctg gtgtctactg cgattcagat      60
gctgcgtatc tttgttttga ctgtgattct aacgtccata atgctaactt ccttgttgct     120
cgccatattc gccgtgtaat ctgctccggt tgcggttcta tcacaggaaa tccgttctcc     180
ggcgacaccc catctcttag ccgtgtcacc tgttcctctt gctcgccagg aaacaaagaa     240
ctggactcca tctcctgctc ctcctctagt actttatcct ctgcttgcat tcaagcacc      300
gaaacgacgc gctttgagaa cacaagaaaa ggagtcaaga ccacgtcatc ttccagctcg     360
gtgaggaata ttccgggtag atccttgagg gataggttga agaggtcgag gaatctgagg     420
tcagagggtg ttttcgtgaa ttggtgcaaa aggctgggc tcaatggtag tttggtggta     480
cagagagcca ctcgggcgat ggcgctgtgt tttgggagat tggctttgcc gttcagagtg     540
agcttagcgg cgtcgttttg gttcgggctc aggttatgtg gggacaagtc ggttacgacg     600
tgggagaatc tgaggagatt agaggaggta tctgggggttc ccaataagct gatcgttacc     660

```
gttgaaatga agatagaaca ggcgttgcga agcaagagac tgcagctgca gaaagaaatg      720
gaagaagggt gggctgagtg ctctgtgtga                                        750
```

<210> SEQ ID NO 12
<211> LENGTH: 249
<212> TYPE: PRT
<213> ORGANISM: Populus trichocarpa
<220> FEATURE:
<223> OTHER INFORMATION: G4009 polypeptide

<400> SEQUENCE: 12

```
Met Ala Val Lys Val Cys Glu Leu Cys Lys Gly Glu Ala Gly Val Tyr
1               5                   10                  15

Cys Asp Ser Asp Ala Ala Tyr Leu Cys Phe Asp Cys Asp Ser Asn Val
            20                  25                  30

His Asn Ala Asn Phe Leu Val Ala Arg His Ile Arg Arg Val Ile Cys
        35                  40                  45

Ser Gly Cys Gly Ser Ile Thr Gly Asn Pro Phe Ser Gly Asp Thr Pro
    50                  55                  60

Ser Leu Ser Arg Val Thr Cys Ser Ser Cys Ser Pro Gly Asn Lys Glu
65                  70                  75                  80

Leu Asp Ser Ile Ser Cys Ser Ser Ser Thr Leu Ser Ser Ala Cys
            85                  90                  95

Ile Ser Ser Thr Glu Thr Thr Arg Phe Glu Asn Thr Arg Lys Gly Val
            100                 105                 110

Lys Thr Thr Ser Ser Ser Ser Val Arg Asn Ile Pro Gly Arg Ser
        115                 120                 125

Leu Arg Asp Arg Leu Lys Arg Ser Arg Asn Leu Arg Ser Glu Gly Val
    130                 135                 140

Phe Val Asn Trp Cys Lys Arg Leu Gly Leu Asn Gly Ser Leu Val Val
145                 150                 155                 160

Gln Arg Ala Thr Arg Ala Met Ala Leu Cys Phe Gly Arg Leu Ala Leu
                165                 170                 175

Pro Phe Arg Val Ser Leu Ala Ala Ser Phe Trp Phe Gly Leu Arg Leu
            180                 185                 190

Cys Gly Asp Lys Ser Val Thr Thr Trp Glu Asn Leu Arg Arg Leu Glu
        195                 200                 205

Glu Val Ser Gly Val Pro Asn Lys Leu Ile Val Thr Val Glu Met Lys
    210                 215                 220

Ile Glu Gln Ala Leu Arg Ser Lys Arg Leu Gln Leu Gln Lys Glu Met
225                 230                 235                 240

Glu Glu Gly Trp Ala Glu Cys Ser Val
                245
```

<210> SEQ ID NO 13
<211> LENGTH: 726
<212> TYPE: DNA
<213> ORGANISM: Oryza sativa
<220> FEATURE:
<223> OTHER INFORMATION: G4011

<400> SEQUENCE: 13

```
atgggtggcg aggcggagcg gtgcgcgctc tgtggcgcgg cggcggcggt gcactgcgag      60
gcggacgcgg cgttcctgtg cgcggcgtgc gacgccaagg tgcacggggc gaacttcctc     120
gcgtcgcggc accaccggag gcgggtggcg ccggggcgg tggtggtggt ggaggtggag      180
gaggaggagg ggtatgagtc cggggcgtcg gcggcgtcga gcacgtcgtg cgtgtcgacg     240
```

```
gccgactccg acgtggcggc gtcggcggcg gcgaggcggg ggaggaggag gaggccgagg    300
gcagcggcgc ggccccgcgc ggaggtggtt ctcgaggggt ggggcaagcg gatgggcctc    360
gcggcggggg cggcgcggcg gcgcgccgcg gcggccgggc gcgcgctccg ggcgtgcggc    420
ggggacgtcg ccgccgcgcg cgtcccgctc cgcgtcgcca tggcggccgc gctgtggtgg    480
gaggtggcgg cccaccgcgt ctccggcgtc tccggcgccg ccatgccga cgcgctgcgg     540 cggctggagg cgtgcgcgca cgtgccggcg aggctgctca cggcggtggc gtcgtcgatg    600
gcccgcgcgc gcgcaaggcg gcgcgccgcc gcggacaacg aggagggctg ggacgagtgc    660
tcgtgttctg aagcgcccaa cgccttgggt ggcccacatg tcagtgacac agctcgtcag    720
aaatga                                                              726
```

<210> SEQ ID NO 14
<211> LENGTH: 241
<212> TYPE: PRT
<213> ORGANISM: Oryza sativa
<220> FEATURE:
<223> OTHER INFORMATION: G4011 polypeptide

<400> SEQUENCE: 14

```
Met Gly Gly Glu Ala Glu Arg Cys Ala Leu Cys Gly Ala Ala Ala
1               5                   10                  15

Val His Cys Glu Ala Asp Ala Ala Phe Leu Cys Ala Ala Cys Asp Ala
            20                  25                  30

Lys Val His Gly Ala Asn Phe Leu Ala Ser Arg His His Arg Arg Arg
        35                  40                  45

Val Ala Ala Gly Ala Val Val Val Glu Val Glu Glu Glu Gly
    50                  55                  60

Tyr Glu Ser Gly Ala Ser Ala Ala Ser Ser Thr Ser Cys Val Ser Thr
65                  70                  75                  80

Ala Asp Ser Asp Val Ala Ala Ser Ala Ala Arg Arg Gly Arg Arg
                85                  90                  95

Arg Arg Pro Arg Ala Ala Ala Arg Pro Arg Ala Glu Val Val Leu Glu
            100                 105                 110

Gly Trp Gly Lys Arg Met Gly Leu Ala Ala Gly Ala Ala Arg Arg Arg
        115                 120                 125

Ala Ala Ala Ala Gly Arg Ala Leu Arg Ala Cys Gly Gly Asp Val Ala
    130                 135                 140

Ala Ala Arg Val Pro Leu Arg Val Ala Met Ala Ala Leu Trp Trp
145                 150                 155                 160

Glu Val Ala Ala His Arg Val Ser Gly Val Ser Gly Ala Gly His Ala
                165                 170                 175

Asp Ala Leu Arg Arg Leu Glu Ala Cys Ala His Val Pro Ala Arg Leu
            180                 185                 190

Leu Thr Ala Val Ala Ser Ser Met Ala Arg Ala Arg Arg Arg
        195                 200                 205

Ala Ala Ala Asp Asn Glu Glu Gly Trp Asp Glu Cys Ser Cys Ser Glu
    210                 215                 220

Ala Pro Asn Ala Leu Gly Gly Pro His Val Ser Asp Thr Ala Arg Gln
225                 230                 235                 240

Lys
```

<210> SEQ ID NO 15
<211> LENGTH: 666
<212> TYPE: DNA
<213> ORGANISM: Oryza sativa

<220> FEATURE:
<223> OTHER INFORMATION: G4012

<400> SEQUENCE: 15

```
atggaggtcg gcaacggcaa gtgcggcggt ggtggcgccg ggtgcgagct gtgcggggc      60
gtggccgcgg tgcactgcgc cgctgactcc gcgtttcttt gcttggtatg tgacgacaag    120
gtgcacggcg ccaacttcct cgcgtccagg caccgccgcc gccggttggg ggttgaggtg    180
gtggatgagg aggatgacgc ccggtccacg gcgtcgagct cgtgcgtgtc gacggcggac    240
tccgcgtcgt ccacggcggc ggcggctgcg ctggagagcg aggacgtcag gaggaggggg    300
cggcgcgggc ggcgtgcccc gcgcgcggag gcggttctgg aggggtgggc gaagcggatg    360
gggttgtcgt cgggcgcggc gcgcaggcgc gccgccgcgg ccggggcggc gctccgcgcg    420
gtgggccgtg gcgtcgccgc ctcccgcgtc ccgatccgcg tcgcgatggc cgccgcgctc    480
tggtcggagg tcgcctcctc ctcctcccgt cgccgccgcc gccccggcgc cggacaggcc    540
gcgctgctcc tgcggctgga ggccagcgcg cacgtgccgg cgaggctgct cctgacggtg    600
gcgtcgtgga tggcgcgcgc gtcgacgccg cccgccgccg aggagggctg ggccgagtgc    660
tcctga                                                              666
```

<210> SEQ ID NO 16
<211> LENGTH: 221
<212> TYPE: PRT
<213> ORGANISM: Oryza sativa
<220> FEATURE:
<223> OTHER INFORMATION: G4012 polypeptide

<400> SEQUENCE: 16

```
Met Glu Val Gly Asn Gly Lys Cys Gly Gly Gly Ala Gly Cys Glu
1               5                   10                  15

Leu Cys Gly Gly Val Ala Ala His Cys Ala Ala Asp Ser Ala Phe
                20                  25                  30

Leu Cys Leu Val Cys Asp Asp Lys Val His Gly Ala Asn Phe Leu Ala
            35                  40                  45

Ser Arg His Arg Arg Arg Leu Gly Val Glu Val Asp Glu Glu
        50                  55                  60

Asp Asp Ala Arg Ser Thr Ala Ser Ser Ser Cys Val Ser Thr Ala Asp
65                  70                  75                  80

Ser Ala Ser Ser Thr Ala Ala Ala Ala Leu Glu Ser Glu Asp Val
                85                  90                  95

Arg Arg Arg Gly Arg Arg Gly Arg Ala Pro Arg Ala Glu Ala Val
            100                 105                 110

Leu Glu Gly Trp Ala Lys Arg Met Gly Leu Ser Ser Gly Ala Ala Arg
            115                 120                 125

Arg Arg Ala Ala Ala Gly Ala Ala Leu Arg Ala Val Gly Arg Gly
        130                 135                 140

Val Ala Ala Ser Arg Val Pro Ile Arg Val Ala Met Ala Ala Ala Leu
145                 150                 155                 160

Trp Ser Glu Val Ala Ser Ser Ser Arg Arg Arg Arg Pro Gly
                165                 170                 175

Ala Gly Gln Ala Ala Leu Leu Leu Arg Leu Glu Ala Ser Ala His Val
            180                 185                 190

Pro Ala Arg Leu Leu Leu Thr Val Ala Ser Trp Met Ala Arg Ala Ser
        195                 200                 205

Thr Pro Pro Ala Ala Glu Glu Gly Trp Ala Glu Cys Ser
            210                 215                 220
```

<210> SEQ ID NO 17
<211> LENGTH: 893
<212> TYPE: DNA
<213> ORGANISM: Zea mays
<220> FEATURE:
<223> OTHER INFORMATION: G4297

<400> SEQUENCE: 17

```
cggacgcgtg gcggacgcg tgggcggacg cgtgggcctg gagggtgcaa gggagggagg      60
cggtcggact agttctaggg cggtcgaatc cgccagcgca tccgctgagc accgccagcc    120
ccgcacgcgg aggtcggagg gctacgctcc ggagtccgag gggaaggcag aggaggcaag    180
caggcaggat gggtgccgct ggtgacgccg cggcagcggg cacgcggtgc gagctctgcg    240
ggggcgcggc ggccgtgcac tgcgccgcgg actcggcgtt cctctgcccg cgctgcgacg    300
ccaaggtgca cggcgccaac ttcctggcgt ccaggcacgt gaggcgccgc ctgccgcgcg    360
ggggcgccga ctccggggcg tccgcgtcca gcggctcctg cctgtccacg gccgactccg    420
tgcagtcgag gcggcgccg ccgccaggga gaggcagagg gaggagggcg ccgccgcgcg    480
cggaggcggt gctggagggg tgggccagga ggaaggggt cgcggcgggg cccgcgtgcc    540
gtcgtcgcgt cccgctccgc gtcgcgatgg ccgccgcgcg ctggtcggag gtcagcgccg    600
gcggtggagc ggaggctgcg gtgctcgcag ttgcggcgtg gtggatgacg cgcgcggcga    660
gagcgagacc cccggcggcg ggcgctccgg acctggagga gggatgggcc gagtgctctc    720
ctgaattcgt ggtccggcag ggcccacatc cgtctgcaac aacatgtggg cgacgttagt    780
ttgtcctttt cctccctaat tatttagta attaacgaga tcgatcgtgt ggtggtggtg    840
tcgttggctt cctctcgtcg tccgattaac aaaagccggt tcgatttgat tac          893
```

<210> SEQ ID NO 18
<211> LENGTH: 196
<212> TYPE: PRT
<213> ORGANISM: Zea mays
<220> FEATURE:
<223> OTHER INFORMATION: G4297 polypeptide

<400> SEQUENCE: 18

Met Gly Ala Ala Gly Asp Ala Ala Ala Gly Thr Arg Cys Glu Leu
1               5                   10                  15

Cys Gly Gly Ala Ala Ala Val His Cys Ala Ala Asp Ser Ala Phe Leu
            20                  25                  30

Cys Pro Arg Cys Asp Ala Lys Val His Gly Ala Asn Phe Leu Ala Ser
        35                  40                  45

Arg His Val Arg Arg Leu Pro Arg Gly Gly Ala Asp Ser Gly Ala
    50                  55                  60

Ser Ala Ser Ser Gly Ser Cys Leu Ser Thr Ala Asp Ser Val Gln Ser
65                  70                  75                  80

Arg Ala Ala Pro Pro Gly Arg Gly Arg Gly Arg Ala Pro Pro
                85                  90                  95

Arg Ala Glu Ala Val Leu Glu Gly Trp Ala Arg Lys Gly Val Ala
                100                 105                 110

Ala Gly Pro Ala Cys Arg Arg Val Pro Leu Arg Val Ala Met Ala
            115                 120                 125

Ala Ala Arg Trp Ser Glu Val Ser Ala Gly Gly Ala Glu Ala Ala
        130                 135                 140

Val Leu Ala Val Ala Ala Trp Trp Met Thr Arg Ala Ala Arg Ala Arg
145                 150                 155                 160

```
Pro Pro Ala Ala Gly Ala Pro Asp Leu Glu Glu Gly Trp Ala Glu Cys
            165                 170                 175

Ser Pro Glu Phe Val Val Arg Gln Gly Pro His Pro Ser Ala Thr Thr
        180                 185                 190

Cys Gly Arg Arg
        195

<210> SEQ ID NO 19
<211> LENGTH: 1094
<212> TYPE: DNA
<213> ORGANISM: Oryza sativa
<220> FEATURE:
<223> OTHER INFORMATION: G4298

<400> SEQUENCE: 19
gcacgaggcc tcgtgccgaa ttcgggacgg cgccagcgtc tcgctcccaa gccagacctc      60
cccctcgcc gtccgcgcgc gcgcccgcgg tttccccgc tcgccgccgg tttccccgc        120
tcgccgccgg tttcccgaa gcgcgccgcg cccgcgcctg cgcccgccgg tcgccatcgc      180
catctcgccc tcgcgcggag actggtgtcc ctgttttgct ctgtagtata aagccacgca      240
aaccccgcc aggtgttcga ccgagtgaca caagagtcca gcctcttgca acctgtaatg      300
gaggtcggca acggcaagtg cggcggtggt ggcgccgggt gcgagctgtg cggggggcgtg    360
gccgcggtgc actgcgccgc tgactccgcg tttctttgct tggtatgtga cgacaaggtg     420
cacggcgcca acttcctcgc gtccaggcac cccgccgcc ggtggggcgt tgagctggtg      480
gatgatgggg ggcgcgcccg gcgccgcccc ccgccccgg gggggctgg gccgagtgct       540
cctgatccgc cgccgccgcc ggccaccgca cgacgaatct tccggccgcc tgagatagaa     600
agtactaaaa atgcgaaact tgtgggcaat gattgtttgt ttgcttcctc cctaattaat      660
taaattaatc tcaaattctt aatcaccatc aaggacccaa aaatcttgtg gttaaggaag     720
gcctctcttg tggttaacat caaatcacaa gtctaaatcc aatggatggg actctaattt     780
ttctgtgtag tattagtata ccatgatgat agtacatttg atttgttatt aattggttat    840
taattaaagg tgatttgatc aactagactt tatgtggtca aaaatgctct cctgtattgt     900
atgagtgacc actaccactc gatatttttt tccttccatc ttggctgagt cctgtcttgt    960
gtttgtttat tggtatctca atgtactggg cttaccactt gtatggacag tattgttaca   1020
ctaacacagt gtgtacccc cagtcgtgtt agcttgaatg ggaagaccat gatcaaaaaa     1080
aaaaaaaaa aaaa                                                     1094

<210> SEQ ID NO 20
<211> LENGTH: 121
<212> TYPE: PRT
<213> ORGANISM: Oryza sativa
<220> FEATURE:
<223> OTHER INFORMATION: G4298 polypeptide

<400> SEQUENCE: 20

Met Glu Val Gly Asn Gly Lys Cys Gly Gly Gly Ala Gly Cys Glu
1                 5                  10                  15

Leu Cys Gly Gly Val Ala Ala Val His Cys Ala Ala Asp Ser Ala Phe
            20                  25                  30

Leu Cys Leu Val Cys Asp Asp Lys Val His Gly Ala Asn Phe Leu Ala
        35                  40                  45

Ser Arg His Pro Arg Arg Arg Trp Gly Val Glu Leu Val Asp Asp Gly
    50                  55                  60
```

Gly Arg Ala Arg Arg Pro Pro Pro Gly Ala Gly Pro Ser
 65                  70                  75                  80

Ala Pro Asp Pro Pro Pro Pro Ala Thr Ala Arg Arg Ile Phe Arg
                 85                  90                  95

Pro Pro Glu Ile Glu Ser Thr Lys Asn Ala Lys Leu Val Gly Asn Asp
            100                 105                 110

Cys Leu Phe Ala Ser Ser Leu Ile Asn
        115                 120

<210> SEQ ID NO 21
<211> LENGTH: 1662
<212> TYPE: DNA
<213> ORGANISM: Lycopersicon esculentum
<220> FEATURE:
<223> OTHER INFORMATION: G4299

<400> SEQUENCE: 21

| | | | | | |
|---|---|---|---|---|---|
| ttattaaata | ataacaaact | agtcaaatat | tacatctacc | atgtaataca | gtataatata | 60 |
| aatacaatat | gaatcaatgg | ataacaaatg | atccaaatgt | aaatctaaat | gaagataaaa | 120 |
| gagtgaattt | cgcactttt | atatatagag | tggttaactt | ttgagtccac | actccacaat | 180 |
| atggtaaatg | catttatggt | taatacaaag | tccacaacca | caacacttgg | ctttccttca | 240 |
| atctctcctt | tctttccttt | actcaataat | attactggac | actcctcact | ttttcttta | 300 |
| aaccacatat | ataaattcaa | tcaataatac | acttcacaaa | tcattctaaa | gtctaaattc | 360 |
| tcattacgta | gcactctttg | ctatctcacc | ttactcattc | ctcttcctcc | tatatctttt | 420 |
| ctctccgccc | cattttcact | atcacaaatc | aaagcttcca | aaatttagaa | attgtataca | 480 |
| aaaatggaac | ttctgtcctc | taaactctgt | gagctttgca | atgatcaagc | tgctctgttt | 540 |
| tgtccatctg | attcagcttt | tctctgtttt | cactgtgatg | ctaaagttca | tcaggctaat | 600 |
| ttccttgttg | ctcgccacct | tcgtcttact | ctttgctctc | actgtaactc | ccttacgaaa | 660 |
| aaacgttttt | ccccttgttc | accgccgcct | cctgctcttt | gtccttcctg | ttcccggaat | 720 |
| tcgtctggtg | attccgatct | ccgttctgtt | tcaacgacgt | cgtcgtcgtc | ttcgtcgact | 780 |
| tgtgttccca | gcacgcagtc | cagtgctatt | actcaaaaaa | ttaacataat | ctcttcaaat | 840 |
| cgaaagcaat | ttccggacag | cgactctaac | ggtgaagtca | attctggcag | atgtaattta | 900 |
| gtacgatcca | gaagtgtgaa | attgcgagat | ccaagagcgg | cgacttgtgt | gttcatgcat | 960 |
| tggtgcacaa | agcttcaaat | gaaccgcgag | gaacgtgtgg | tgcaaacggc | ttgtagtgtg | 1020 |
| ttgggtattt | gttttagtcg | gtttaggggt | ctgcctctac | gggttgccct | ggcggcctgt | 1080 |
| ttttggtttg | gtttgaaaac | taccgaagac | aaatcaaaga | cgtcgcaatc | tttgaagaaa | 1140 |
| ttagaggaga | tctcgggtgt | gccggcgaag | ataatattag | caacagaatt | aaagcttcga | 1200 |
| aaaataatga | aaaccaacca | cggccaacct | caagcaatgg | aagaaagctg | ggctgaatcc | 1260 |
| tcgcccctaat | tttctttgtt | tttggagaat | attcccacac | ctcttttgat | tttcattttc | 1320 |
| tattttccta | tcttctaaat | ttgtgaaaaa | cattagaaaa | atggaaaagt | ttgaactgga | 1380 |
| aaatccattt | taccacagta | ttttcctttt | gttttcgtt | ttttctacat | ttttatcaag | 1440 |
| ctgttgaaac | cataaagtcc | gtgtcggacc | accggaaaaa | atgaaaaaaa | aattggagga | 1500 |
| agaatcttct | caaggacaa | actaaaagtt | agacccacac | tatataatac | atgggttcaa | 1560 |
| attcaacaaa | aaataatcca | gggttggccc | cccactatta | ataaacttgg | tcaaaaatta | 1620 |
| agttttttaa | aatctggggt | attcacacca | aattttttata | ta | | 1662 |

<210> SEQ ID NO 22

```
<211> LENGTH: 261
<212> TYPE: PRT
<213> ORGANISM: Lycopersicon esculentum
<220> FEATURE:
<223> OTHER INFORMATION: G4299 polypeptide

<400> SEQUENCE: 22

Met Glu Leu Leu Ser Ser Lys Leu Cys Glu Leu Cys Asn Asp Gln Ala
1               5                   10                  15

Ala Leu Phe Cys Pro Ser Asp Ser Ala Phe Leu Cys Phe His Cys Asp
            20                  25                  30

Ala Lys Val His Gln Ala Asn Phe Leu Val Ala Arg His Leu Arg Leu
        35                  40                  45

Thr Leu Cys Ser His Cys Asn Ser Leu Thr Lys Lys Arg Phe Ser Pro
    50                  55                  60

Cys Ser Pro Pro Pro Ala Leu Cys Pro Ser Cys Ser Arg Asn Ser
65                  70                  75                  80

Ser Gly Asp Ser Asp Leu Arg Ser Val Ser Thr Thr Ser Ser Ser Ser
                85                  90                  95

Ser Ser Thr Cys Val Ser Ser Thr Gln Ser Ser Ala Ile Thr Gln Lys
            100                 105                 110

Ile Asn Ile Ile Ser Ser Asn Arg Lys Gln Phe Pro Asp Ser Asp Ser
        115                 120                 125

Asn Gly Glu Val Asn Ser Gly Arg Cys Asn Leu Val Arg Ser Arg Ser
130                 135                 140

Val Lys Leu Arg Asp Pro Arg Ala Ala Thr Cys Val Phe Met His Trp
145                 150                 155                 160

Cys Thr Lys Leu Gln Met Asn Arg Glu Glu Arg Val Val Gln Thr Ala
                165                 170                 175

Cys Ser Val Leu Gly Ile Cys Phe Ser Arg Phe Arg Gly Leu Pro Leu
            180                 185                 190

Arg Val Ala Leu Ala Ala Cys Phe Trp Phe Gly Leu Lys Thr Thr Glu
        195                 200                 205

Asp Lys Ser Lys Thr Ser Gln Ser Leu Lys Lys Leu Glu Glu Ile Ser
    210                 215                 220

Gly Val Pro Ala Lys Ile Ile Leu Ala Thr Glu Leu Lys Leu Arg Lys
225                 230                 235                 240

Ile Met Lys Thr Asn His Gly Gln Pro Gln Ala Met Glu Glu Ser Trp
                245                 250                 255

Ala Glu Ser Ser Pro
            260

<210> SEQ ID NO 23
<211> LENGTH: 522
<212> TYPE: DNA
<213> ORGANISM: Zea mays
<220> FEATURE:
<223> OTHER INFORMATION: G4001

<400> SEQUENCE: 23
atgggcgctg ctcgtgactc cacggcggcg ggccagaagc gcggcaccgg cacgcggtgc        60
gagctctgcg ggggcgcggc ggccgtgcac tgcgccgcgg actcggcgtt cctctgcctg       120
cgctgcgacg ccaaggtgca cggcgccaac ttcctggcgt ccaggcacgt gaggcggcgc       180
ctggtgccgc gccgggccgc cgaccccgag gcgtcgtcgg ccgcgtccag cggctcctcc       240
tgcgtgtcca cggccgactc gcggagtcg gcgccacgg caccggctcc gtgcccttcg        300
aggacggcgg ggaggagggc tccggctcgg gcgcggcggc cgcgcgcgga ggcggtcctg       360
```

```
gaggggtggg ccaagcggat ggggttcgcg gcggggccgg cgcgccggcg cgcacgtgcc        420
ggcgcggctg gtgctgaccg ccgcgtcgtg gatggcgcgc cggccggacg cccggcagga        480
ggaccactag gagggatggg ccgagtgctc ctgagttcct ga                          522
```

```
<210> SEQ ID NO 24
<211> LENGTH: 173
<212> TYPE: PRT
<213> ORGANISM: Zea mays
<220> FEATURE:
<223> OTHER INFORMATION: G4001 polypeptide

<400> SEQUENCE: 24
```

```
Met Gly Ala Ala Arg Asp Ser Thr Ala Ala Gly Gln Lys Arg Gly Thr
1               5                   10                  15

Gly Thr Arg Cys Glu Leu Cys Gly Gly Ala Ala Ala Val His Cys Ala
            20                  25                  30

Ala Asp Ser Ala Phe Leu Cys Leu Arg Cys Asp Ala Lys Val His Gly
        35                  40                  45

Ala Asn Phe Leu Ala Ser Arg His Val Arg Arg Leu Val Pro Arg
    50                  55                  60

Arg Ala Ala Asp Pro Glu Ala Ser Ser Ala Ser Ser Gly Ser Ser
65                  70                  75                  80

Cys Val Ser Thr Ala Asp Ser Ala Glu Ser Ala Ala Thr Ala Pro Ala
                85                  90                  95

Pro Cys Pro Ser Arg Thr Ala Gly Arg Arg Ala Pro Ala Arg Ala Arg
            100                 105                 110

Arg Pro Arg Ala Glu Ala Val Leu Glu Gly Trp Ala Lys Arg Met Gly
        115                 120                 125

Phe Ala Ala Gly Pro Ala Arg Arg Arg Ala Arg Ala Gly Ala Ala Gly
    130                 135                 140

Ala Asp Arg Arg Val Val Asp Gly Ala Pro Ala Gly Arg Pro Ala Gly
145                 150                 155                 160

Gly Pro Leu Gly Gly Met Gly Arg Val Leu Leu Ser Ser
                165                 170
```

```
<210> SEQ ID NO 25
<211> LENGTH: 648
<212> TYPE: DNA
<213> ORGANISM: Arabidopsis thaliana
<220> FEATURE:
<223> OTHER INFORMATION: G900

<400> SEQUENCE: 25
```

```
atggggaaga agaagtgcga gttatgttgt ggtgtagcga aatgtattg tgagtcagat         60 caagcgagtt tatgttggga ttgtgacggt aaagttcacg gagctaattt tctggtggcg       120
aaacacatgc gttgtcttct atgtagcgcg tgtcagtcac acacgccttg aaagcttct        180 gggctgaatc ttggcccaac tgtttctatc tgtgagtctt gtttagctcg taagaagaat       240
aacaacagct ccctcgccgg gagggatcag aatcttaacc aagaagaaga gatcattggt      300
tgtaacgacg gagctgagtc ttatgatgag gaaagcgatg aggatgaaga agaagaagaa       360
gtggagaatc aggttgttcc ggctgcggtg gagcaagaac ttccggtggt gagttcgtcg       420
tcttcggtta gtagtggtga aggagatcag gtggtgaaaa ggacgagact tgatttggat      480 cttaaccctct ccgatgagga gaaccaatct gaccattga aaagattatc gagagacgaa     540
ggtttgtcaa gatcaactgt tgtgatgaat agctcaatcg tgaaattaca cggagggagg       600
```

```
agaaaagcag agggatgtga tacatcatcg tcgtcttcgt tttattga          648
```

<210> SEQ ID NO 26
<211> LENGTH: 215
<212> TYPE: PRT
<213> ORGANISM: Arabidopsis thaliana
<220> FEATURE:
<223> OTHER INFORMATION: G900 polypeptide

<400> SEQUENCE: 26

```
Met Gly Lys Lys Lys Cys Glu Leu Cys Cys Gly Val Ala Arg Met Tyr
1               5                   10                  15

Cys Glu Ser Asp Gln Ala Ser Leu Cys Trp Asp Cys Asp Gly Lys Val
            20                  25                  30

His Gly Ala Asn Phe Leu Val Ala Lys His Met Arg Cys Leu Leu Cys
        35                  40                  45

Ser Ala Cys Gln Ser His Thr Pro Trp Lys Ala Ser Gly Leu Asn Leu
    50                  55                  60

Gly Pro Thr Val Ser Ile Cys Glu Ser Cys Leu Ala Arg Lys Lys Asn
65                  70                  75                  80

Asn Asn Ser Ser Leu Ala Gly Arg Asp Gln Asn Leu Asn Gln Glu Glu
                85                  90                  95

Glu Ile Ile Gly Cys Asn Asp Gly Ala Glu Ser Tyr Asp Glu Glu Ser
            100                 105                 110

Asp Glu Asp Glu Glu Glu Glu Val Glu Asn Gln Val Val Pro Ala
        115                 120                 125

Ala Val Glu Gln Glu Leu Pro Val Val Ser Ser Ser Ser Val Ser
    130                 135                 140

Ser Gly Glu Gly Asp Gln Val Val Lys Arg Thr Arg Leu Asp Leu Asp
145                 150                 155                 160

Leu Asn Leu Ser Asp Glu Glu Asn Gln Ser Arg Pro Leu Lys Arg Leu
                165                 170                 175

Ser Arg Asp Glu Gly Leu Ser Arg Ser Thr Val Val Met Asn Ser Ser
            180                 185                 190

Ile Val Lys Leu His Gly Gly Arg Arg Lys Ala Glu Gly Cys Asp Thr
        195                 200                 205

Ser Ser Ser Ser Ser Phe Tyr
    210                 215
```

<210> SEQ ID NO 27
<211> LENGTH: 1071
<212> TYPE: DNA
<213> ORGANISM: Arabidopsis thaliana
<220> FEATURE:
<223> OTHER INFORMATION: G910

<400> SEQUENCE: 27

```
atgttatgta taataataat tgagaatatg gaaagagtat gtgagttttg taaagcgtat    60
agagcagtgg tttattgtat agctgataca gcaaatcttt gtttaacatg tgatgcaaag   120
gttcattcag ctaattcact ctcgggacgg catttacgta cggttttatg tgattctggt   180
aagaatcagc cttgtgttgt ccgatgtttt gaccataaaa tgtttctttg ccatggatgt   240
aatgataagt tcatggtgg tggctcttct gagcatcgta aagggatttt gaggtgttat   300
acgggttgtc ctcctgctaa agatttcgcg gttatgtggg gttttcgagt tatggatgac   360
gatgatgatg tttcgttaga gcaatctttt cgaatggtta aacctaaggt gcaaagagaa   420
ggtggtttta tcttggaaca gattcttgaa ttggagaagg ttcagctcag ggaagagaat   480
```

```
ggtagttctt ccttgacaga acgaggtgat ccatctccat tggagcttcc taagaaaccc    540
gaagaacagt taatcgatct tccgcagacc ggaaaagagc tggttgttga tttttcacac    600
ttgtcctcat cttccacact tggtgattcc ttttgggaat gcaaaagtcc atacaataag    660
aacaatcagt tgtggcatca aaatatacaa gacattggag tatgtgaaga tacaatctgc    720
agtgacgatg acttccaaat acctgacatt gatctcactt tccggaactt tgaagagcaa    780
tttggagctg atcctgagcc aattgcagat agtaacaacg tgttctttgt ttcttcccct    840
gacaaatcac atgagatgaa gacatttttct tcttcattca ataatcccat atttgcacct    900
aaaccagctt catcaactat ctcattctca agcagtgaaa ccgataaccc ttatagtcac    960
tcagaggaag taatctcatt ttgtccctcc ctctctaaca atacacgtca aaaggtcatc   1020
acaaggctca aggagaagaa gagagcaaga gtggaggaga aaaaagctta a            1071
```

<210> SEQ ID NO 28
<211> LENGTH: 356
<212> TYPE: PRT
<213> ORGANISM: Arabidopsis thaliana
<220> FEATURE:
<223> OTHER INFORMATION: G910 polypeptide

<400> SEQUENCE: 28

```
Met Leu Cys Ile Ile Ile Glu Asn Met Glu Arg Val Cys Glu Phe
1               5                   10                  15

Cys Lys Ala Tyr Arg Ala Val Val Tyr Cys Ile Ala Asp Thr Ala Asn
                20                  25                  30

Leu Cys Leu Thr Cys Asp Ala Lys Val His Ser Ala Asn Ser Leu Ser
            35                  40                  45

Gly Arg His Leu Arg Thr Val Leu Cys Asp Ser Gly Lys Asn Gln Pro
    50                  55                  60

Cys Val Val Arg Cys Phe Asp His Lys Met Phe Leu Cys His Gly Cys
65                  70                  75                  80

Asn Asp Lys Phe His Gly Gly Ser Ser Glu His Arg Arg Arg Asp
                85                  90                  95

Leu Arg Cys Tyr Thr Gly Cys Pro Pro Ala Lys Asp Phe Ala Val Met
            100                 105                 110

Trp Gly Phe Arg Val Met Asp Asp Asp Asp Val Ser Leu Glu Gln
        115                 120                 125

Ser Phe Arg Met Val Lys Pro Lys Val Gln Arg Glu Gly Gly Phe Ile
    130                 135                 140

Leu Glu Gln Ile Leu Glu Leu Glu Lys Val Gln Leu Arg Glu Glu Asn
145                 150                 155                 160

Gly Ser Ser Ser Leu Thr Glu Arg Gly Asp Pro Ser Pro Leu Glu Leu
                165                 170                 175

Pro Lys Lys Pro Glu Glu Gln Leu Ile Asp Leu Pro Gln Thr Gly Lys
            180                 185                 190

Glu Leu Val Val Asp Phe Ser His Leu Ser Ser Ser Thr Leu Gly
        195                 200                 205

Asp Ser Phe Trp Glu Cys Lys Ser Pro Tyr Asn Lys Asn Gln Leu
    210                 215                 220

Trp His Gln Asn Ile Gln Asp Ile Gly Val Cys Glu Asp Thr Ile Cys
225                 230                 235                 240

Ser Asp Asp Asp Phe Gln Ile Pro Asp Ile Asp Leu Thr Phe Arg Asn
                245                 250                 255

Phe Glu Glu Gln Phe Gly Ala Asp Pro Glu Pro Ile Ala Asp Ser Asn
            260                 265                 270
```

Asn Val Phe Phe Val Ser Ser Leu Asp Lys Ser His Glu Met Lys Thr
            275                 280                 285

Phe Ser Ser Ser Phe Asn Asn Pro Ile Phe Ala Pro Lys Pro Ala Ser
        290                 295                 300

Ser Thr Ile Ser Phe Ser Ser Glu Thr Asp Asn Pro Tyr Ser His
305                 310                 315                 320

Ser Glu Glu Val Ile Ser Phe Cys Pro Ser Leu Ser Asn Asn Thr Arg
                325                 330                 335

Gln Lys Val Ile Thr Arg Leu Lys Glu Lys Lys Arg Ala Arg Val Glu
            340                 345                 350

Glu Lys Lys Ala
        355

<210> SEQ ID NO 29
<211> LENGTH: 1215
<212> TYPE: DNA
<213> ORGANISM: Arabidopsis thaliana
<220> FEATURE:
<223> OTHER INFORMATION: G1261

<400> SEQUENCE: 29
gaaaagatca acttcttctt cttaccaaaa ctgtcggcgt cgtctcctct aagctcctcc      60
catggaagca aagaaggtc atcagcgtga ccgcctctgc gactattgcg actcctccgt     120
ggctcttgtc tactgcaaag ctgactccgc caagctctgc ctcgcctgcg acaagcaagt     180
ccacgtcgcc aaccaactct tcgccaaaca cttcaggtca cttctctgcg actcctgcaa     240
cgaatctccc tcttcccttt tctgcgagac tgaaaggtct gttctttgcc agaactgcga     300
ctggcaacac cacaccgcct cttcctccct tcatagccgc agacccttttg aaggatttac     360
cggctgtccc tccgtgcctg agttgctggc catcgttggc ctcgatgacc tcactctcga     420
ttccggattg ctttgggagt cacctgagat cgttagcctc aacgacctta ttgtttcggg     480
cgggtcgggt actcataact tccgggccac ggatgttcct cctctgccta gaatcgtca     540
cgccacctgc gggaaataca agatgagag atccgacag ctccgtggac tatccagatc     600
tgagcctggt tgtctgaaat tgaaaccccc agatgctgag atcgatgccg ggttccaatt     660
cctagcgccg gatttgtttt ctacatgcga gctggagagt ggactgaaat ggttcgatca     720
gcaagatcat gaggactttc catattgctc tctgctaaag aacttgtcgg agtcagatga     780
gaaacctgag aatgtagacc gagagtcatc ggtgatggtt cccgtttccg gctgcttaaa     840
ccgatgtgag gaagagactg tgatggttcc ggttatcact agtacaaggt cgatgacaca     900
tgagatcaac agtcttgaga ggaactctgc tctctctcgc tacaaagaaa agaagaagtc     960
tcgaaggtac gagaaacaca tcaggtatga atcacgcaag gttcgtgcag aaagcaggac    1020
aagaatcagg ggacgtttcg ccaaggcagc agatccatga atgatgatga ggttactttg    1080
ataatcaaaa atcttttgta ttaatcgaat catatagtgt gtatgatcag ataagttttt    1140
gtattctaag cttaggagtt atcactgtat atcgaccaca ctctcaaaat tgtcacttaa    1200
gaatagtttt tttaa                                                     1215

<210> SEQ ID NO 30
<211> LENGTH: 332
<212> TYPE: PRT
<213> ORGANISM: Arabidopsis thaliana
<220> FEATURE:
<223> OTHER INFORMATION: G1261 polypeptide

<400> SEQUENCE: 30

```
Met Glu Ala Glu Glu Gly His Gln Arg Asp Arg Leu Cys Asp Tyr Cys
1               5                   10                  15

Asp Ser Ser Val Ala Leu Val Tyr Cys Lys Ala Asp Ser Ala Lys Leu
            20                  25                  30

Cys Leu Ala Cys Asp Lys Gln Val His Val Ala Asn Gln Leu Phe Ala
            35                  40                  45

Lys His Phe Arg Ser Leu Leu Cys Asp Ser Cys Asn Glu Ser Pro Ser
        50                  55                  60

Ser Leu Phe Cys Glu Thr Glu Arg Ser Val Leu Cys Gln Asn Cys Asp
65                  70                  75                  80

Trp Gln His His Thr Ala Ser Ser Ser Leu His Ser Arg Arg Pro Phe
                85                  90                  95

Glu Gly Phe Thr Gly Cys Pro Ser Val Pro Glu Leu Leu Ala Ile Val
                100                 105                 110

Gly Leu Asp Asp Leu Thr Leu Asp Ser Gly Leu Leu Trp Glu Ser Pro
            115                 120                 125

Glu Ile Val Ser Leu Asn Asp Leu Ile Val Ser Gly Gly Ser Gly Thr
        130                 135                 140

His Asn Phe Arg Ala Thr Asp Val Pro Pro Leu Pro Lys Asn Arg His
145                 150                 155                 160

Ala Thr Cys Gly Lys Tyr Lys Asp Glu Met Ile Arg Gln Leu Arg Gly
                165                 170                 175

Leu Ser Arg Ser Glu Pro Gly Cys Leu Lys Phe Glu Thr Pro Asp Ala
            180                 185                 190

Glu Ile Asp Ala Gly Phe Gln Phe Leu Ala Pro Asp Leu Phe Ser Thr
        195                 200                 205

Cys Glu Leu Glu Ser Gly Leu Lys Trp Phe Asp Gln Gln Asp His Glu
210                 215                 220

Asp Phe Pro Tyr Cys Ser Leu Leu Lys Asn Leu Ser Glu Ser Asp Glu
225                 230                 235                 240

Lys Pro Glu Asn Val Asp Arg Glu Ser Ser Val Met Val Pro Val Ser
                245                 250                 255

Gly Cys Leu Asn Arg Cys Glu Glu Glu Thr Val Met Val Pro Val Ile
            260                 265                 270

Thr Ser Thr Arg Ser Met Thr His Glu Ile Asn Ser Leu Glu Arg Asn
        275                 280                 285

Ser Ala Leu Ser Arg Tyr Lys Glu Lys Lys Ser Arg Arg Tyr Glu
    290                 295                 300

Lys His Ile Arg Tyr Glu Ser Arg Lys Val Arg Ala Glu Ser Arg Thr
305                 310                 315                 320

Arg Ile Arg Gly Arg Phe Ala Lys Ala Ala Asp Pro
                325                 330
```

<210> SEQ ID NO 31
<211> LENGTH: 354
<212> TYPE: DNA
<213> ORGANISM: Arabidopsis thaliana
<220> FEATURE:
<223> OTHER INFORMATION: G1478

<400> SEQUENCE: 31
atgtgtagag ggtttgagaa agaagaagag agaagaagcg acaatggagg atgccaaaga      60
ctatgcacgg agagtcacaa agctccggta agctgtgagc tttgcggcga gaacgccacc     120
gtgtattgtg aggcagacgc agcttttcctt tgtaggaaat gcgatcgatg ggtccattct     180

```
gctaattttc tagctcggag acatctccgg cgcgtgatct gcacgacctg tcggaagcta        240
actcgtcgat gtcttgtcgg tgataatttt aatgttgttt taccggagat aaggatgata        300
gcaaggattg aagaacatag tagtgatcac aaaattccct ttgtgtttct ctga              354
```

```
<210> SEQ ID NO 32
<211> LENGTH: 117
<212> TYPE: PRT
<213> ORGANISM: Arabidopsis thaliana
<220> FEATURE:
<223> OTHER INFORMATION: G1478 polypeptide

<400> SEQUENCE: 32
```

Met Cys Arg Gly Phe Glu Lys Glu Glu Arg Arg Ser Asp Asn Gly
1               5                   10                  15

Gly Cys Gln Arg Leu Cys Thr Glu Ser His Lys Ala Pro Val Ser Cys
            20                  25                  30

Glu Leu Cys Gly Glu Asn Ala Thr Val Tyr Cys Glu Ala Asp Ala Ala
        35                  40                  45

Phe Leu Cys Arg Lys Cys Asp Arg Trp Val His Ser Ala Asn Phe Leu
    50                  55                  60

Ala Arg Arg His Leu Arg Arg Val Ile Cys Thr Thr Cys Arg Lys Leu
65                  70                  75                  80

Thr Arg Arg Cys Leu Val Gly Asp Asn Phe Asn Val Val Leu Pro Glu
                85                  90                  95

Ile Arg Met Ile Ala Arg Ile Glu Glu His Ser Ser Asp His Lys Ile
            100                 105                 110

Pro Phe Val Phe Leu
        115

```
<210> SEQ ID NO 33
<211> LENGTH: 396
<212> TYPE: DNA
<213> ORGANISM: Arabidopsis thaliana
<220> FEATURE:
<223> OTHER INFORMATION: G1481

<400> SEQUENCE: 33
```

```
atggggaaga agtgtgattt atgtaacggt gttgcaagaa tgtattgcga gtcagatcaa        60
gctagtttat gttgggattg cgacggtaaa gttcacggcg ctaatttctt ggtagctaaa       120
cacacgcgtt gtcttctctg tagcgcttgt cagtctctta cgccgtggaa agctactggg       180
cttcgtcttg gcccaacttt ctccgtctgc gagtcatgcg tcgctcttaa aaacgccggc       240
ggtggccgtg gaaacagagt tttatcggag aatcgtggtc aggaggaggt taatagtctc       300
tgctccgatg atgagatcgg aagctcttca gctcaagggt caaactattc tcggccgttg       360
aagcgatcgg cgtttaaatc aacggttgtt gtttaa                                  396
```

```
<210> SEQ ID NO 34
<211> LENGTH: 131
<212> TYPE: PRT
<213> ORGANISM: Arabidopsis thaliana
<220> FEATURE:
<223> OTHER INFORMATION: G1481 polypeptide

<400> SEQUENCE: 34
```

Met Gly Lys Lys Cys Asp Leu Cys Asn Gly Val Ala Arg Met Tyr Cys
1               5                   10                  15

Glu Ser Asp Gln Ala Ser Leu Cys Trp Asp Cys Asp Gly Lys Val His
            20                  25                  30

```
Gly Ala Asn Phe Leu Val Ala Lys His Thr Arg Cys Leu Leu Cys Ser
            35                  40                  45

Ala Cys Gln Ser Leu Thr Pro Trp Lys Ala Thr Gly Leu Arg Leu Gly
 50                  55                  60

Pro Thr Phe Ser Val Cys Glu Ser Cys Val Ala Leu Lys Asn Ala Gly
 65                  70                  75                  80

Gly Gly Arg Gly Asn Arg Val Leu Ser Glu Asn Arg Gly Gln Glu Glu
                85                  90                  95

Val Asn Ser Leu Cys Ser Asp Asp Glu Ile Gly Ser Ser Ser Ala Gln
                100                 105                 110

Gly Ser Asn Tyr Ser Arg Pro Leu Lys Arg Ser Ala Phe Lys Ser Thr
                115                 120                 125

Val Val Val
    130
```

<210> SEQ ID NO 35
<211> LENGTH: 366
<212> TYPE: DNA
<213> ORGANISM: Arabidopsis thaliana
<220> FEATURE:
<223> OTHER INFORMATION: G1929

<400> SEQUENCE: 35

```
atgtgtagag gcttgaataa tgaagagagc agaagaagtg acggaggagg ttgccggagt      60
ctctgcacga gaccgagtgt tccggtaagg tgtgagcttt gcgacggaga cgcctccgtg     120
ttctgtgaag cggactcggc gttcctctgt agaaaatgtg accggtgggt tcatggagcg     180
aattttctag cttggagaca cgtaaggcgc gtgctatgca cttcttgtca gaaactcacg     240
cgccggtgcc tcgtcggaga tcatgacttc cacgttgttt taccgtcggt gacgacggtc     300
ggagaaacca ccgtggagaa tagaagtgaa caagataatc atgaggttcc gtttgttttt     360
ctctga                                                                366
```

<210> SEQ ID NO 36
<211> LENGTH: 121
<212> TYPE: PRT
<213> ORGANISM: Arabidopsis thaliana
<220> FEATURE:
<223> OTHER INFORMATION: G1929 polypeptide

<400> SEQUENCE: 36

```
Met Cys Arg Gly Leu Asn Asn Glu Glu Ser Arg Arg Ser Asp Gly Gly
 1               5                  10                  15

Gly Cys Arg Ser Leu Cys Thr Arg Pro Ser Val Pro Val Arg Cys Glu
                20                  25                  30

Leu Cys Asp Gly Asp Ala Ser Val Phe Cys Glu Ala Asp Ser Ala Phe
            35                  40                  45

Leu Cys Arg Lys Cys Asp Arg Trp Val His Gly Ala Asn Phe Leu Ala
 50                  55                  60

Trp Arg His Val Arg Arg Val Leu Cys Thr Ser Cys Gln Lys Leu Thr
 65                  70                  75                  80

Arg Arg Cys Leu Val Gly Asp His Asp Phe His Val Val Leu Pro Ser
                85                  90                  95

Val Thr Thr Val Gly Glu Thr Thr Val Glu Asn Arg Ser Glu Gln Asp
                100                 105                 110

Asn His Glu Val Pro Phe Val Phe Leu
            115                 120
```

<210> SEQ ID NO 37
<211> LENGTH: 465
<212> TYPE: DNA
<213> ORGANISM: Glycine max
<220> FEATURE:
<223> OTHER INFORMATION: G4014

<400> SEQUENCE: 37

```
atgaggaagt gtgagctctg taacagtccc gcgaagttgt tctgcgaatc agatcaagcc      60
agcctctgtt ggaaatgcga tgctaaggtt cacagtgcaa acttcctcgt caccaaacat     120
cccaggattc ttctctgcca tgtttgtcaa tcactaacag cgtggcacgg cacaggaccc     180
aagtttgtac ccaccatgtc agtttgcaac acttgtgtca acaacaatag tactgagacc     240
tgcagccaac agaatcatga agacgatgat gatgatggta cgggagagga tcatgcagaa     300
aacgacgatg gtggtgtggc tgaagatgat gatgatgatg atgatgaaga aaatcaagtg     360
gttccatgga catctacacc accaccccca gcttccactt cttcaaatag tgttacaact     420
agttctacca ggttctctga tgttgaagaa ggtggctccg attaa                     465
```

<210> SEQ ID NO 38
<211> LENGTH: 154
<212> TYPE: PRT
<213> ORGANISM: Glycine max
<220> FEATURE:
<223> OTHER INFORMATION: G4014 polypeptide

<400> SEQUENCE: 38

```
Met Arg Lys Cys Glu Leu Cys Asn Ser Pro Ala Lys Leu Phe Cys Glu
1               5                   10                  15
Ser Asp Gln Ala Ser Leu Cys Trp Lys Cys Asp Ala Lys Val His Ser
            20                  25                  30
Ala Asn Phe Leu Val Thr Lys His Pro Arg Ile Leu Leu Cys His Val
        35                  40                  45
Cys Gln Ser Leu Thr Ala Trp His Gly Thr Gly Pro Lys Phe Val Pro
    50                  55                  60
Thr Met Ser Val Cys Asn Thr Cys Val Asn Asn Ser Thr Glu Thr
65                  70                  75                  80
Cys Ser Gln Gln Asn His Glu Asp Asp Asp Asp Gly Thr Gly Glu
            85                  90                  95
Asp His Ala Glu Asn Asp Asp Gly Gly Val Ala Glu Asp Asp Asp
            100                 105                 110
Asp Asp Asp Glu Glu Asn Gln Val Val Pro Trp Thr Ser Thr Pro Pro
        115                 120                 125
Pro Pro Ala Ser Thr Ser Ser Asn Ser Val Thr Thr Ser Ser Thr Arg
    130                 135                 140
Phe Ser Asp Val Glu Glu Gly Gly Ser Asp
145                 150
```

<210> SEQ ID NO 39
<211> LENGTH: 1236
<212> TYPE: DNA
<213> ORGANISM: Glycine max
<220> FEATURE:
<223> OTHER INFORMATION: G4015

<400> SEQUENCE: 39

```
atggaggaat catcaacaac atgcgtgttg tgcgagaaga gggcaatgat gctctgcgac      60
tcggaccagg ctaagctatg ctgggaatgc gacgagaaag tccacagcgc caatttcttg     120
gtcgcgaaac attctagggt tctttttatgt cgtttgtgtc actccccgac tccgtggaag     180
```

```
gcttcgggga tgaaactcac gcccactgtg tcgttttgta accgctgcgt tgcggaacgg    240
aacgcgaggt ggaaccgatt ggtgaataat gaaaatgaac atcaacaaca gcaacaacaa    300
caacaacaga gtgattttgt ggtggatgat gggagggaat atggttctga tcatgttttt    360
gatgatgacg atggtgatta tagtgatgat agtggtgaag aagaagaaga ggacgaggat    420
gatgaagagg agaatgagaa tcaagtggtt ccaatgtctt ctggttctgc cacgtcacca    480
cctaaggttg cctgtttagc gttgaagcga ttgagaaaca actcttttct gtcgattctt    540
cacatgatga gacagcgtgc tcttcatctg agatgcttag ttctacattg cctagtggtg    600
atgaatcacc ctcttttgaat ggaggaatca tcaacaacat gcgtgttgtg cgagaagagg    660
gcaatgatgc tctgcgactc ggaccaggct aagctatgct gggaatgcga cgagaaagtc    720
cacagcgcca atttcttggt cgcgaaacat tctagggttc ttttatgtcg tttgtgtcac    780
tccccgactc cgtggaaggc ttcggggatg aaactcacgc ccactgtgtc gttttgtaac    840
cgctgcgttg cggaacggaa cgcgaggtgg aaccgattgg tgaataatga aaatgaacat    900
caacaacagc aacaacaaca acaacagagt gattttgtgg tggatgatgg agggaatat    960 ggttctgatc atgttttttga tgatgacgat ggtgattata gtgatgatag tggtgaagaa    1020
gaagaagagg acgaggatga tgaagaggag aatgagaatc aagtggttcc aatgtcttct    1080
ggttctgcca cgtcaccacc taaggttgcc tgtttagcgt tgaagcgatt gagaaacaac    1140
tcttttctgt cgattcttca catgatgaga cagcgtgctc ttcatctgag atgcttagtt    1200
ctacattgcc tagtggtgat gaatcaccct ctttga                              1236
```

<210> SEQ ID NO 40
<211> LENGTH: 205
<212> TYPE: PRT
<213> ORGANISM: Glycine max
<220> FEATURE:
<223> OTHER INFORMATION: G4015 polypeptide

<400> SEQUENCE: 40

```
Met Glu Glu Ser Ser Thr Thr Cys Val Leu Cys Glu Lys Arg Ala Met
1               5                   10                  15

Met Leu Cys Asp Ser Asp Gln Ala Lys Leu Cys Trp Glu Cys Asp Glu
            20                  25                  30

Lys Val His Ser Ala Asn Phe Leu Val Ala Lys His Ser Arg Val Leu
        35                  40                  45

Leu Cys Arg Leu Cys His Ser Pro Thr Pro Trp Lys Ala Ser Gly Met
    50                  55                  60

Lys Leu Thr Pro Thr Val Ser Phe Cys Asn Arg Cys Val Ala Glu Arg
65                  70                  75                  80

Asn Ala Arg Trp Asn Arg Leu Val Asn Asn Glu Asn Glu His Gln Gln
                85                  90                  95

Gln Gln Gln Gln Gln Gln Ser Asp Phe Val Asp Asp Gly Arg
            100                 105                 110

Glu Tyr Gly Ser Asp His Val Phe Asp Asp Asp Gly Asp Tyr Ser
        115                 120                 125

Asp Asp Ser Gly Glu Glu Glu Glu Asp Glu Asp Asp Glu Glu Glu
    130                 135                 140

Asn Glu Asn Gln Val Val Pro Met Ser Ser Gly Ser Ala Thr Ser Pro
145                 150                 155                 160

Pro Lys Val Ala Cys Leu Ala Leu Lys Arg Leu Arg Asn Asn Ser Phe
                165                 170                 175
```

```
Leu Ser Ile Leu His Met Met Arg Gln Arg Ala Leu His Leu Arg Cys
            180                 185                 190

Leu Val Leu His Cys Leu Val Val Met Asn His Pro Leu
        195                 200                 205

<210> SEQ ID NO 41
<211> LENGTH: 666
<212> TYPE: DNA
<213> ORGANISM: Glycine max
<220> FEATURE:
<223> OTHER INFORMATION: G4016

<400> SEQUENCE: 41
atgaagaact gcgagttgtg caagcttccg gctcggactt tctgcgagtc ggaccaggct      60
agcttatgct gggactgcga cgccaaggtt catggagcca acttcctcgt ggaaagacac     120
acgcgcacgc tcctctgcca cgcgtgccag tcgcccacgc cgtggaaggc ctccggcgcc     180
gccctcggaa acaccgtctc gctgtgcgag agatgcgccg gcggaaccac cgaacaaggt     240
caagagagcc aaggaggcaa tgacgacgac atagacaccg acatagacac cgacgatgag     300
gatgactacg atgagagcga ggacgaggtt gccgccgacg aggaggacgg agacaaccag     360
gttgtccctt ggtcctccga gccgccgcca ccagccccga gctcttccag cagcgaagag     420
tcggttagcc ggtgcaacaa cgtggacgag gtttcgacca cattgaaacg ccgtcgccag     480
gaggacaatg attttcaggg ttggaattcg aataattggg atgtgaacg gagcgaagtg      540 gagagaggag gttggttggt tcggttgcgg cggagaaccg ccgatgatgt ggcggttgag     600
caacggagtg ctagagcggc gtctccagac ggttgctgtg tgatagagc atctgaagac      660 gtttga                                                                666

<210> SEQ ID NO 42
<211> LENGTH: 221
<212> TYPE: PRT
<213> ORGANISM: Glycine max
<220> FEATURE:
<223> OTHER INFORMATION: G4016

<400> SEQUENCE: 42

Met Lys Asn Cys Glu Leu Cys Lys Leu Pro Ala Arg Thr Phe Cys Glu
1               5                   10                  15

Ser Asp Gln Ala Ser Leu Cys Trp Asp Cys Asp Ala Lys Val His Gly
            20                  25                  30

Ala Asn Phe Leu Val Glu Arg His Thr Arg Thr Leu Leu Cys His Ala
        35                  40                  45

Cys Gln Ser Pro Thr Pro Trp Lys Ala Ser Gly Ala Ala Leu Gly Asn
    50                  55                  60

Thr Val Ser Leu Cys Glu Arg Cys Ala Gly Gly Thr Thr Glu Gln Gly
65                  70                  75                  80

Gln Glu Ser Gln Gly Gly Asn Asp Asp Asp Ile Asp Thr Asp Ile Asp
                85                  90                  95

Thr Asp Asp Glu Asp Asp Tyr Asp Glu Ser Glu Asp Glu Val Ala Ala
            100                 105                 110

Asp Glu Glu Asp Gly Asp Asn Gln Val Val Pro Trp Ser Ser Glu Pro
        115                 120                 125

Pro Pro Pro Ala Pro Ser Ser Ser Ser Glu Glu Ser Val Ser Arg
    130                 135                 140

Cys Asn Asn Val Asp Glu Val Ser Thr Thr Leu Lys Arg Arg Arg Gln
145                 150                 155                 160
```

Glu Asp Asn Asp Phe Gln Gly Trp Asn Ser Asn Asn Trp Gly Cys Glu
            165                 170                 175

Arg Ser Glu Val Glu Arg Gly Gly Trp Leu Val Arg Leu Arg Arg
        180                 185                 190

Thr Ala Asp Asp Val Ala Val Glu Gln Arg Ser Ala Arg Ala Ala Ser
        195                 200                 205

Pro Asp Gly Cys Cys Gly Asp Arg Ala Ser Glu Asp Val
    210                 215                 220

<210> SEQ ID NO 43
<211> LENGTH: 375
<212> TYPE: DNA
<213> ORGANISM: Glycine max
<220> FEATURE:
<223> OTHER INFORMATION: G4019

<400> SEQUENCE: 43
atgtgcaaag gtgcagaagg agaaaagcaa catggtttct gcagcagctt tctacataaa      60
gaatgtgcaa ccagaagtgc tacatgttgt gagctatgtg ggttacaggc ttcattgtat     120
tgtcaagctg atgatgcata cttgtgtaga aatgtgata aaagggttca tgaagctaat     180
tttttggccc ttaggcacat taggtgcttt ctgtgcaaca catgtcaaaa ccttacgcga     240
agatatctca ttggagcatc aatagaggtg gttcttccag ccaacattaa ctggaccatt     300
ggaaatctcc ctagcaacag aggaatccac agaaagtgct caagaatgca taacaacctt     360
tccctcttgt tataa                                                      375

<210> SEQ ID NO 44
<211> LENGTH: 124
<212> TYPE: PRT
<213> ORGANISM: Glycine max
<220> FEATURE:
<223> OTHER INFORMATION: G4019

<400> SEQUENCE: 44

Met Cys Lys Gly Ala Glu Gly Glu Lys Gln His Gly Phe Cys Ser Ser
1               5                   10                  15

Phe Leu His Lys Glu Cys Ala Thr Arg Ser Ala Thr Cys Cys Glu Leu
            20                  25                  30

Cys Gly Leu Gln Ala Ser Leu Tyr Cys Gln Ala Asp Asp Ala Tyr Leu
        35                  40                  45

Cys Arg Lys Cys Asp Lys Arg Val His Glu Ala Asn Phe Leu Ala Leu
    50                  55                  60

Arg His Ile Arg Cys Phe Leu Cys Asn Thr Cys Gln Asn Leu Thr Arg
65                  70                  75                  80

Arg Tyr Leu Ile Gly Ala Ser Ile Glu Val Val Leu Pro Ala Asn Ile
                85                  90                  95

Asn Trp Thr Ile Gly Asn Leu Pro Ser Asn Arg Gly Ile His Arg Lys
            100                 105                 110

Cys Ser Arg Met His Asn Asn Leu Ser Leu Leu Leu
        115                 120

<210> SEQ ID NO 45
<211> LENGTH: 46
<212> TYPE: PRT
<213> ORGANISM: Arabidopsis thaliana
<220> FEATURE:
<223> OTHER INFORMATION: G1988 conserved B-box ZF domain

<400> SEQUENCE: 45

```
Cys Glu Leu Cys Gly Ala Glu Ala Asp Leu His Cys Ala Ala Asp Ser
1               5                   10                  15

Ala Phe Leu Cys Arg Ser Cys Asp Ala Lys Phe His Ala Ser Asn Phe
            20                  25                  30

Leu Phe Ala Arg His Phe Arg Arg Val Ile Cys Pro Asn Cys
        35                  40                  45

<210> SEQ ID NO 46
<211> LENGTH: 42
<212> TYPE: PRT
<213> ORGANISM: Glycine max
<220> FEATURE:
<223> OTHER INFORMATION: G4004 conserved B-box ZF domain

<400> SEQUENCE: 46

Cys Glu Leu Cys Gly Gly Ala Ala Val His Cys Ala Ala Asp Ser
1               5                   10                  15

Ala Phe Leu Cys Pro Arg Cys Asp Ala Lys Val His Gly Ala Asn Phe
            20                  25                  30

Leu Ala Ser Arg His Val Arg Arg Leu
        35                  40

<210> SEQ ID NO 47
<211> LENGTH: 42
<212> TYPE: PRT
<213> ORGANISM: Glycine max
<220> FEATURE:
<223> OTHER INFORMATION: G4005 conserved B-box ZF domain

<400> SEQUENCE: 47

Cys Glu Leu Cys Gly Gly Val Ala Ala Val His Cys Ala Ala Asp Ser
1               5                   10                  15

Ala Phe Leu Cys Leu Val Cys Asp Asp Lys Val His Gly Ala Asn Phe
            20                  25                  30

Leu Ala Ser Arg His Arg Arg Arg Leu
        35                  40

<210> SEQ ID NO 48
<211> LENGTH: 42
<212> TYPE: PRT
<213> ORGANISM: Zea mays
<220> FEATURE:
<223> OTHER INFORMATION: G4000 conserved B-box ZF domain

<400> SEQUENCE: 48

Cys Glu Leu Cys Gly Gly Ala Ala Val His Cys Ala Ala Asp Ser
1               5                   10                  15

Ala Phe Leu Cys Leu Arg Cys Asp Ala Lys Val His Gly Ala Asn Phe
            20                  25                  30

Leu Ala Ser Arg His Val Arg Arg Leu
        35                  40

<210> SEQ ID NO 49
<211> LENGTH: 46
<212> TYPE: PRT
<213> ORGANISM: Citrus sinensis
<220> FEATURE:
<223> OTHER INFORMATION: G4007 conserved B-box ZF domain

<400> SEQUENCE: 49

Cys Glu Leu Cys Ser Gln Glu Ala Ala Leu His Cys Ala Ser Asp Glu
1               5                   10                  15

Ala Phe Leu Cys Phe Asp Cys Asp Asp Arg Val His Lys Ala Asn Phe
```

```
                        20                  25                  30

Leu Val Ala Arg His Val Arg Gln Thr Leu Cys Ser Gln Cys
        35                  40                  45

<210> SEQ ID NO 50
<211> LENGTH: 46
<212> TYPE: PRT
<213> ORGANISM: Populus trichocarpa
<220> FEATURE:
<223> OTHER INFORMATION: G4009 conserved B-box ZF domain

<400> SEQUENCE: 50

Cys Glu Leu Cys Lys Gly Glu Ala Gly Val Tyr Cys Asp Ser Asp Ala
1               5                   10                  15

Ala Tyr Leu Cys Phe Asp Cys Asp Ser Asn Val His Asn Ala Asn Phe
            20                  25                  30

Leu Val Ala Arg His Ile Arg Arg Val Ile Cys Ser Gly Cys
        35                  40                  45

<210> SEQ ID NO 51
<211> LENGTH: 42
<212> TYPE: PRT
<213> ORGANISM: Oryza sativa
<220> FEATURE:
<223> OTHER INFORMATION: G4011 conserved B-box ZF domain

<400> SEQUENCE: 51

Cys Ala Leu Cys Gly Ala Ala Ala Val His Cys Glu Ala Asp Ala
1               5                   10                  15

Ala Phe Leu Cys Ala Ala Cys Asp Ala Lys Val His Gly Ala Asn Phe
            20                  25                  30

Leu Ala Ser Arg His His Arg Arg Arg Val
        35                  40

<210> SEQ ID NO 52
<211> LENGTH: 42
<212> TYPE: PRT
<213> ORGANISM: Oryza sativa
<220> FEATURE:
<223> OTHER INFORMATION: G4012 conserved B-box ZF domain

<400> SEQUENCE: 52

Cys Glu Leu Cys Gly Gly Val Ala Ala Val His Cys Ala Ala Asp Ser
1               5                   10                  15

Ala Phe Leu Cys Leu Val Cys Asp Asp Lys Val His Gly Ala Asn Phe
            20                  25                  30

Leu Ala Ser Arg His Arg Arg Arg Arg Leu
        35                  40

<210> SEQ ID NO 53
<211> LENGTH: 42
<212> TYPE: PRT
<213> ORGANISM: Zea mays
<220> FEATURE:
<223> OTHER INFORMATION: G4297 conserved B-box ZF domain

<400> SEQUENCE: 53

Cys Glu Leu Cys Gly Gly Ala Ala Ala Val His Cys Ala Ala Asp Ser
1               5                   10                  15

Ala Phe Leu Cys Pro Arg Cys Asp Ala Lys Val His Gly Ala Asn Phe
            20                  25                  30

Leu Ala Ser Arg His Val Arg Arg Arg Leu
        35                  40
```

```
<210> SEQ ID NO 54
<211> LENGTH: 41
<212> TYPE: PRT
<213> ORGANISM: Oryza sativa
<220> FEATURE:
<223> OTHER INFORMATION: G4298 conserved B-box ZF domain

<400> SEQUENCE: 54

Cys Glu Leu Cys Gly Gly Val Ala Ala Val His Cys Ala Ala Asp Ser
1               5                  10                  15

Ala Phe Leu Cys Leu Val Cys Asp Asp Lys Val His Gly Ala Asn Phe
            20                  25                  30

Leu Ala Ser Arg His Pro Arg Arg Arg
        35                  40

<210> SEQ ID NO 55
<211> LENGTH: 46
<212> TYPE: PRT
<213> ORGANISM: Lycopersicon esculentum
<220> FEATURE:
<223> OTHER INFORMATION: G4299 conserved B-box ZF domain

<400> SEQUENCE: 55

Cys Glu Leu Cys Asn Asp Gln Ala Ala Leu Phe Cys Pro Ser Asp Ser
1               5                  10                  15

Ala Phe Leu Cys Phe His Cys Asp Ala Lys Val His Gln Ala Asn Phe
            20                  25                  30

Leu Val Ala Arg His Leu Arg Leu Thr Leu Cys Ser His Cys
        35                  40                  45

<210> SEQ ID NO 56
<211> LENGTH: 42
<212> TYPE: PRT
<213> ORGANISM: Zea mays
<220> FEATURE:
<223> OTHER INFORMATION: G4001 conserved B-box ZF domain

<400> SEQUENCE: 56

Cys Glu Leu Cys Gly Gly Ala Ala Ala Val His Cys Ala Ala Asp Ser
1               5                  10                  15

Ala Phe Leu Cys Leu Arg Cys Asp Ala Lys Val His Gly Ala Asn Phe
            20                  25                  30

Leu Ala Ser Arg His Val Arg Arg Arg Leu
        35                  40

<210> SEQ ID NO 57
<211> LENGTH: 9
<212> TYPE: PRT
<213> ORGANISM: Arabidopsis thaliana
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<223> OTHER INFORMATION: G1988 clade signature C-terminal motif

<400> SEQUENCE: 57

Arg Xaa Xaa Xaa Ala Xaa Xaa Xaa Trp
1               5
```

```
<210> SEQ ID NO 58
<211> LENGTH: 5
<212> TYPE: PRT
<213> ORGANISM: Arabidopsis thaliana
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<223> OTHER INFORMATION: G1988 clade signature C-terminal motif

<400> SEQUENCE: 58

Glu Xaa Trp Xaa Glu
1               5

<210> SEQ ID NO 59
<211> LENGTH: 780
<212> TYPE: DNA
<213> ORGANISM: artificial sequence
<220> FEATURE:
<223> OTHER INFORMATION: P2499 (35S::G1988 construct)

<400> SEQUENCE: 59
caccatcatc attccaaacc aattctctct cacttctttc tggtgatcag agagatcgac      60
tcaatggtga gcttttgcga gctttgtggt gccgaagctg atctccattg tgccgcggac     120
tctgccttcc tctgccgttc ttgtgacgct aagttccatg cctcaaattt tctcttcgct     180
cgtcatttcc ggcgtgtcat ctgcccaaat tgcaaatctc ttactcaaaa tttcgtttct     240
ggtcctcttc ttccttggcc tccacgaaca acatgttgtt cagaatcgtc gtcttcttct     300
tgctgctcgt ctcttgactg tgtctcaagc tccgagctat cgtcaacgac gcgtgacgta     360
aacagagcgc gagggaggga aaacagagtg aatgccaagg ccgttgcggt tacggtggcg     420
gatggcattt ttgtaaattg gtgtggtaag ttaggactaa acaggggattt aacaaacgct     480 gtcgtttcat atgcgtcttt ggctttggct gtggagacga ggccaagagc gacgaagaga     540
gtgttcttag cggcggcgtt ttggttcggc gttaagaaca cgacgacgtg gcagaattta     600
aagaaagtag aagatgtgac tggagtttca gctgggatga ttcgagcggt tgaaagcaaa     660
ttggcgcgtg caatgacgca gcagcttaga cggtggcgcg tggattcgga ggaaggatgg     720
gctgaaaacg acaacgtttg agaaatatta ttgacatggg tcccgcatta tgcaaattag     780

<210> SEQ ID NO 60
<211> LENGTH: 752
<212> TYPE: DNA
<213> ORGANISM: artificial sequence
<220> FEATURE:
<223> OTHER INFORMATION: P26748 (35S::G4004 construct)

<400> SEQUENCE: 60
atgaagccca agacttgcga gctttgtcat caactagctt ctctctattg tccctccgat      60
tccgcatttc tctgcttcca ctgcgacgcc gccgtccacg ccgccaactt cctcgtagct     120
cgccacctcc gccgcctcct ctgctccaaa tgcaaccgtt tcgccgcaat tcacatctcc     180
ggtgctatat cccgccacct ctcctccacc tgcacctctt gctccctgga gattccttcc     240
gccgactccg attctctccc ttcctcttct acctgcgtct ccagttccga gtcttgctct     300
acgaatcaga ttaaggcgga gaagaagagg aggaggagga ggaggagttt ctcgagttcc     360
tccgtgaccg acgacgcatc tccggcggcg aagaagcggc ggagaaatgg cggatcggtg     420
```

```
gcggaggtgt ttgagaaatg gagcagagag atagggttag ggttagggt  gaacggaaat      480 cgcgtggcgt cgaacgctct gagtgtgtgc ctcggaaagt ggaggtcgct tccgttcagg      540
gtggctgctg cgacgtcgtt ttggttgggg ctgagatttt gtggggacag aggcctcgcc      600
acgtgtcaga atctggcgag gttggaggca atatctggag tgccagcaaa gctgattctg      660
ggcgcacatg ccaacctcgc acgtgtcttc acgcaccgcc gcgaattgca ggaaggatgg      720
ggcgagtcct agctgatgat agctatacca at                                    752

<210> SEQ ID NO 61
<211> LENGTH: 756
<212> TYPE: DNA
<213> ORGANISM: artificial sequence
<220> FEATURE:
<223> OTHER INFORMATION: P26749 (35S::G4005) construct

<400> SEQUENCE: 61
aggcgaagat gaagggtaag acttgcgagc tttgtgatca acaagcttct ctctattgtc       60
cctccgattc cgcatttctc tgctccgact gcgacgccgc cgtgcacgcc gccaactttc      120
tcgtagctcg tcacctccgc cgcctcctct gctccaaatg caaccgtttc gccggatttc      180
acatctcctc cggcgctata tcccgccacc tctcgtccac ctgcagctct tgctccccgg      240
agaatccttc cgctgactac tccgattctc tcccttcctc ttctacctgc gtctccagtt      300
ccgagtcttg ctccacgaag cagattaagg tggagaagaa gaggagttgg tcgggttcct      360
ccgtgaccga cgacgcatct ccggcggcga agaagcggca gaggagtgga ggatcggagg      420
aggtgtttga gaaatggagc agagagatag ggttagggtt agggttaggg gtaaacggaa      480
atcgcgtggc gtcgaacgct ctgagtgtgt gcctgggaaa gtggaggtgg cttccgttca      540
gggtggctgc tgcgacgtcg ttttggttgg gctgagatt  ttgtgggac  agagggctgg      600 cctcgtgtca gaatctggcg aggttggagg caatatccgg agtgccagtt aagctgattc      660
tggccgcaca tggcgacctg gcacgtgtct tcacgcaccg ccgcgaattg caggaaggat      720
ggggcgagtc ctagctagct ccaatgtgta atcgtc                                756

<210> SEQ ID NO 62
<211> LENGTH: 6
<212> TYPE: PRT
<213> ORGANISM: Arabidopsis thaliana
<220> FEATURE:
<221> NAME/KEY: misc_feature
<222> LOCATION: (2)..(5)
<223> OTHER INFORMATION: Xaa can be any naturally occurring amino acid
<220> FEATURE:
<223> OTHER INFORMATION: G1988 clade signature C-terminal motif

<400> SEQUENCE: 62

Trp Xaa Xaa Xaa Xaa Gly
1               5

<210> SEQ ID NO 63
<211> LENGTH: 709
<212> TYPE: DNA
<213> ORGANISM: artificial sequence
<220> FEATURE:
<223> OTHER INFORMATION: expression construct P27404 comprises a 35S::
      G4000 direct promoter fusion construct containing a cDNA clone of
      G4000 and carries kanamycin resistance

<400> SEQUENCE: 63
gacgtcggga atgggcgctg ctcgtgactc cgcggcggcg ggccagaagc acggcaccgg       60
cacgcggtgc gagctctgcg ggggcgcggc ggccgtgcac tgcgccgcgg actcggcgtt      120
```

```
cctctgcctg cgctgcgacg ccaaggtgca cggcgccaac ttcctggcgt ccaggcacgt      180
gaggcggcgc ctggtgccgc gccgggccgc cgacccgag gcgtcgtcgg ccgcgtccag       240
cggctcctcc tgcgtgtcca cggccgactc cgcggagtcg gccgccacgg caccggctcc     300
gtgcccttcg aggacggcgg ggaggagggc tccggctcgt gcgcggcggc cgcgcgcgga    360
ggcggtcctg gaggggtggg ccaagcggat ggggttcgcg gcggggccgg cgcgccggcg    420
cgccgcggcg gcggccgccg cgctccgggc gctcggccgg ggcgtggccg ctgcccgcgt     480
gccgctccgc gtcgggatgg ccggcgcgct ctggtcggag gtcgccgccg ggtgccgagg    540
caatggaggg gaggaggcct cgctgctcca gcggctggag gccgccgcgc acgtgccggc     600
gcggctggtg ctgaccgccg cgtcgtggat ggcgcgccgg ccggacgccc ggcaggagga    660
ccacgaggag ggatgggccg agtgctcctg agttcctgat ccagacggg                   709

<210> SEQ ID NO 64
<211> LENGTH: 676
<212> TYPE: DNA
<213> ORGANISM: artificial sequence
<220> FEATURE:
<223> OTHER INFORMATION: expression construct P27406 comprises a 35S::
      G4012 direct promoter fusion construct containing a cDNA clone of
      G4012 and carries kanamycin resistance

<400> SEQUENCE: 64
tgtaatggag gtcggcaacg gcaagtgcgg cggtggtggc gccgggtgcg agctgtgcgg     60
gggcgtggcc gcggtgcact cgccgctga ctccgcgttt ctttgcttgg tatgtgacga     120
caaggtgcac ggcgccaact tcctcgcgtc caggcaccgc cgccgccggt tgggggttga    180
ggtggtggat gaggaggatg acgcccggtc cacggcgtcg agctcgtgcg tgtcgacggc     240
ggactccgcg tcgtccacgg cggcggcggc ggcggcggtg gagagcgagg acgtcaggag    300 gaggggggcgg cgcgggcggc gtgccccgcg cgcggaggcg gttctggagg ggtgggcgaa    360
gcggatgggg ttgtcgtcgg gcgcggcgcg caggcgcgcc gccgcggccg ggcggcgct    420 ccgcgcggtg ggccgtggcg tcgccgcctc ccgcgtcccg atccgcgtcg cgatggccgc    480
cgcgctctgg tcggaggtcg cctcctcctc ctcccgtcgc cgccgccgcc ccggcgccgg    540
acaggccgcg ctgctccggc ggctggaggc cagcgcgcac gtgccggcga ggctgctcct    600
gacggtggcg tcgtggatgg cgcgcgcgtc gacgccgccc gccgccgagg agggctgggc    660
cgagtgctcc tgatcc                                                     676

<210> SEQ ID NO 65
<211> LENGTH: 787
<212> TYPE: DNA
<213> ORGANISM: artificial sequence
<220> FEATURE:
<223> OTHER INFORMATION: expression construct P27428 comprises a direct
      promoter fusion of the 35S promoter to a cDNA clone of G4299 and
      carries kanamycin resistance

<400> SEQUENCE: 65
aatggaactt ctgtcctcta aactctgtga gctttgcaat gatcaagctg ctctgttttg     60
tccatctgat tcagctttc tctgttttca ctgtgatgct aaagttcatc aggctaattt     120
ccttgttgct cgccaccttc gtcttactct ttgctctcac tgtaactccc ttacgaaaaa    180
acgttttttc ccttgttcac cgccgcctcc tgctctttgt ccttcctgtt cccggaattc    240
gtctggtgat tccgatctcc gttctgtttc aacgacgtcg tcgtcgtctt cgtcgacttg    300
tgtttccagc acgcagtcca gtgctattac tcaaaaaatt aacataatct cttcaaatcg    360
```

-continued

| | | |
|---|---|---|
| aaagcaattt ccggacagcg actctaacgg tgaagtcaat tctggcagat gtaatttagt | 420 |
| acgatccaga agtgtgaaat tgcgagatcc aagagcggcg acttgtgtgt tcatgcattg | 480 |
| gtgcacaaag cttcaaatga accgcgagga acgtgtggtg caaacggctt gtagtgtgtt | 540 |
| gggtatttgt tttagtcggt ttaggggtct gcctctacgg gttgccctgg cggcctgttt | 600 |
| ttggtttggt ttgaaaacta ccgaagacaa atcaaagacg tcgcaatctt tgaagaaatt | 660 |
| agaggagatc tcgggtgtgc cggcgaagat aatattagca acagaattaa agcttcgaaa | 720 |
| aataatgaaa accaaccacg gccaacctca agcaatggaa gaaagctggg ctgaatcctc | 780 |
| gccctaa | 787 |

<210> SEQ ID NO 66
<211> LENGTH: 1073
<212> TYPE: DNA
<213> ORGANISM: Triticum aestivum
<220> FEATURE:
<221> NAME/KEY: misc_feature
<222> LOCATION: (1005)..(1005)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t
<220> FEATURE:
<223> OTHER INFORMATION: Ta1988

<400> SEQUENCE: 66

| | | |
|---|---|---|
| atggcgggcg acaggtgcaa gggcgcgatc gcggggtgcg agctgtgcgg gggcgtcgcg | 60 |
| gcggtgcact gcgcggcgga ctcggcgttc ctctgcgtgc cctgcgacgc caaggtgcac | 120 |
| ggcgccaact tcctcgcctc caggcacctg cgccgccgcc tcgtccacgc ggccgcggac | 180 |
| gaggacgccg gatccgcggg ctcgggctcg ggctcggagt cgtcctccag ctcctcctgc | 240 |
| gtgtccaccg ccgactcgtg cgcggccgcc tccgcggcga cgcggggcgg ggggaggagg | 300 |
| agggccgggt gcaagcaccg gcgagcgcgg gcggaggtcg tcctcgaggg gtgggccaag | 360 |
| cggatgggcc tcgcggcggg aacgcacgcg cggcgggcgg ccaggccgc gggcgcgctc | 420 |
| cgggcgctag gccgtggcgt ctccgcctcc cgcgtcccgc tccgcgtcgc gatggccgcc | 480 |
| gcgctctggt cggaggtcgc cggatccggc tgcgcggagg ccgcgctgct ccgccggctg | 540 |
| gaggcaagct cgcacgtgcc ggcgaggctg gtggtcacgg tggcgtcgtg gatggcgcgc | 600 |
| accgcggtca gggcccccgc ccccgccccc gccgaggagg gctgggccga gtgctcctga | 660 |
| gccacggcca cggcccgggc ccatctccct cccgatgacg agccgaacaa ggaaggaagc | 720 |
| gagcccgaga tagaattaca cgtagaatgt aacatgtgaa gcaaagttcg tttgtttaat | 780 |
| ttccccccgcc ttattctaag cacgattata catattgtta ttaatattcc ttcatcataa | 840 |
| aaaaaaaaaa aaaatgctcc aaaacagagt ttccgccgtg gttcaaactt cccccccgccc | 900 |
| tttggaggcg aggggcgctg cattctcgct ggggtattgg agagatcacc ctcgcccaga | 960 |
| ccctctaaaa agttaaggcc tgtactctct ctcccatgct gcagnggggg gcccgtntcc | 1020 |
| acttttcccc ctctacgggg cgttttggc cgccctctgg cccctcattg tat | 1073 |

<210> SEQ ID NO 67
<211> LENGTH: 219
<212> TYPE: PRT
<213> ORGANISM: Triticum aestivum
<220> FEATURE:
<223> OTHER INFORMATION: Ta1988 polypeptide

<400> SEQUENCE: 67

Met Ala Gly Asp Arg Cys Lys Gly Ala Ile Ala Gly Cys Glu Leu Cys
1               5                   10                  15

Gly Gly Val Ala Ala Val His Cys Ala Ala Asp Ser Ala Phe Leu Cys
            20                  25                  30

Val Pro Cys Asp Ala Lys Val His Gly Ala Asn Phe Leu Ala Ser Arg
            35                  40                  45

His Leu Arg Arg Arg Leu Val His Ala Ala Asp Glu Asp Ala Gly
50                  55                  60

Ser Ala Gly Ser Gly Ser Glu Ser Ser Ser Ser Ser Cys
65                  70                  75                  80

Val Ser Thr Ala Asp Ser Cys Ala Ala Ser Ala Ala Thr Arg Ala
                85                  90                  95

Ala Gly Arg Arg Arg Ala Gly Cys Lys His Arg Ala Arg Ala Glu
                100                 105                 110

Val Val Leu Glu Gly Trp Ala Lys Arg Met Gly Leu Ala Ala Gly Thr
            115                 120                 125

Ala Arg Arg Arg Ala Ala Arg Ala Ala Gly Ala Leu Arg Ala Leu Gly
            130                 135                 140

Arg Gly Val Ser Ala Ser Arg Val Pro Leu Arg Val Ala Met Ala Ala
145                 150                 155                 160

Ala Leu Trp Ser Glu Val Ala Gly Ser Gly Cys Ala Glu Ala Ala Leu
                165                 170                 175

Leu Arg Arg Leu Glu Ala Ser Ser His Val Pro Ala Arg Leu Val Val
            180                 185                 190

Thr Val Ala Ser Trp Met Ala Arg Thr Ala Val Arg Ala Pro Ala Pro
            195                 200                 205

Ala Pro Ala Glu Glu Gly Trp Ala Glu Cys Ser
        210                 215

<210> SEQ ID NO 68
<211> LENGTH: 42
<212> TYPE: PRT
<213> ORGANISM: Triticum aestivum
<220> FEATURE:
<223> OTHER INFORMATION: Ta1988 conserved B-box ZF domain

<400> SEQUENCE: 68

Cys Glu Leu Cys Gly Gly Val Ala Ala Val His Cys Ala Ala Asp Ser
1               5                   10                  15

Ala Phe Leu Cys Val Pro Cys Asp Ala Lys Val His Gly Ala Asn Phe
            20                  25                  30

Leu Ala Ser Arg His Leu Arg Arg Arg Leu
        35                  40

<210> SEQ ID NO 69
<211> LENGTH: 16
<212> TYPE: PRT
<213> ORGANISM: Arabidopsis thaliana
<220> FEATURE:
<221> NAME/KEY: misc_feature
<222> LOCATION: (3)..(3)
<223> OTHER INFORMATION: Xaa can be Lys or Arg
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:

-continued

```
<223> OTHER INFORMATION: CBF conserved consecutive amino acid residues

<400> SEQUENCE: 69

Pro Lys Xaa Pro Ala Gly Arg Xaa Lys Phe Xaa Glu Thr Arg His Pro
1               5                   10                  15

<210> SEQ ID NO 70
<211> LENGTH: 5
<212> TYPE: PRT
<213> ORGANISM: Arabidopsis thaliana
<220> FEATURE:
<223> OTHER INFORMATION: CBF conserved consecutive amino acid residues

<400> SEQUENCE: 70

Asp Ser Ala Trp Arg
1               5
```

What is claimed is:

1. A transgenic dicot plant having reduced sensitivity to light as compared to a control plant, wherein the transgenic dicot plant comprises a recombinant polynucleotide encoding a polypeptide that comprises, in order from n-terminus to c-terminus:
   (a) a conserved domain with at least 58% amino acid identity with amino acids 5-50 of SEQ ID NO: 2; and
   (b) SEQ ID NO: 58;
   wherein the control plant does not comprise the recombinant polynucleotide; and
   wherein expression of the polypeptide in the transgenic dicot plant confers to the transgenic dicot plant the reduced sensitivity to light and wherein the reduced sensitivity to light is characterized by longer hypocotyls, longer petioles, more upright leaves, and/or greater internode length, than the control plant.

2. The transgenic dicot plant of claim 1, wherein the conserved domain has at least 60% identity with amino acids 5-50 of SEQ ID NO: 2.

3. The transgenic dicot plant of claim 1, wherein the conserved domain has at least 85% identity with amino acids 5-50 of SEQ ID NO: 2.

4. The transgenic dicot plant of claim 1, wherein the conserved domain has at least 95% identity with amino acids 5-50 of SEQ ID NO: 2.

5. The transgenic dicot plant of claim 1, wherein the transgenic dicot plant is a legume.

6. The transgenic dicot plant of claim 1, wherein expression of the polypeptide is regulated by a constitutive, inducible, or tissue-specific promoter.

7. A transgenic seed produced from the transgenic dicot plant of claim 1, wherein the transgenic seed comprises the recombinant polynucleotide.

8. A transgenic dicot plant having greater tolerance to low nitrogen during germination relative to a control plant, wherein the transgenic plant comprises a recombinant polynucleotide encoding a—polypeptide that comprises, in order from n-terminus to c-terminus:
   (a) a conserved domain with at least 58% amino acid identity with amino acids 5-50 of SEQ ID NO: 2; and
   (b) SEQ ID NO: 58;
   wherein the control plant does not comprise the recombinant polynucleotide; and
   wherein expression of the polypeptide in the transgenic plant results in the transgenic plant having the greater tolerance to low nitrogen during germination relative to the control plant.

9. The transgenic plant of claim 8, wherein the conserved domain has at least 60% amino acid identity with amino acids 5-50 of SEQ ID NO: 2.

10. The transgenic dicot plant of claim 8, wherein the conserved domain has at least 85% amino acid identity with amino acids 5-50 of SEQ ID NO: 2.

11. The transgenic dicot plant of claim 8, wherein the conserved domain has at least 95% amino acid identity with amino acids 5-50 of SEQ ID NO: 2.

12. The transgenic dicot plant of claim 8, wherein the transgenic plant produces greater yield as compared to the control plant.

13. The transgenic dicot plant of claim 8, wherein the transgenic plant is more tolerant to a nitrogen limitation of 20 mg/L of $NH_4NO_3$ as the nitrogen source than the control plant.

14. A transgenic dicot plant producing greater yield than a control plant, wherein the transgenic dicot plant comprises a recombinant polynucleotide encoding a polypeptide that comprises, in order from n-terminus to c-terminus:
   (a) a conserved domain with at least 58% amino acid identity with amino acids 5-50 of SEQ ID NO: 2; and
   (b) SEQ ID NO: 58;
   wherein the control plant does not comprise the recombinant polynucleotide; and
   wherein expression of the polypeptide in the transgenic dicot plant results in the transgenic dicot plant producing the greater yield than the control plant.

15. The transgenic dicot plant of claim 14, wherein the conserved domain has at least 60% identity with amino acids 5-50 of SEQ ID NO: 2.

16. The transgenic dicot plant of claim 14, wherein the conserved domain has at least 85% identity with amino acids 5-50 of SEQ ID NO: 2.

17. The transgenic dicot plant of claim 14, wherein the conserved domain has at least 95% identity with amino acids 5-50 of SEQ ID NO: 2.

18. The transgenic dicot plant of claim 14, wherein the transgenic plant is a legume.

19. A transgenic seed produced from the transgenic dicot plant of claim 14, wherein the transgenic seed comprises the recombinant polynucleotide.

20. A method for altering the light response of a dicot plant as compared to the light response of a control plant, the method comprising:
   (a) providing a recombinant polynucleotide encoding a polypeptide, wherein the polypeptide comprises, in order from n-terminus to c-terminus:

(i) a conserved domain with at least 58% amino acid identity with amino acids 5-50 of SEQ ID NO: 2; and
(ii) SEQ ID NO: 58; and
(b) introducing the recombinant polynucleotide into a target dicot plant to produce a transformed dicot plant;
wherein overexpression of the polypeptide in the transformed dicot plant confers the altered light response in the transformed dicot plant; and
wherein the altered light response is characterized by longer hypocotyls, longer petioles, more upright leaves, and/or greater internode length, than the control plant.

21. The method of claim 20, wherein the conserved domain has at least 60% identity with amino acids 5-50 of SEQ ID NO: 2.

22. The method of claim 20, wherein the conserved domain has at least 85% identity with amino acids 5-50 of SEQ ID NO: 2.

23. The method of claim 20, wherein the conserved domain has at least 95% identity with amino acids 5-50 of SEQ ID NO: 2.

24. The method of claim 20, wherein the method further comprises the step of:
(c) selecting a transgenic dicot plant by its ectopic expression of the polypeptide or its altered light response, as compared to the control plant, said altered light response characterized by greater yield, longer petioles, longer hypocotyls, greater internode length, and/or more upright leaves.

25. The method of claim 20, wherein the method steps further comprise:
(c) selfing or crossing the transformed dicot plant with itself or another plant, respectively, to produce a transgenic seed.

26. The transgenic dicot plant of claim 14, wherein the polypeptide comprises SEQ ID NO: 2, and the transgenic dicot plant has greater early season growth, greater height, greater stem diameter, greater resistance to lodging, greater secondary rooting, greater cold tolerance, greater tolerance to water deprivation, reduced stomatal conductance, greater water use efficiency, altered C/N sensing, greater low nitrogen tolerance, greater low phosphorus tolerance, greater tolerance to hyperosmotic stress, greater early season vigor, greater late season growth, greater late season vigor, a greater number of mainstem nodes, greater estimated stand count, greater internode length, and/or greater canopy coverage, as compared to the control plant.

* * * * *